US012805783B2

(12) United States Patent
Yi et al.

(10) Patent No.: US 12,805,783 B2
(45) Date of Patent: Nov. 24, 2026

(54) BIOINSPIRED WATER SHRINK FILM FOR SHAPE-ADAPTIVE BIOELECTRONICS

(71) Applicant: Nanyang Technological University, Singapore (SG)

(72) Inventors: Junqi Yi, Singapore (SG); Xiaodong Chen, Singapore (SG)

(73) Assignee: Nanyang Technological University, Singapore (SG)

( * ) Notice: Subject to any disclaimer, the term of this patent is extended or adjusted under 35 U.S.C. 154(b) by 246 days.

(21) Appl. No.: 18/704,282

(22) PCT Filed: Oct. 26, 2022

(86) PCT No.: PCT/SG2022/050764
§ 371 (c)(1),
(2) Date: Apr. 24, 2024

(87) PCT Pub. No.: WO2023/075689
PCT Pub. Date: May 4, 2023

(65) Prior Publication Data

US 2024/0415435 A1 Dec. 19, 2024

(30) Foreign Application Priority Data

Oct. 26, 2021 (SG) .......................... 10202111897W

(51) Int. Cl.
*A61B 5/259* (2021.01)
*A61B 5/265* (2021.01)
(Continued)

(52) U.S. Cl.
CPC .............. *A61B 5/259* (2021.01); *A61B 5/265* (2021.01); *A61B 5/266* (2021.01); *C08G 83/007* (2013.01);
(Continued)

(58) Field of Classification Search
CPC ......... A61B 5/259; A61B 5/265; A61B 5/266; A61B 2562/125; A61B 2562/164;
(Continued)

(56) References Cited

U.S. PATENT DOCUMENTS

2016/0100768 A1* 4/2016 Someya ................ A61B 5/277 29/829
2024/0309201 A1* 9/2024 Bao ...................... C09D 165/00

FOREIGN PATENT DOCUMENTS

| | | | |
|---|---|---|---|
| CN | 105040279 | A | 11/2015 |
| EP | 0800409 | B1 | 3/2003 |
| WO | 2015051085 | A2 | 4/2015 |

OTHER PUBLICATIONS

Rydevik, et al.; U. Effects of graded compression on intraneural blood flow: An in vivo study on rabbit tibial nerve. The Journal of Hand Surgery 6, 3-12 (1981).
(Continued)

*Primary Examiner* — Eun Hwa Kim
(74) *Attorney, Agent, or Firm* — Patterson + Sheridan, LLP

(57) ABSTRACT

Disclosed herein are a supercontractible thin film comprising crystalline inclusion complex domains formed from poly(pseudo)rotaxanes or polyrotaxanes, and oriented polyethylene oxide domains physically crosslinked to the crystalline inclusion complex domains, wherein the poly(pseudo)rotaxanes or polyrotaxanes are formed from α-cyclodextrin and a polyethylene glycol having a number average molecular weight of from 500 to 10,000 Daltons, the polyethylene oxide has a number average molecular weight of from 200,000 to 10,000,000 Daltons, and the supercontractible thin film contracts by more than 50% of its original length upon wetting with water, a shape-adaptive supercontractile electrode and a shape-adaptive supercontractile electronic device. Also disclosed herein are methods
(Continued)

of forming a supercontractible thin film, a freestanding film, and an electrode composite material.

20 Claims, 26 Drawing Sheets

(51) Int. Cl.
*A61B 5/266* (2021.01)
*C08G 83/00* (2006.01)
*C08J 5/18* (2006.01)

(52) U.S. Cl.
CPC .......... *C08J 5/18* (2013.01); *A61B 2562/125* (2013.01); *A61B 2562/164* (2013.01); *C08J 2371/02* (2013.01)

(58) Field of Classification Search
CPC ............. A61N 1/0504; A61N 1/36042; A61N 1/36057; C08J 5/18; C08J 2405/16; C08G 83/007
See application file for complete search history.

(56) References Cited

OTHER PUBLICATIONS

Sakai, Y. et al.; Fabrication and structural analysis of polyrotaxane fibers and films. Journal of Physics: Condensed Matter 23, 284108 (2011).
Shih, W. K.; Shrinkage modeling of polyester shrink film. Polymer Engineering & Science 34, 1121-1128 (1994).
Stroet, M. et al.; Automated Topology Builder Version 3.0: Prediction of Solvation Free Enthalpies in Water and Hexane. Journal of Chemical Theory and Computation 14, 5834-5845 (2018).
Takahashi, et al.; Structural Studies of Polyethers, (-(CH2)m-O-)n. X. Crystal Structure of Poly(ethylene oxide). Macromolecules 6, 672-675 (1973).
Topchieva, et al.; Two-Phase Channel Structures Based on $\alpha$-Cyclodextrin-Polyethylene Glycol Inclusion Complexes. Langmuir 20, 9036-9043 (2004).
Trznadel;. Thermally stimulated shrinkage forces in oriented polymers: Induction time. Polymer 27, 871-876 (1986).
Work, R. W.; A Comparative Study of the Supercontraction of Major Ampullate Silk Fibers of Orb-Web-Building Spiders (Araneae). The Journal of Arachnology 9, 299-308 (1981).
Yan, X. et al.; Quadruple H-Bonding Cross-Linked Supramolecular Polymeric Materials as Substrates for Stretchable, Antitearing, and Self-Healable Thin Film Electrodes. Journal of the American Chemical Society 140, 5280-5289 (2018).
Yang, et al.; Hydrogel ionotronics. Nature Reviews Materials 3, 125-142 (2018).
Yarger, et al.; Uncovering the structure-function relationship in spider silk. Nature Reviews Materials 3, 18008 (2018).
Yuk, et al.; Hydrogel bioelectronics. Chemical Society Reviews 48, 1642-1667 (2019).
Yuk, H. et al.; Skin-inspired hydrogel-elastomer hybrids with robust interfaces and functional microstructures. Nature Communications 7, 12028 (2016).
Zhang, Y. et al.; Climbing-inspired twining electrodes using shape memory for peripheral nerve stimulation and recording. Science Advances 5, eaaw1066 (2019).
Kato, K. et al.; A significant impact of host-guest stoichiometry on the extensibility of polyrotaxane gels Chem. Commun. 51, 16180 (2015).
Takashima, Y. et al.; Expansion-contraction of photoresponsive artificial muscle regulated by host-guest interactions. Nat Commun 3, 1270 (2012).
Wu, Y. et al.; Biomimetic Supramolecular Fibers Exhibit Water-Induced Supercontraction. Advanced Materials 30, 1707169, doi: 10.1002/adma.201707169 (2018).
International Search Report and Written Opinion in related application PCT/SG2022/050764 dated Apr. 27, 2023.
Uyar, T. et al., Electrospinning of Cyclodextrin-Pseudopolyrotaxane 1-33 Nanofibers. Angew Chem Int Ed Engl., Nov. 5, 2008, vol. 47, No. 47, pp. 9108-9111 [Retrieved on Apr. 27, 2023] <DOI: 10.1002/AN IE.200803352> pp. 9109-9911 O.
Shen, G., Recent advances of flexible sensors for biomedical applications. 1-33; Progress in Natural Science: Materials International, Oct. 21, 2021, vol. 31, pp. 872-882 [Retrieved on Apr. 27, 2023] <DOI: 10.1016/J.PNSC.2021.10.005 > Whole document.
Ampanozi et al.; Comparing fist size to heart size is not a viable technique to assess cardiomegaly. Cardiovascular Pathology 36, 1-5 (2018).
Asadzadeh, et al,; The effect of chitosan and PEG polymers on stabilization of GF-17 structure: A molecular dynamics study. Carbohydrate Polymers 237, 116124 (2020).
Berendsen; The missing term in effective pair potentials. The Journal of Physical Chemistry 91, 6269-6271 (1987).
Bettinger, C. J.; Recent advances in materials and flexible electronics for peripheral nerve interfaces. Bioelectronic Medicine 4, 6 (2018).
Blacklow, et al.; Bioinspired mechanically active adhesive dressings to accelerate wound closure. Science Advances 5, eaaw3963 (2019).
Boehler, C. et al.; Tutorial: guidelines for standardized performance tests for electrodes intended for neural interfaces and bioelectronics. Nat. Protoc. 15, 3557-3578 (2020).
Boutry, et al.; Wet webs work better: humidity, supercontraction and the performance of spider orb webs. The Journal of Experimental Biology 216, 3606 (2013).
Bower; An Introduction to Polymer Physics. 133-137 (Cambridge University Press, 2002).
Cai, P. et al.; Locally coupled electromechanical interfaces based on cytoadhesion-inspired hybrids to identify muscular excitation-contraction signatures. Nature Communications 11, 2183 (2020).
Cera, et al.; A bioinspired and hierarchically structured shape-memory material. Nat. Mater. 20, 242-249 (2021).
Chen; Cyclodextrin-based inclusion complexation bridging supramolecular chemistry and macromolecular self-assembly. Chemical Society Reviews 40, 2254-2266 (2011).
Choi, et al.; Highly conductive, stretchable and biocompatible Ag—Au core-sheath nanowire composite for wearable and implantable bioelectronics. Nature Nanotechnology 13, 1048-1056 (2018).
Choi, et al.; Highly elastic binders integrating polyrotaxanes for silicon microparticle anodes in lithium ion batteries. Science 357, 279 (2017).
Cogan; Neural Stimulation and Recording Electrodes. Annual Review of Biomedical Engineering 10, 275-309 (2008).
Essmann, et al.; A smooth particle mesh Ewald method. The Journal of Chemical Physics 103, 8577-8593 (1995).
Frostell, et al.; Review of the Segmental Diameter of the Healthy Human Spinal Cord. Front Neurol 7, 238-238 (2016).
Ganji, M. et al.; Scaling Effects on the Electrochemical Stimulation Performance of Au, Pt, and PEDOT:PSS Electrocorticography Arrays. Adv. Funct. Mater. 27, 1703019 (2017).
Gao, et al.; Changes in nerve microcirculation following peripheral nerve compression. Neural Regeneration Research 8, 1041-1047 (2013).
Giesa, et al; Unraveling the Molecular Requirements for Macroscopic Silk Supercontraction. ACS Nano 11, 9750-9758 (2017).
Greenspan; Humidity Fixed Points of Binary Saturated Aqueous Solutions. Journal of Research of the National Bureau of Standards-A. Physics and Chemistry 81 A, 89-96 (1977).
Hammer, et al.; Human Vagus Nerve Branching in the Cervical Region. Plos One 10, e0118006 (2015).
Hanlon; Handbook of Package Engineering. (CRC Press, 1998).
Harada et al.; M. Complex formation between poly(ethylene glycol) and $\alpha$-cyclodextrin. Macromolecules 23, 2821-2823 (1990).
Hess, B., Kutzner, C., van der Spoel, D. & Lindahl, E. Gromacs 4: Algorithms for Highly Efficient, Load-Balanced, and Scalable Molecular Simulation. Journal of Chemical Theory and Computation 4, 435-447 (2008).

(56) References Cited

OTHER PUBLICATIONS

Huang et al.; Study of the inclusion compounds formed between α-cyclodextrin and high molecular weight poly (ethylene oxide) and poly(ϵ-caprolactone). Polymer 39, 4857-4865 (1998).
Hubbard, et al.; Hydrogel/Elastomer Laminates Bonded via Fabric Interphases for Stimuli-Responsive Actuators. Matter 1, 674-689 (2019).
Humphrey, et al.; Visual molecular dynamics. Journal of Molecular Graphics 14, 33-38 (1996).
Kakade, et al.; Electric Field Induced Orientation of Polymer Chains in Macroscopically Aligned Electrospun Polymer Nanofibers. Journal of the American Chemical Society 129, 2777-2782 (2007).
Kim, H. et al.; Bio-Inspired Stretchable and Contractible Tough Fiber by the Hybridization of GO/MWNT/Polyurethane. ACS Applied Materials & Interfaces 11, 31162-31168 (2019).
Kim, et al.; Next-generation flexible neural and cardiac electrode arrays. Biomedical Engineering Letters 4, 95-108 (2014).
Kim, et al.; A selective membrane-targeting repurposed antibiotic with activity against persistent methicillin-resistant *Staphylococcus aureus* Proceedings of the National Academy of Sciences 116, 16529 (2019).
Kutz; Mechanical Engineers' Handbook, vol. 1: Materials and Engineering Mechanics. 358 (Wiley, 2015).
Lacour, et al.; Materials and technologies for soft implantable neuroprostheses. Nature Reviews Materials 1, 16063 (2016).
Lewis; Spider Silk: Ancient Ideas for New Biomaterials. Chemical Reviews 106, 3762-3774 (2006).
Lin, et al.; X. Muscle-like fatigue-resistant hydrogels by mechanical training. Proceedings of the National Academy of Sciences 116, 10244 (2019).
Liu, D. et al.; Spider dragline silk as torsional actuator driven by humidity. Science Advances 5, eaau9183 (2019).
Liu, Y. et al.; Soft and elastic hydrogel-based microelectronics for localized low-voltage neuromodulation. Nature Biomedical Engineering 3, 58-68 (2019).
Liu, et al.; F. Relationships between supercontraction and mechanical properties of spider silk. Nature Materials 4, 901-905 (2005).
Liu, Z. et al.; Highly Stable and Stretchable Conductive Films through Thermal-Radiation-Assisted Metal Encapsulation. Advanced Materials 31, 1901360 (2019).
Ma, Y. et al.; Bioinspired high-power-density strong contractile hydrogel by programmable elastic recoil. Science Advances 6, eabd2520 (2020).
Malde, A. K. et al.; An Automated Force Field Topology Builder (ATB) and Repository: Version 1.0. Journal of Chemical Theory and Computation 7, 4026-4037 (2011).
Mao, Q. et al.; Self-contracting oxidized starch/gelatin hydrogel for noninvasive wound closure and wound healing. Materials & Design 194, 108916 (2020).
Matsuda, T., Kawakami, R., Namba, R., Nakajima, T. & Gong, J. P. Mechanoresponsive self-growing hydrogels inspired by muscle training. Science 363, 504 (2019).
Minev, et al.; Electronic dura mater for long-term multimodal neural interfaces. Science 347, 159 (2015).
Noro, J. et al.; Catalytic Activation of Esterases by PEGylation for Polyester Synthesis. ChemCatChem 11, 2490-2499 (2019).
Pan, S. et al.; Mechanically Interlocked Hydrogel-Elastomer Hybrids for On-Skin Electronics. Adv. Funct. Mater. 30, 1909540 (2020).
Pang, X. et al.;, Ultralarge Contraction Directed by Light-Driven Unlocking of Prestored Strain Energy in Linear Liquid Crystal Polymer Fibers. Advanced Functional Materials 30, 2002451 (2020).
Park, S. I. et al.; Soft, stretchable, fully implantable miniaturized optoelectronic systems for wireless optogenetics. Nature Biotechnology 33, 1280-1286 (2015).
Parvizi, et al.; in High Yield Orthopaedics (eds Javad Parvizi & Gregory K. Kim) 177-178 (W.B. Saunders, 2010).
Qi, et al.; X. Elastic substrates for stretchable devices. MRS Bulletin 42, 103-107 (2017).

* cited by examiner

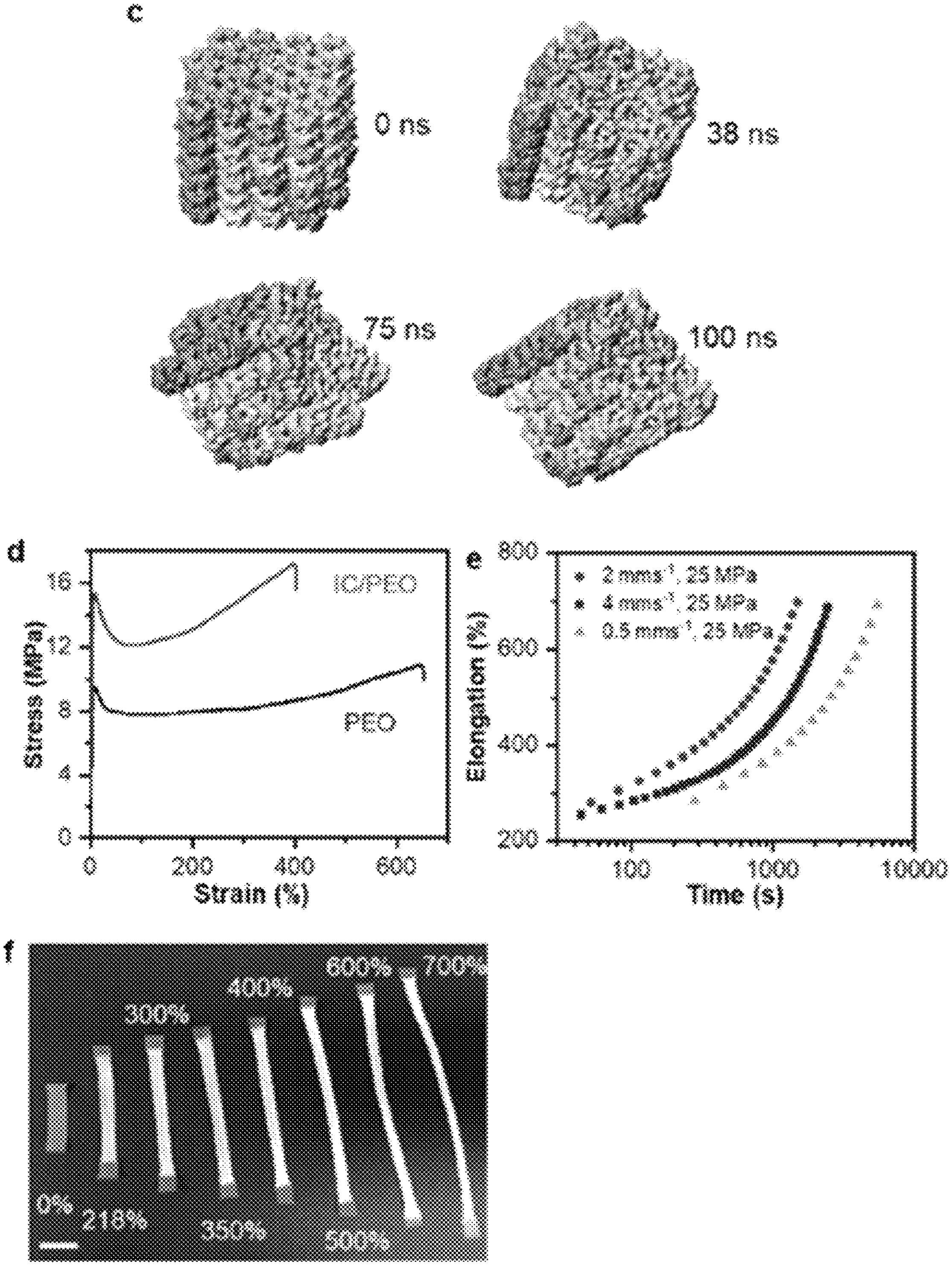
FIG. 3c-f

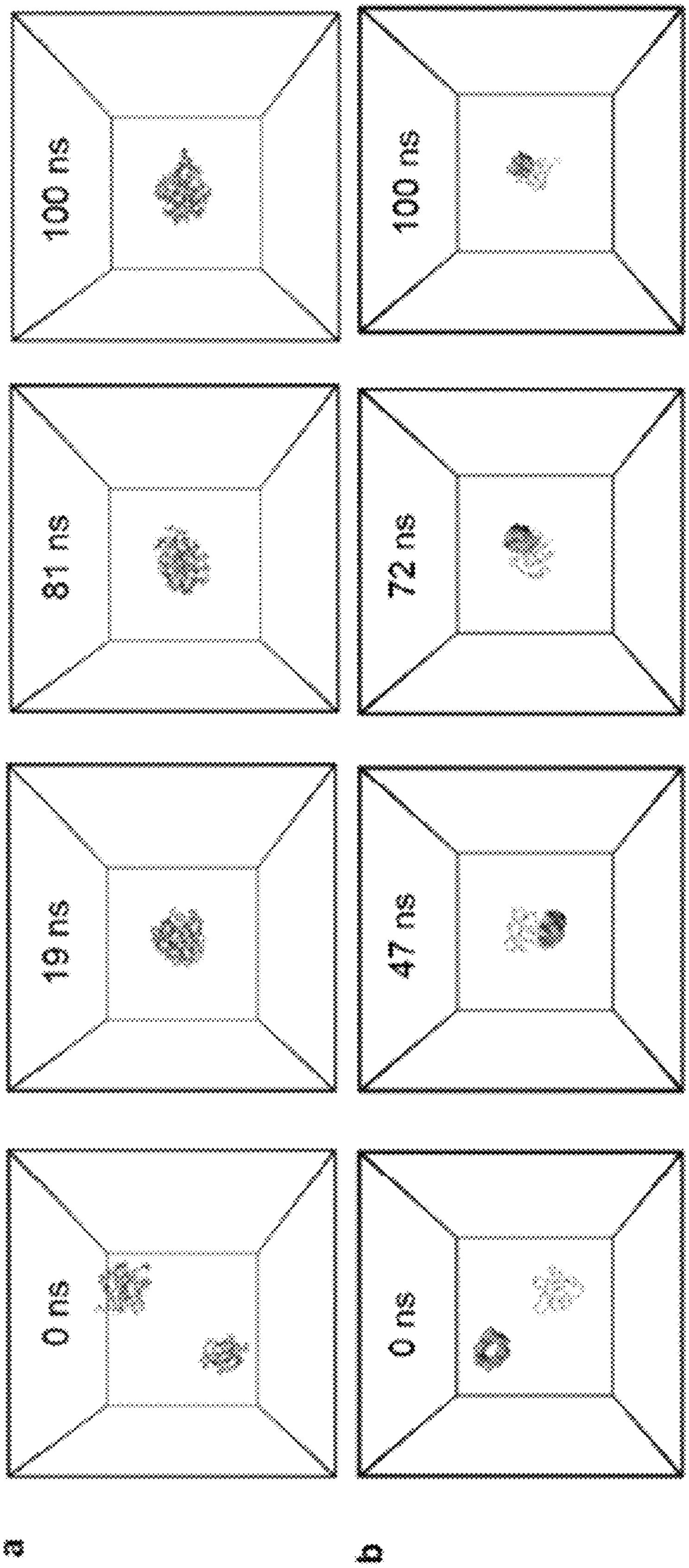
FIG. 12a-b

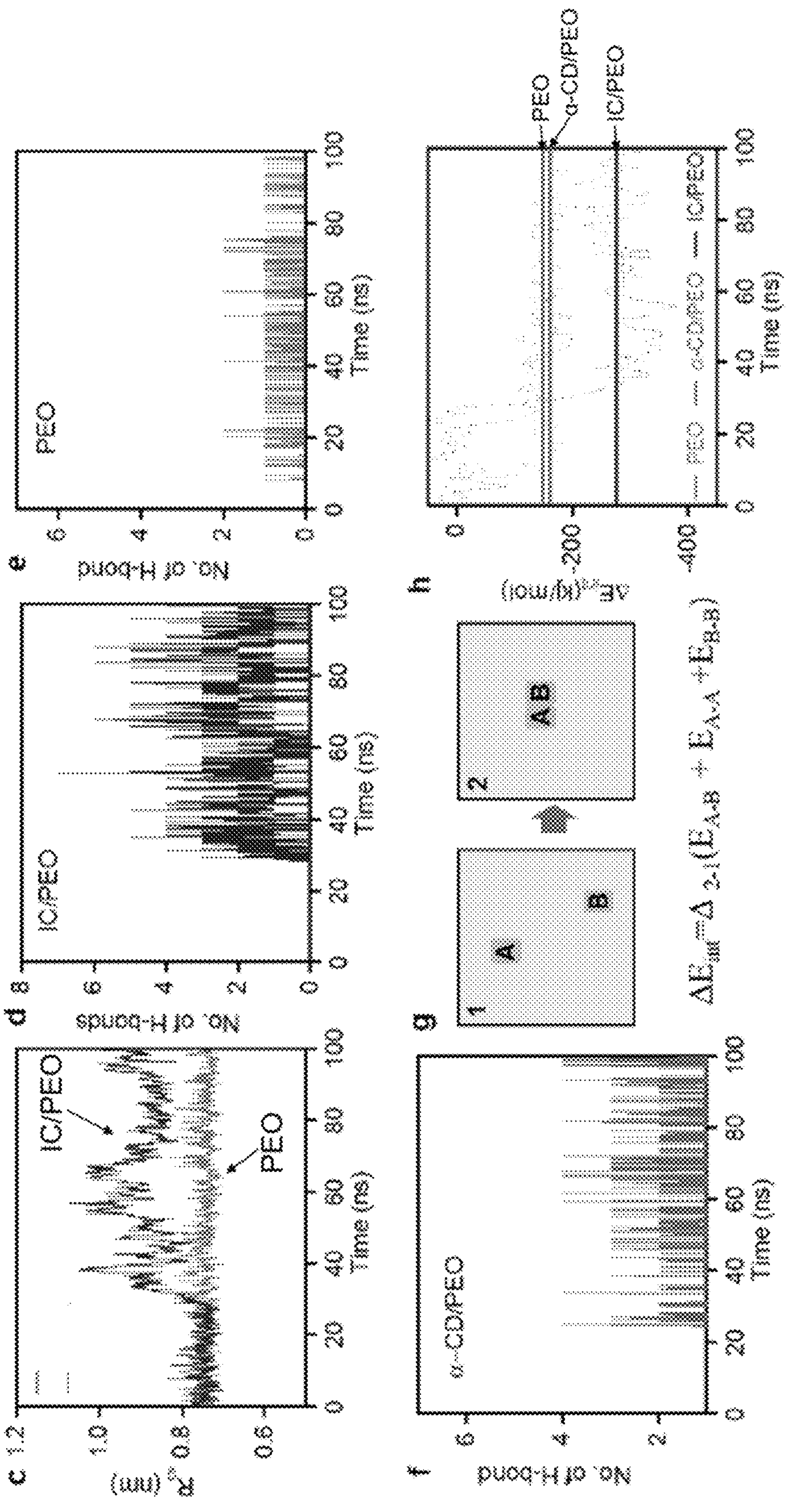
FIG. 12c-h

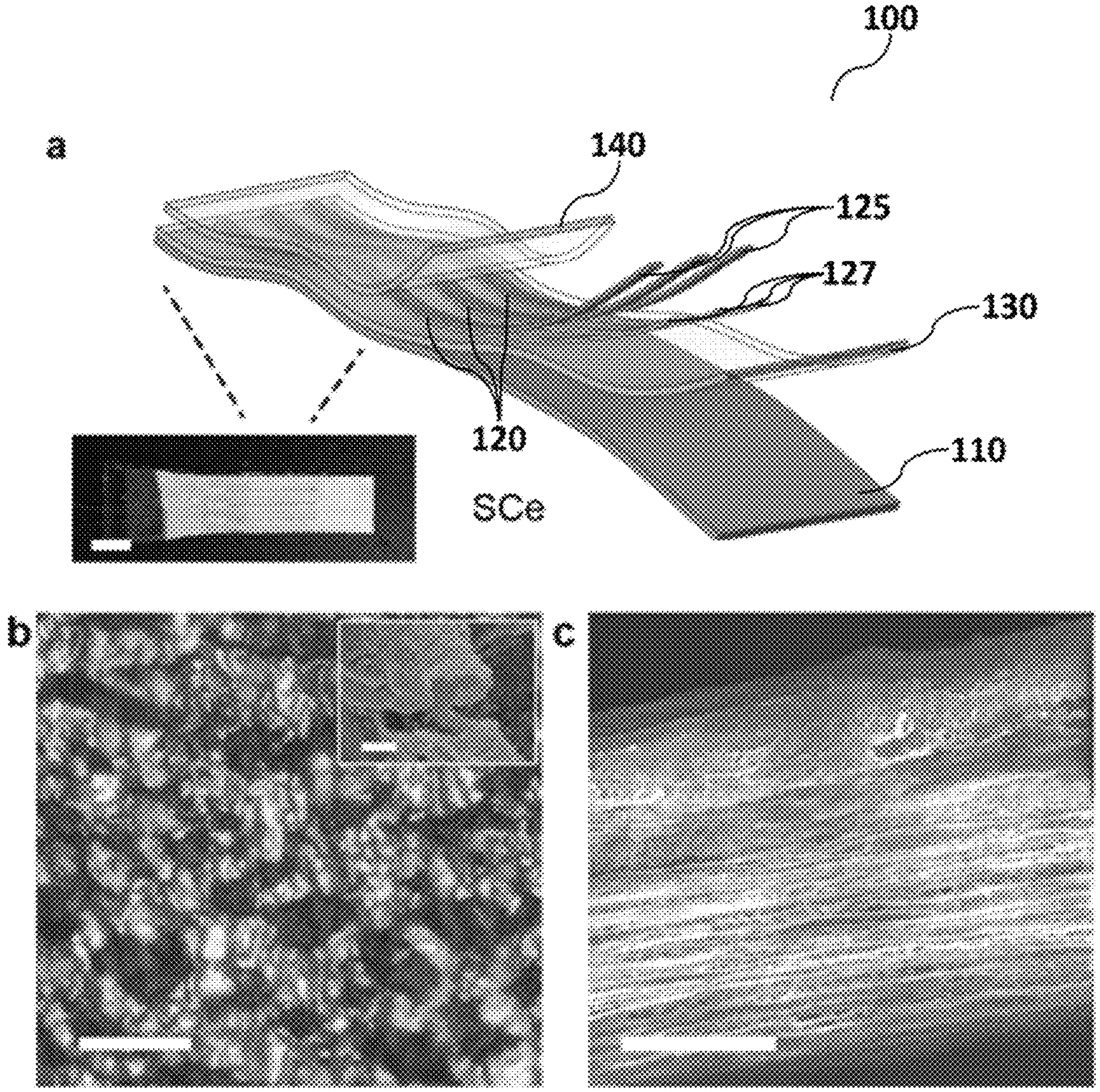
FIG. 13a-c

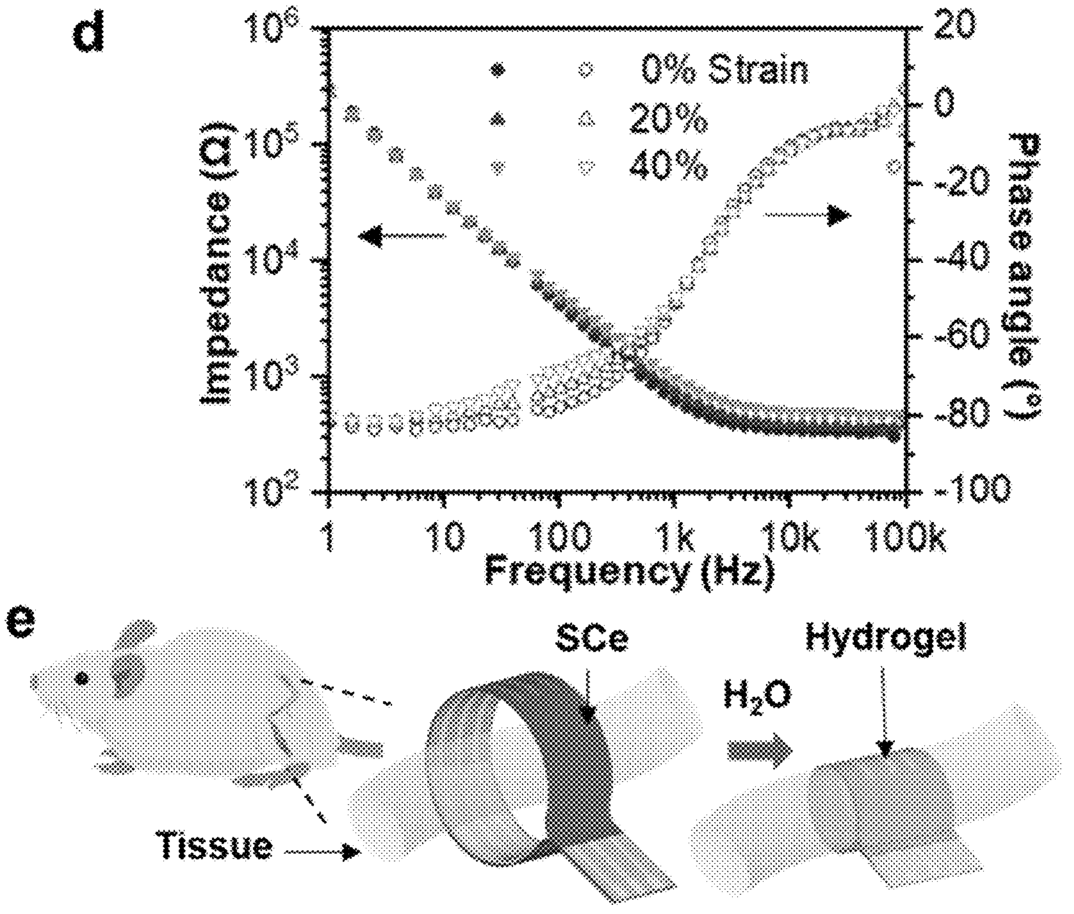
FIG. 13d-e

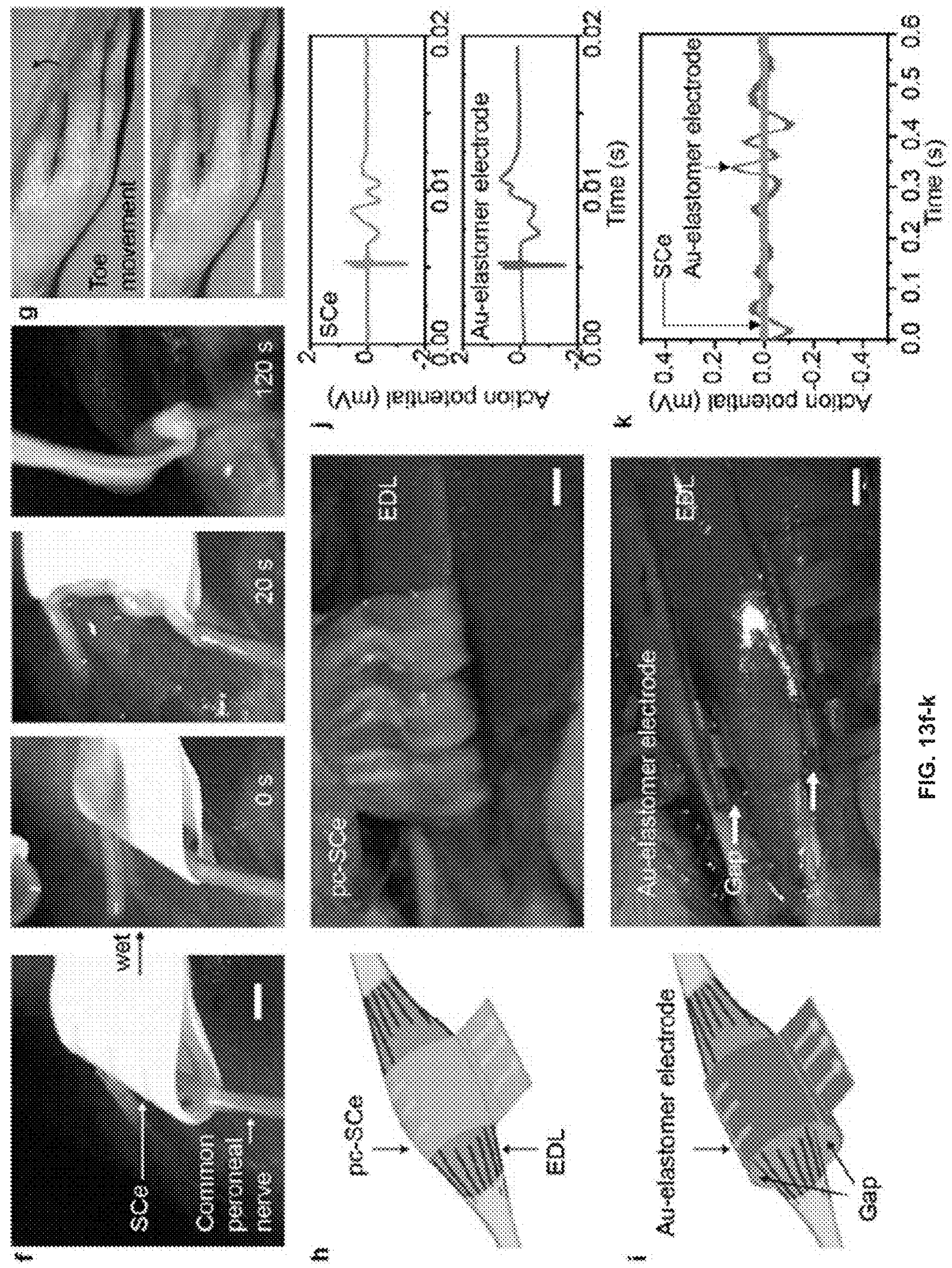
FIG. 13f-k

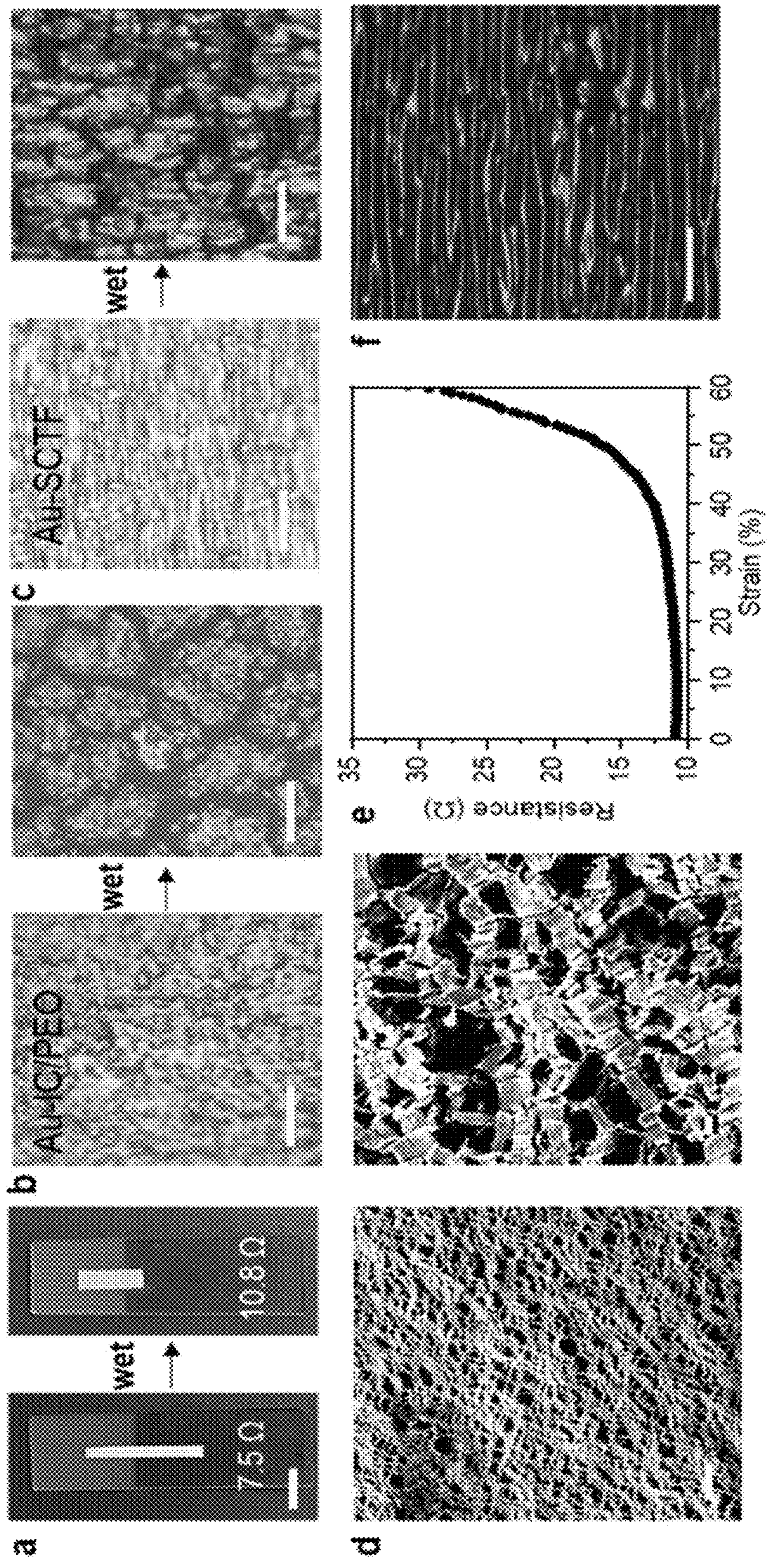
FIG. 15a-f

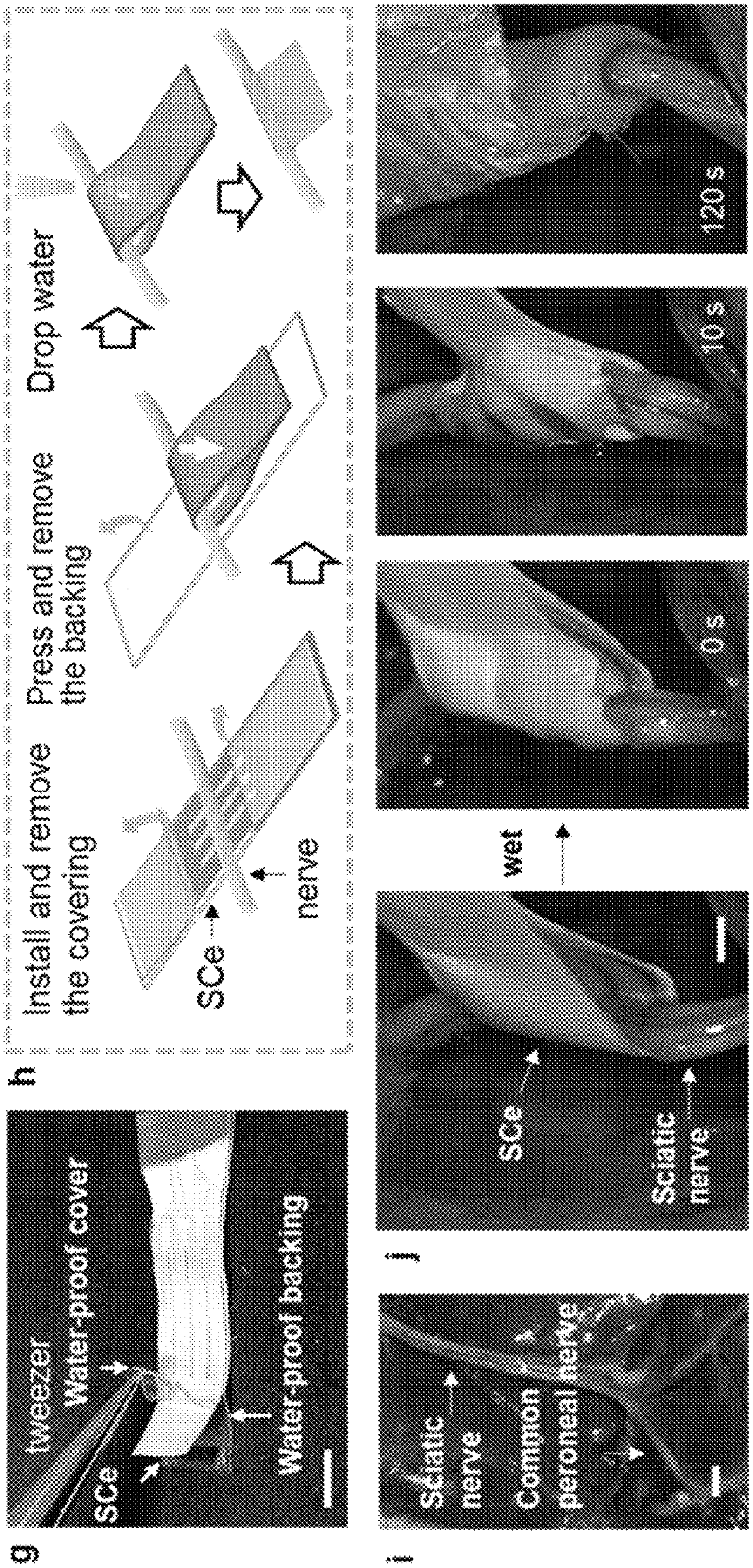
FIG. 15g-j

BIOINSPIRED WATER SHRINK FILM FOR SHAPE-ADAPTIVE BIOELECTRONICS

FIELD OF INVENTION

The current invention relates to a supercontractible thin film that can be used in a number of applications, such as use in electrodes that can be applied to the body internally or externally. Also disclosed herein are electrodes making use of the supercontractible thin film as well as methods of manufacturing both materials and their uses.

BACKGROUND

The listing or discussion of a prior-published document in this specification should not necessarily be taken as an acknowledgement that the document is part of the state of the art or is common general knowledge.

Bioelectronic devices have evolved from rigid fixed shapes to soft, flexible, and stretchable ones that interface better with soft tissues. Among them, shape-wrapping electronics using soft elastomer and shape memory materials have attracted increasing attention since they can interface well with tissues and can withstand dynamic environments without additional suturing fixation process. However, their size and shape need to be customized in advance to fit the target organ. One inspiring application from the packaging industry is heat shrink polymers that contract and spontaneously wrap themselves around irregular sized and shaped objects upon heating. Unfortunately, such polymers (e.g. polyvinyl chloride, polyolefin) are unsuitable for implantation because they are too hard (Young's modulus, ~1 GPa) and typically contract at temperatures>90° C. (FIG. 1*a*). For implantation, we need soft and stretchable materials that contract greatly (>50%) and rapidly (within seconds) under stimulus that are compatible with vulnerable tissues.

FIG. 1*b* shows the reported biological and synthetic materials which can contract rapidly under different stimuli. Some liquid crystal polymers exhibit light-induced large contraction. However, the light with short wavelength, especially UV light could damage tissues. By contrast, water is a safer trigger. In nature, spider-dragline-silk show unique water-induced contraction (termed supercontraction). Such supercontraction results from its hierarchical structure where oriented polymer chains in amorphous domains held by hydrogen bonds and crosslinked by stable β-sheet crystallites (FIG. 2*a*). Water from wetting breaks these hydrogen bonds and induces molecular chain recoiling, causing large contraction. Preparing synthetic supercontractile materials is challenging. Overly dense hydrogen bonds hinder supercontraction while sparse ones are unstable under ambient humidity. Supramolecular polymer, polymer composite and reconfiguration keratin were recently reported to fabricate supercontractile fibres. However, like spider silk, they are too rigid for soft tissue applications. Hydrogels with large water contents and tissue-like softness were thought to be compatible with tissues. However, reported rapid contractile hydrogels triggered by acid is not suitable for implant. Those triggered by body-temperature are either exhibit slow contraction or not stable at room temperature. Besides, it is still challenging to combine hydrogels with other layers related to electronics integration, such as electron conductive metal layers and hydrophobic insulation layers due to the hydration layer and different surface energy.

Therefore, there exists a need for new supercontractible materials to overcome the challenges described above.

SUMMARY OF INVENTION

Aspects and embodiments of the invention will now be discussed by reference to the following non-limiting embodiments.

1. A supercontractible thin film comprising:
   - crystalline inclusion complex domains formed from poly(pseudo)rotaxanes or polyrotaxanes; and
   - oriented polyethylene oxide domains physically cross-linked to the crystalline inclusion complex domains, wherein:
     - the poly(pseudo)rotaxanes or polyrotaxanes are formed from α-cyclodextrin and a polyethylene glycol having a number average molecular weight of from 500 to 10,000 Daltons;
     - the polyethylene oxide has a number average molecular weight of from 200,000 to 10,000,000 Daltons; and
     - the supercontractible thin film contracts by more than 50% of its original length upon wetting with water.
2. The supercontractible thin film according to Clause 1, wherein the thin film has one or both of a microporous structure and aligned fibrillar bridges.
3. The supercontractible thin film according to Clause 1 or Clause 2, wherein the supercontractible thin film exhibits a contraction rate relative to its original length of from 10 to 50%/s upon wetting with water.
4. The supercontractible thin film according to Clause 3, wherein the supercontractible thin film exhibits a contraction rate relative to its original length of about 30%/s upon wetting with water.
5. The supercontractible thin film according to any one of the preceding clauses, wherein the weight:weight ratio of polyethylene glycol:α-cyclodextrin is from 1:1 to 1:20, such as from 1:5 to 1:15, such as about 1:10.
6. The supercontractible thin film according to any one of the preceding clauses, wherein the weight:weight ratio of α-cyclodextrin:polyethylene oxide is from 1:1 to 10:1, such as from 2:1 to 5:1, such as about 10:6.
7. The supercontractible thin film according to any one of the preceding clauses, wherein the weight:weight ratio of polyethylene glycol:α-cyclodextrin:polyethylene oxide is about 1:10:6.
8. The supercontractible thin film according to any one of the preceding clauses, wherein:
   - (a) the supercontractible thin film is stable at a temperature of less than 60° C. and a relative humidity of less than 80%; and/or
   - (b) the film is stable in an aqueous solvent for a period of at least two weeks; and/or
   - (c) the poly(pseudo)rotaxanes or polyrotaxanes are formed from α-cyclodextrin and a polyethylene glycol having a number average molecular weight of from 1,000 to 7,500 Daltons, such as from 1,500 to 5,000 Daltons, such as from 1,750 to 2,500 Daltons, such as about 2,000 Daltons; and/or
   - (d) the polyethylene oxide has a number average molecular weight of from 500,000 to 7,000,000 Daltons, such as from 750,000 to 5,000,000 Daltons, such as from 1,000,000 to 3,000,000 Daltons, such as about 2,000,000 Daltons.
9. The supercontractible thin film according to any one of the preceding clauses, wherein the supercontractible thin film has a Young's modulus of from 50 MPa to 1 GPa, such as from 200 to 550 MPa, such as from 260 to 500 MPa, optionally wherein the supercontractible thin film after wetting has a Young's modulus of from 10 to 500 kPa, such as from 50 to 100 kPa, such as about 80 kPa after wetting with water.

10. The supercontractible thin film according to any one of the preceding clauses, wherein the supercontractible thin film has been subjected to longitudinal stretching to provide the oriented polyethylene oxide domains, where the longitudinal stretching results in a film having a length that is from 218 to 700% of the original length of a freestanding thin film material comprising:
 crystalline inclusion complex domains formed from polyrotaxanes or poly(pseudo)rotaxanes; and
 unoriented polyethylene oxide domains physically crosslinked to the crystalline inclusion complex domains.

11. The supercontractible thin film according to any one of the preceding clauses, wherein the supercontractible thin film contracts by from 35 to 65% of its original length upon wetting with water.

12. A shape-adaptive supercontractile electrode comprising:
 a first layer of a supercontractible thin film according to any one of Clauses 1 to 11 as a substrate;
 an electrode composite material comprising:
  a second layer of supercontractible thin film according to any one of Clauses 1 to 11 as an electrode support layer; and
  a conductive metal compound layer or, more particularly, a metal layer arranged to form electrodes and attached to the second supercontractible thin film layer;
 a first insulation layer sandwiched between the first supercontractible thin film layer and the electrode composite material; and
 a second insulation layer on laid on top of the electrode composite material, wherein the first and second insulation layers are formed from an insulative polymeric material.

13. The shape-adaptive supercontractile electronic device according to Clause 12, wherein the insulative polymeric material is selected from PDMS or a thermoplastic elastomer, optionally wherein the thermoplastic elastomer is a self-healing thermoplastic elastomer.

14. The shape-adaptive supercontractile electronic device according to Clause 13, wherein the insulative polymeric material is styrene-ethylene/butylene-styrene.

15. The shape-adaptive supercontractile electronic device according to any one of Clauses 12 to 14, wherein:
 (AA) when a metal layer is present, the metal is selected from one or more of platinum and, more particularly, gold, silver, and copper, or when a conductive metal compound layer is present the conductive metal compound is selected from one or both of iridium oxide and titanium nitride; and/or
 (AB) the electrode composite material is patterned; and/or
 (AC) the electrode composite material further comprises a layer of an insulative polymeric material on top of the conductive metal compound layer or, more particularly, the metal layer, optionally wherein the insulative polymeric material is selected from PDMS or a thermoplastic elastomer, more optionally wherein the thermoplastic elastomer is a self-healing thermoplastic elastomer (e.g. styrene-ethylene/butylene-styrene).

16. A supercontractile electronic device comprising a supercontractible thin film layer according to any one of Clauses 1 to 11.

17. A supercontractile electronic device comprising a shape-adaptive supercontractile electrode according to any one of Clauses 12 to 15.

18. A method of forming a supercontractible thin film as described in any one of Clauses 1 to 11, the method comprising the steps of:
 (ai) providing a freestanding thin film comprising:
  a crystalline inclusion complex domains formed from polyrotaxanes or poly(pseudo)rotaxanes; and
  unoriented polyethylene oxide domains physically crosslinked to the crystalline inclusion complex domains, wherein:
   the polyrotaxanes or poly(pseudo)rotaxanes are formed from α-cyclodextrin and a polyethylene glycol having a number average molecular weight of from 500 to 10,000 Daltons; and
   the polyethylene oxide has a number average molecular weight of from 200,000 to 10,000,000 Daltons; and
 (aii) drawing a film by applying a strain to achieve an elongation of the film of from 100% to 300% of its original length to provide the supercontractible thin film.

19. The method according to Clause 18, wherein the method further comprises further repeatedly drawing the supercontractible thin film by a applying a strain to obtain a desired length, optionally wherein the desired length is from 218 to 700% of the original length of the freestanding film.

20. The method according to Clause 18 or Clause 19, wherein the strain is from 10 to 60 MPa, such as about 25 MPa.

21. The method according to any one of Clauses 18 to 20, wherein the drawing involves a drawing speed of from 0.1 to 5 mm/s, such as about 2 mm/s.

22. The method according to any one of Clauses 18 to 21, wherein:
 (aa) the polyrotaxanes or poly(pseudo)rotaxanes are formed from α-cyclodextrin and a polyethylene glycol having a number average molecular weight of from 1,000 to 7,500 Daltons, such as from 1,500 to 5,000 Daltons, such as from 1,750 to 2,500 Daltons, such as about 2,000 Daltons; and/or
 (ab) the polyethylene oxide has a number average molecular weight of from 500,000 to 7,000,000 Daltons, such as from 750,000 to 5,000,000 Daltons, such as from 1,000,000 to 3,000,000 Daltons, such as about 2,000,000 Daltons.

23. A method of forming a freestanding film as described in Clause 18, the method comprising:
 (bi) providing a composition comprising α-cyclodextrin-poly(ethylene glycol) inclusion complex and a solvent; and
 (bii) adding poly(ethylene oxide) (PEO) to the composition and aging for a period of time at a temperature of from 40 to 80° C., such as about 60° C. composition to provide a freestanding film precursor solution; and
 (biii) drying the freestanding film precursor solution to provide the freestanding film precursor.

24. A method of forming an electrode composite material, the method comprising:
 (ci) providing a supercontractible thin film according to any one of Clauses 1 to 11 as a substrate; and
 (cii) depositing a conductive metal compound or, more particularly, a metal by thermal deposition onto the supercontractible thin film substrate to form a conductive metal compound layer or, more particularly, a metal layer.

25. The method according to Clause 24, wherein the deposition rate of the conductive metal compound or, more particularly, the metal is selected to avoid contraction of the supercontractible thin film during the deposition process, optionally wherein the deposition rate is from 0.1 to 0.5 Å/s, such as about 0.3 Å/s.

26. The method according to Clause 24 or Clause 25, wherein the thermal deposition uses a vacuum, optionally wherein the vacuum is less than or equal to about $2\times10^{-6}$ Torr.

27. The method according to any one of Clauses 25 to 26, wherein the conductive metal compound layer or, more particularly, the metal layer is deposited in a desired pattern on the substrate.

28. The method according to any one of Clauses 25 to 27, wherein when a metal layer is present, the metal is selected from one or more of platinum and, more particularly, gold, silver, and copper, or when a conductive metal compound layer is present the conductive metal compound is selected from one or both of iridium oxide and titanium nitride.

29. The method according to any one of Clauses 25 to 28, wherein the method further comprises attaching conductive leads to the conductive metal compound layer or, more particularly, the metal layer, optionally wherein the conductive leads are attached by way of a conductive adhesive.

30. The method according to any one of Clauses 25 to 29, wherein the supercontractible thin film of the electrode has a first surface on which the conductive metal compound layer or, more particularly, the metal layer is deposited and a second surface that has no deposition of a conductive metal compound or, more particularly, a metal on it, the method further comprises the step of attaching an insulative polymeric material onto the first surface of the supercontractible thin film of the electrode to provide an insulated electrode block, optionally wherein the insulative polymeric material is attached by spin coating.

31. The method according to Clause 30, wherein the insulated electrode block comprises areas patterned with the conductive metal compound layer or, more particularly, the metal layer and areas that do not contain the layers and the method further comprises substantially removing the areas that not contain the layers to form a patterned electrode.

32. The method according to Clause 31, further comprising the steps of:

(di) providing a substrate layer formed from a layer of supercontractible thin film according to any one of Clauses 1 to 11 and a first layer of an insulative polymeric material;

(dii) laying the patterned electrode on the first insulative polymeric material layer and encapsulating the patterned electrode by the deposition of a second layer of the insulative polymeric material onto the patterned electrode on the first insulative polymeric material layer, optionally wherein the second insulative polymeric material layer is formed by spin coating.

33. The method according to any one of Clauses 30 to 32, wherein the insulative polymeric material is selected from PDMS or a thermoplastic elastomer, optionally wherein the thermoplastic elastomer is a self-healing thermoplastic elastomer, optionally wherein the insulative polymeric material is styrene-ethylene/butylene-styrene.

DRAWINGS

FIG. 1 depicts the preparing of supercontractile thin film (SCTF). (a) Photographs of heat shrink polymer (polyvinyl chloride) wrapping a tissue-mimicking agarose gel with irregular shape. It contracted to wrap tightly around the hydrogel under 120° C. within seconds. The post-contraction (pc) polymer is much harder (~GPa) than its underlying gel (~kPa); (b) Graph shows the pc-Young's modulus and contraction ratio of different materials which can rapidly contract under different stimuli. ① represents water-triggered contraction, ② is high temperature (>90° C.), ③ represents light, ④ is acid and ⑤ represents body temperature (37° C.) triggered contraction. The shaded area represents the range of tissues' modulus (~kPa); (c) Photographs of SCTF wrapping an agarose gel with irregular shape. It contracted when wetted to conformably wrap around the underlying agarose gel and became a soft hydrogel thin film within seconds; (d) Schematic and photographs of mass-produced procedures for dry, flexible and freestanding SCTFs. It involves two steps: 1) solvent casting of polyethylene glycol (PEG)-α-Cyclodextrin (α-CD) inclusion complex (IC) mixture; and 2) two-step mechanical training (repeated cold drawing) to produce SCTFs with different elongation ratios; (e) Stress-strain curve of the first-step mechanical training shows drawing of IC/poly (ethylene oxide) (PEO) to 300% strain and unloaded returning to the initial position at 2 $mms^{-1}$ did not break the film. Inset: photographs show that cold drawing of IC/PEO film to 300% strain at 2 $mms^{-1}$ caused yielding (a visco-plastic deformation) and necking, which turned the transparent film white (left); (f) Stress-strain curve of the second-step mechanical training. In each cycle, the yielded film was drawn to a preset stress of 25 MPa and unloaded returning to its initial position at 2 $mms^{-1}$. Inset: a yielded film drawn to 700% strain through mechanical training; and (g) Relationship between the elongation ratio and cycle numbers for different preset stresses (15 MPa to 30 MPa) and crosshead speeds (0.5 $mms^{-1}$ to 4 $mms^{-1}$) show that elongation ratio increased linearly with cycle numbers for all conditions. Scale bar: (a,c) 1 cm; and (d) middle: 1 cm; and right: 5 mm.

FIG. 2 depicts the hierarchical structures of spider dragline silk and SCTF. (a) Schematic of the structure responsible for supercontraction in spider dragline silk. Silk's supercontraction results from its hierarchical structure consisting of water-penetrable amorphous domains crosslinked by stable β-sheet crystalline domains. The highly oriented polymer chains in the amorphous domains are fixed by hydrogen bonds. Water from wetting breaks these bonds and induces molecular chain recoiling, causing large contractions; and (b) SCTF is constructed by stable PEG-α-CD IC crystalline domains and water-penetrable semicrystalline PEO domains. SCTF has oriented PEO crystallites and microporous structure. Dissolution of PEO crystallites by penetrated water causes PEO chain's recoil and SCTF's contraction.

FIG. 3 depicts the fabrication of SCTF. (a) Scheme and photographs of stepwise fabrication process of free-standing IC/PEO thin film; (b) All-atom molecular dynamics (MD) simulations of spontaneous formation of inclusion complex in solution. As PEG (n=9) polymer penetrates through the α-CD, their interaction energy decreases. After formation of IC, the structure remains stable in long-time simulation; (c) MD simulations of crystalline IC which is stable and maintains the structure after 100 ns simulation in solution; (d) Tensile stress-strain curves for films drawn at 2 $mms^{-1}$ show that IC/PEO is stiffer (E~545 MPa) but less stretchable (~400%) than a pure PEO thin film (370 MPa, ~650%); (e) Time-dependent change in elongation ratio under crosshead speeds of 0.5 $mms^{-1}$, 2 $mms^{-1}$ and 4 $mms^{-1}$ show that drawing at 2 $mms^{-1}$ is most efficient; and (f) Photographs of IC/PEO (elongation 0%) and SCTFs with elongation ratios ranging from 218% to 700%. Scale bar: 1 cm.

FIG. 4 depicts the half cross-section of pc-SCTF tightly wrapping around a rod.

FIG. 5 depicts the supercontraction and post-contraction properties of SCTFs. (a) Rapid water-induced supercontraction of SCTF. SCTF contracted ~60% within 2 sec when wetted; (b) SCTFs became more contractile (contraction ratio increased from ~35% to ~65%) and softer (pc-Young's modulus decreased from ~200 kPa to ~25 kPa) as the elongation ratio increased from 218% to 700%. Samples were measured after soaking in water for 1 min. Error bars: standard deviation of four independent tests (n=4); (c) Humidity response tests show that SCTFs with elongation ratios ranging from 218% to 700% barely contracted at relative humidity (RH)<80%. Partial contraction began at RH=84% while large contractions happened at RH=94% and 97%. All samples (n=3) were tested after incubation in sealed chambers at fixed RH for 24 h; (d) Stress-strain curves show pc-SCTFs with elongation ratio between 218% and 400% broke at ~550% strain while those with larger elongation ratios broke at lower strains, indicating that stretchability decreased at elongation ratio>400%; (e) Supercontraction force generated by constrained SCTF-400% is transient with 60% decaying within 10 seconds (s) and only 5% remaining after 20 min. Inset: schematic of the test set-up. Testing gauge length was fixed at 0.6 $L_0$, where $L_0$ is the original length of SCTF-400%. Length after free contraction was ~0.4 $L_0$. Body temperature (37° C.) water was pumped into the chamber within 4 sec until the sample is completely submerged; and (f) LIVE/DEAD assay shows that the number of live normal human dermal fibroblasts cells after culturing for 24 h in the conditioned medium (prepared by soaking SCTF-400% in pristine culture medium) is comparable with cells cultured in pristine medium. Scale bar: (a) 3 mm; and (f) 100 μm.

FIG. 6 depicts the water content and impedance of wet IC/PEO and pc-SCTFs. (a) Water content of wet IC/PEO film (elongation ratio, 0%) and pc-SCTFs increased with the increase in elongation ratio (n=4); and (b) Electrochemical Impedance Spectroscopy (EIS) spectra of wet IC/PEO film and pc-SCTFs show that impedance decreased with the increase in elongation ratio. All samples had the same exposed area (1.40 $cm^2$) in phosphate buffered saline (PBS).

FIG. 7 depicts the experimental and theoretical characterization of SCTF microstructures. (a) SEM image shows that IC/PEO thin film has a dense surface with stacked platelets (arrows); (b) SEM image of SCTF-400% shows a rough and microporous surface with aligned fibrillar bridges (inset). Cold drawing direction is horizontal; (c) Longitudinal sectional scanning electron microscopy (SEM) image of SCTF-400% reveals a porous and aligned inner structure; (d) SEM image shows that the porous and aligned microstructures disappeared after SCTF-400% is exposed to RH=97%; (e) Two-dimensional (2D) wide-angle X-ray scattering (WAXS) patterns (left) reveal that SCTF-400% is anisotropic. Corresponding one-dimensional (1D) integrated curves from different scanning azimuthal directions (right) show constant intensities for peak a (100), b (110), d (210), and e (300), indicating that IC crystallite remained isotropic in SCTF-400%. Changing intensities for peak c (120) and f (032) show PEO crystallites are oriented; (f) Polarized optical microscopy images show that the large spherulites in PEO are absent in α-CD/PEO and IC/PEO thin films, and α-CD/PEO is more homogeneous than IC/PEO; (g) SEM and transmission electron microscopy (TEM) (inset) images of IC crystalline platelets. All SEM samples were observed directly without Au or Pt coating; and (h-j) MD simulations of the interactions inside IC/PEO, PEO/PEO, α-CD/PEO in aqueous solution. The snapshots show that PEO (49 ethylene oxide repeat units) bind to IC (6 α-CD) after 29 ns and remain aggregated within 100 ns simulation (h). The distribution of counts of H-bonds obtained from 60-100 ns in simulations shows that PEO formed more hydrogen bonds with IC than with PEO or α-CD (i). Interaction energy changes after and before the aggregation of two molecules in all three cases show that IC/PEO has the largest binding energy (j). Scale bars: (a-d, g) 1 μm; (f) 20 μm; and inset in (b) 200 nm.

FIG. 8 depicts the morphologies of IC/PEO, SCTFs and pc-SCTF. (a-d) SEM images showing the morphology changes of SCTFs with increase in training elongation. After cold drawing, both the surfaces and inner parts of SCTFs were porous with aligned microstructure, which became more obvious with increase in training elongation; (e) Longitudinal section of SCTF-400% shows that the inner of which is also porous with aligned structure; and (f) Longitudinal section SEM images of RH 97%-induced post-contraction SCTF-400%. After contraction, the porous and aligned microstructures disappeared. Scale bar: (a-d) 1 μm; and (e-f) 10 μm.

FIG. 9 depicts the 2D WAXS of IC/PEO, PEO and pc-SCTF. (a) 2D WAXS patterns of IC/PEO and corresponding 1D integrated curves from different scanning azimuthal directions. 2D WAXS patterns (left) reveal that IC/PEO is isotropic. Corresponding 1D integrated curves from different scanning azimuthal directions (right) show constant intensities for peak a (100), b (110), d (210), and e (300) belonging to IC crystallite and peak c (120) and f (032) attributed to PEO crystallites, indicating that the IC/PEO structure is isotropic with crystallites oriented randomly; 2D WAXS of (b) PEO and (c) drawing-400% PEO (400% elongation). After cold-drawn, the PEO patterns became anisotropic, which are constant with anisotropic patterns of SCTF; and (d) 2D WAXS patterns of dry pc-SCTF returned to isotropic.

FIG. 10 depicts the stability and morphology comparison between drawn PEO, α-CD/PEO and SCTF. (a) pc drawing-400% PEO film dissolved immediately within 10 s when wetted; (b) pc drawing-400% α-CD/PEO film gradually dissolved within 1 day in PBS at room temperature; (c) pc-SCTF-400% was stable in PBS at room temperature over 2 weeks without collapse; and (d) Drawing-400% PEO and drawing-400% α-CD/PEO film are semitransparent while SCTF is white (inset photographs). The SEM results show that SCTF was porous which were not observed in drawing-400% PEO and drawing-400% α-CD/PEO films. Scale bars: (a-c) 1 cm; and (d) 1 μm.

FIG. 11 depicts the formation mechanism of SCTF's porous microstructure. (a) SEM images of PEO, α-CD/PEO and IC/PEO. The platelet stacking structure in IC/PEO thin film was not observed in PEO and α-CD/PEO; (b) pc-drawing-400% PEO film dissolved immediately within 10 s when wetted. Diluting and washing IC/PEO mixture (the mixture for solvent casting) produced a suspension with insoluble precipitates; (c) SEM images show that the precipitates have a platelet structure. Left: SEM image of IC platelets casted on silicon wafer substrate. Right: SEM image of freeze-dried IC platelets; (d) 1D WAXS curve of IC platelets indicates that it has typical channel type PEG-α-CD IC crystalline structure; and (e) Proposed schematic illustration of the porous microstructure formation mechanisms of SCTF. IC crystalline platelets were formed and surrounded by PEO domains in IC/PEO thin film. When applied with uniaxial cold-drawing, PEO domains undergo plastic deformation to form aligned fibrillar bridges and porous structure. Simultaneously, the PEO crystallites and chains in this domain become oriented, which are fixed by PEO crystallite. When wetted or under high humidity, water penetrates this domain, dissolving the PEO crystallites, causing the contraction. Scale bar: (a,c) 1 μm; and (b) 1 cm.

FIG. 12 depicts the MD simulations of the interactions between IC/PEO, PEO/PEO, α-CD/PEO in aqueous solution. (a-b) MD simulation of the aggregation of (a) PEO-PEO and (b) α-CD-PEO, respectively, in aqueous solution. Water is not shown for clarity; (c) Radius of gyration of PEO around IC increased while that of pure PEO remained constant; (d-f) Hydrogen bonds formation during aggregation of IC-PEO, PEO-PEO, and α-CD-PEO, respectively, in MD simulations; (g-f) Interaction energy change during aggregation of PEO-PEO, α-CD-PEO and IC-PEO, respectively, in MD simulations. Illustration of the interaction change in the aggregation of two molecules, the interaction energy incudes both Van der Waals and coulomb interactions (g); and (h) Time evolution of the interaction energy change. Solid line represents the average from 60-100 ns, with the value corresponding to FIG. 7*j*.

FIG. 13 depicts the supercontractile electronics (SCe) for in vivo peripheral nerve stimulation and intramuscular signal recording. (a) Schematic (top) and photograph (bottom) of a free-standing flexible SCe, where SCTF-Au serves as multi-array electrode contacts and interconnects, styrene-ethylene/butylene-styrene (SEBS) as top and intermediate insulation layers and SCTF as supercontractile substrate; (b) Optical microscope image shows that Au formed a continuous mesh consisting of wrinkled micro-ribbons on pc-SCTF. Inset: SEM image of the wrinkled Au ribbon; (c) Longitudinal sectional SEM image shows that spin-coated SEBS penetrated the porous SCTF to form a seamless mechanical interlocking; (d) EIS spectra show that the impedance and phase angle of SCe changed slightly at 0%, 20% and 40% strain. All samples had the same exposed electrode area (2.6 $mm^2$) in PBS. Solid plots: impedance; and hollow plots: phase angle; (e) Schematic of using SCe as shape-adaptive tissue-electronic interface for in vivo stimulation and recording; (f) Photographs show that SCe looped around the common peroneal nerve contracted and formed a conformable wrap within 2 min when wetted; (g) Toe movement of rat induced by common peroneal nerve stimulation using SCe; (h-i) Schemes and photographs show that SCe electrode wrapped conformably around the ELD muscle after wetting (h) while Au-elastomer electrode formed gaps (white arrow) between the electrode and muscle (i); (j) Artificial stimulating signals and evoked compound muscle action potential (CMAP) signals recorded by SCe and Au-elastomer electrode; and (k) Compared with signals recorded by Au-elastomer electrode, those recorded by SCe have lower base noise. Scale bar: (a) 5 mm; (b) 20 μm, inset: 500 nm; (c) 5 μm; (f, h-i) 1 mm; and (g) 1 cm.

FIG. 14 depicts the fabrication process of SCe.

FIG. 15 depicts the SCe for in vivo stimulation and recording. (a) Photographs of as-deposited SCTF-Au with size of 20.0 mm (length)×3.4 mm (width). After wetted, the size changed to 11.3 mm (length)×6.1 mm (width), while the resistance changed from 7.5Ω to 10.8Ω; (b) Optical microscope images of Au on IC/PEO thin film. After wetted, IC/PEO thin film isotropically swelled. The Au film on it was torn apart into discrete domains and lost its continuity and conductivity; (c) Optical microscope images of Au film on SCTF-400%. After wetted, SCTF contracted along the drawing direction and expanded in the transverse direction. The Au film on it became a continuous mesh constructed by wrinkled micron-sized ribbons; (d) SEM images of Au film on pc-SCTF-Au. Cracks and wrinkles were observed but the whole film maintained its continuity; (e) Resistance changes of pc-SCTF-Au under strain. Resistance slightly increased from ~11Ω to ~13Ω when it underwent strain of 40%, indicating that pc-SCTF-Au film is stretchable; (f) Optical microscope image of SEBS layer of pc-SCTF-SEBS. After contraction, wrinkles formed on the SEBS layer; (g) Waterproof backing and cover for SCe to prevent premature contraction before installation; (h) Stepwise schematic illustrating the implementation process of SCe on a peripheral nerve; (i) Size difference of sciatic nerve and common peroneal nerve in a rat; and (j) Water-induced contraction of SCe on the sciatic nerve to form conformable wrap within 2 min. Scale bar: (a) 1 cm; (b-c) 20 μm; (d) left: 100 μm; and right 10 μm; (f) 100 μm; (g) 5 mm; (i) 2 mm; and (j) 1 mm.

FIG. 16 depicts the supercontractile thin films after ethylene oxide (EtO) sterilization.

FIG. 17 depicts the voltage transient experiments of (a) SCe, and (b) Au-elastomer electrode. The maximum negative potential excursion (Emc) and maximum positive potential excursion (Ema) can be recorded. The charge injection capacity (CIC) is the maximum charge delivered to make sure Emc and Ema are within the water electrolysis window (e.g. −0.6 V-0.8V for gold electrode).

FIG. 18 depicts the in vitro stability of SCe array. (a-b) Impedance stability of SCe array under cyclic stretching to 40% strain. The EIS spectra (a) and impedance at 1 kHz (b) show that the impedance of SCe array remained constant, which was around 600Ω for 1 SCe electrode array soaked in PBS solution for 336 hours; and EIS spectra (c) and impedance at 1 kHz (d) show that the impedance of SCe array had little change when soaked in PBS for 336 hours.

FIG. 19 depicts in vivo biocompatibility. (a) Hematoxylin and Eosin (H&E) staining; (b) CD68 immunofluorescence staining; and (c) mean fluorescence intensity and comparison. n=3 independent rats, ***$P<0.001$, NS (not significant), $P>0.05$. The P values of CD68 fluorescence intensity are as follows: for Au-elastomer electrode versus sham control, P=0.00033; for WRAP electrode versus sham control, P=0.60; and for WRAP electrode versus Au-elastomer electrode, P=0.00066. Scale bar: 50 μm.

DESCRIPTION

Figure 1:
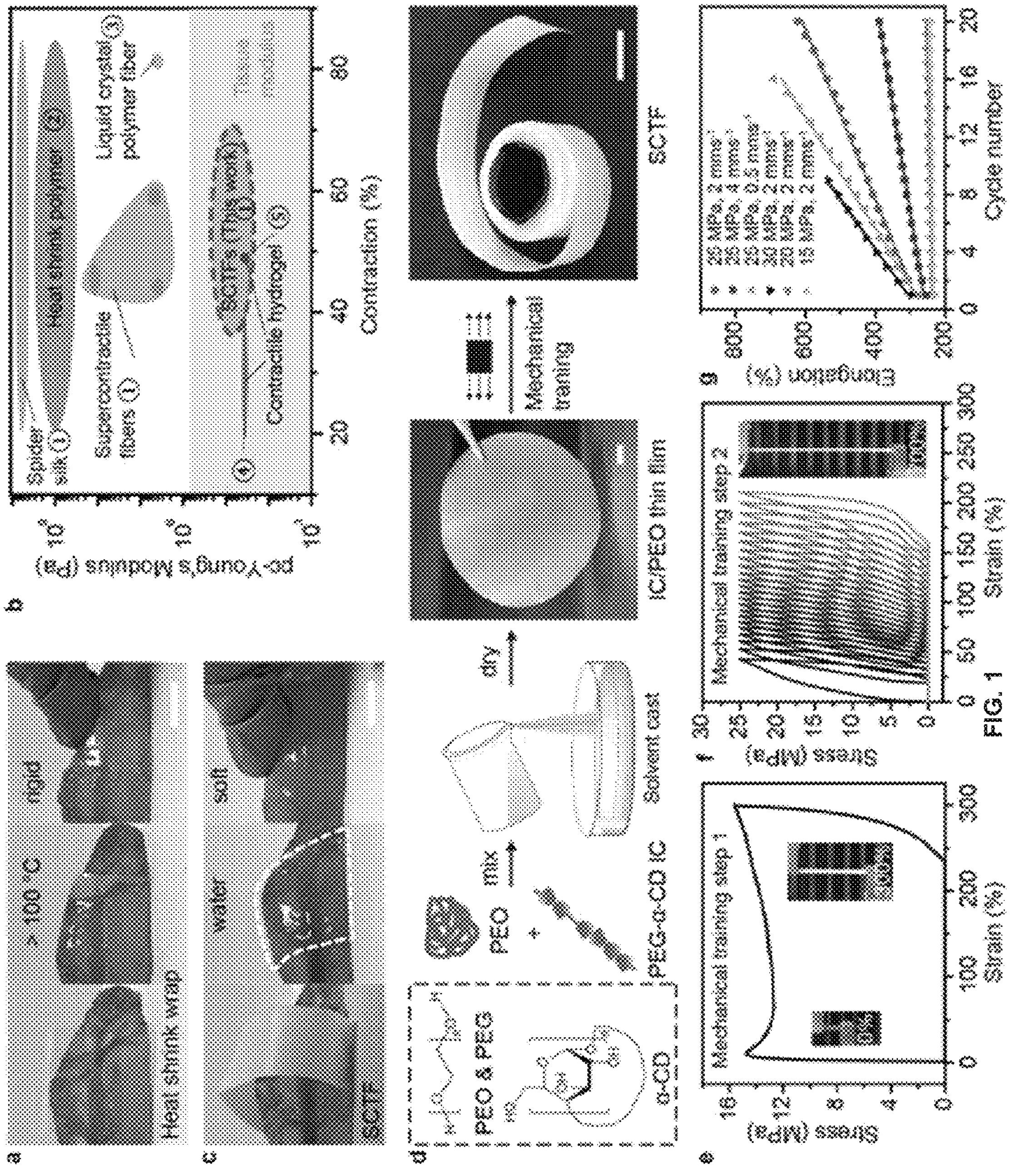

The current invention seeks to overcome some or all of the problems identified above. For example, conventional heat shrink polymer can rapidly contract when heated and therefore are used to package objects with irregular shapes. However, such high-temperature-triggered contraction and their high young's modulus (~GPa) are not suitable for applications related to soft and vulnerable human body. Disclosed herein is a dry, flexible and freestanding super-contractile thin film (SCTF) that rapidly contracts and become a soft and stretchable physical hydrogel thin film when wetted by water. Thus, in a first aspect of the invention, there is provided a supercontractible thin film comprising:

crystalline inclusion complex domains formed from poly (pseudo)rotaxanes or polyrotaxanes; and oriented polyethylene oxide domains physically cross-linked to the crystalline inclusion complex domains, wherein:

the poly(pseudo)rotaxanes or polyrotaxanes are formed from α-cyclodextrin and a polyethylene glycol having a number average molecular weight of from 500 to 10,000 Daltons;

the polyethylene oxide has a number average molecular weight of from 200,000 to 10,000,000 Daltons; and the supercontractible thin film contracts by more than 50% of its original length upon wetting with water.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

The phrase, "consists essentially of" and its pseudonyms may be interpreted herein to refer to a material where minor impurities may be present. For example, the material may be greater than or equal to 90% pure, such as greater than 95% pure, such as greater than 97% pure, such as greater than 99% pure, such as greater than 99.9% pure, such as greater than 99.99% pure, such as greater than 99.999% pure, such as 100% pure.

As used herein, the singular forms "a," "an," and "the" include plural referents unless the context clearly dictates otherwise. Thus, for example, reference to "a composition" includes mixtures of two or more such compositions.

A polyrotaxane is a type of mechanically interlocked molecule consisting of strings and rings, in which multiple rings are threaded onto a molecular axle and prevented from dethreading by two bulky end groups. A poly(pseudo)rotaxane is a similar type of molecule in that it consists of multiple rings threaded onto a molecular axle, but without the two bulky end groups. Both types of molecule may be used herein. In particular examples that may be mentioned herein, the crystalline inclusion complexes may be formed from poly(pseudo)rotaxanes.

In the current invention, the crystalline inclusion complex domains may be formed from α-cyclodextrin and a polyethylene glycol having a number average molecular weight of from 500 to 10,000 Daltons. The polyethylene glycol may be one that has no bulky end groups, thereby providing a poly(pseudo)rotaxane or it may be one that has bulky end groups, thereby providing a polyrotaxane. Each of these inclusion complex domains may then be physically cross-linked to oriented polyethylene oxide domains. This film is a trained film, due at least in part to the orientation of the polyethylene oxide domains, which can undergo contraction by more than 50% of its original length upon wetting with water. For example, if the film has a length of 10 cm before wetting, it may have a length that is less than 5 cm upon wetting.

SCTF possesses aligned, microporous hierarchical structure constructed by IC crystalline domains and oriented PEO domains. It is stable under ambient environment (Temperature<60° C., Relative Humidity<80%) and compatible with conventional planar electronic fabrication processes.

As noted hereinbefore, the film is constructed using α-cyclodextrin, polyethylene glycol and polyethylene oxide, which are all commercially available and non-toxic, showing excellent biocompatibility. In addition, the SCTF and post-contraction (pc) SCTF physical hydrogel is also non-toxic.

The production of the thin film precursor used to make the supercontractible thin film disclosed herein may be accomplished by simply mixing and stirring the ingredients together and can be conducted using only water as a solvent. This thin film precursor can then be transformed into the supercontractible thin film by drawing the thin film under ambient temperature (e.g. by cold-drawing). Thus, the processes used to make the supercontractible thin film may be suitable for use in mass production.

The supercontractible thin film disclosed herein can be prepared with a thickness that is very thin (e.g. having a thickness in the tens of microns). This may make it suitable for use in flexible electronics applications, particularly those requiring the electronics to be in contact with a tissue of a human or animal.

The terms "human" and "animals" include references to mammalian (e.g. human) or non-mammalian subjects. As used herein the terms "subject" are well-recognized in the art, and, are used interchangeably herein to refer to a mammal, including dog, cat, rat, mouse, monkey, cow, horse, goat, sheep, pig, camel, and, most preferably, a human. The term does not denote a particular age or sex. Thus, adult and newborn subjects, whether male or female, are intended to be covered.

The supercontractible thin film disclosed herein displays instant contraction (e.g. ~30%/s) and so displays a spider-silk-like supercontraction. The wet post-contraction (pc) supercontractible thin film becomes a soft and stretchable biocompatible hydrogel thin film with its Young's modulus dropping by more than three orders of magnitude (e.g. from ~260 MPa to ~80 kPa). This dramatic change in modulus is beneficial because when the supercontractible thin film is in its dry and stiff state it is easy to handle and amenable to electronic fabrication, while its soft and stretchable state interfaces well with tissues after implantation (e.g. as part of an electronic device).

It is noted that both the contraction ratio (i.e. the ratio of contracted length to initial length) and pc-Young's modulus were tunable by elongation ratio (the ratio of the expanded length after drawing to the initial length).

Finally, the supercontractible thin film disclosed herein is stable under ambient environment (Temperature<60° C., Relative Humidity<80%) and has aligned microporous hierarchical structure, facilitating its integration into electronics.

In embodiments of the invention, the supercontractible thin film disclosed herein may be one that has one or both of a microporous structure and aligned fibrillar bridges.

The microporous structure of the supercontractible thin film may be advantageous as it may allow for the introduction of other materials into the film's structure. For example, the microporous structure may allow for an elastomeric material to be integrated into the structure of the supercontractible thin film through any suitable means (e.g. spin coating). Without wishing to be bound by theory, it is believed that the microporous structure enables an elastomeric material to penetrate and adhere to the supercontractible thin film through a mechanical interlock. It is also noted that both the microporous structure and, when present, the fibrillary bridges are only present in the supercontractible thin film of the current invention the dry state, When the film has been subjected to wetting, these structures are absent.

As noted above, the supercontractible thin film contracts by more than 50% of its original length upon wetting with water. In embodiments of the invention, the supercontractible thin film may exhibit a contraction rate relative to its original length of from 10 to 50%/s upon wetting with water. For example, the supercontractible thin film may exhibits a contraction rate relative to its original length of about 30%/s upon wetting with water. This rate of contraction is comparable to spider silk.

Any suitable weight:weight ratio of polyethylene glycol: α-cyclodextrin may be used herein, provided that it provides the properties required by the first aspect of the invention. For example, in embodiments herein, the weight:weight ratio of polyethylene glycol:α-cyclodextrin may be from 1:1 to 1:20, such as from 1:5 to 1:15, such as about 1:10.

Any suitable weight:weight ratio of α-cyclodextrin:polyethylene oxide may be used herein, provided that it provides the properties required by the first aspect of the invention. For example, in embodiments that may be mentioned herein, the weight:weight ratio of α-cyclodextrin:polyethylene oxide may be from 1:1 to 10:1, such as from 2:1 to 5:1, such as about 10:6.

In embodiments of the invention any suitable weight: weight ratio of polyethylene glycol:α-cyclodextrin:polyethylene oxide may be used herein. For example, in embodiments that may be mentioned herein, the weight:weight ratio of polyethylene glycol:α-cyclodextrin:polyethylene oxide may be about 1:10:6.

As noted hereinbefore, the supercontractible thin film may be stable at ambient temperatures and humidities. For example, the supercontractible thin film may be stable at a temperature of less than 60° C. and a relative humidity of less than 80%.

The supercontractible thin film may also be stable in an aqueous environment for period of time, making it useful for use in electronics applied to tissues. For example, the supercontractible thin film may be stable in an aqueous solvent for a period of at least two weeks.

In embodiments of the invention that may be mentioned herein, the poly(pseudo)rotaxanes or polyrotaxanes may be formed from α-cyclodextrin and a polyethylene glycol having a number average molecular weight of from 1,000 to 7,500 Daltons, such as from 1,500 to 5,000 Daltons, such as from 1,750 to 2,500 Daltons, such as about 2,000 Daltons.

For the avoidance of doubt, it is explicitly contemplated that where a number of numerical ranges related to the same feature are cited herein, that the end points for each range are intended to be combined in any order to provide further contemplated (and implicitly disclosed) ranges. Thus, the following a number average molecular weight ranges are explicitly contemplated:

from 500 to 1,000 Daltons, from 500 to 1,500 Daltons, from 500 to 1,750 Daltons, from 500 to 2,000 Daltons, from 500 to 2,500 Daltons, from 500 to 5,000 Daltons, from 500 to 7,500 Daltons, from 500 to 10,000 Daltons;

from 1,000 to 1,500 Daltons, from 1,000 to 1,750 Daltons, from 1,000 to 2,000 Daltons, from 1,000 to 2,500 Daltons, from 1,000 to 5,000 Daltons, from 1,000 to 7,500 Daltons, from 1,000 to 10,000 Daltons;

from 1,500 to 1,750 Daltons, from 1,500 to 2,000 Daltons, from 1,500 to 2,500 Daltons, from 1,500 to 5,000 Daltons, from 1,500 to 7,500 Daltons, from 1,500 to 10,000 Daltons;

from 1,750 to 2,000 Daltons, from 1,750 to 2,500 Daltons, from 1,750 to 5,000 Daltons, from 1,750 to 7,500 Daltons, from 1,750 to 10,000 Daltons;

from 2,000 to 2,500 Daltons, from 2,000 to 5,000 Daltons, from 2,000 to 7,500 Daltons, from 2,000 to 10,000 Daltons;

from 2,500 to 5,000 Daltons, from 2,500 to 7,500 Daltons, from 2,500 to 10,000 Daltons;

from 5,000 to 7,500 Daltons, from 5,000 to 10,000 Daltons; and from 7,500 Daltons to 10,000 Daltons.

In embodiments of the invention that may be mentioned herein, the polyethylene oxide may have a number average molecular weight of from 500,000 to 7,000,000 Daltons, such as from 750,000 to 5,000,000 Daltons, such as from 1,000,000 to 3,000,000 Daltons, such as about 2,000,000 Daltons.

The supercontractible thin film may have any suitable Young's modulus when it is in its dry state. For example, the supercontractible thin film may have a Young's modulus of from 50 MPa to 1 GPa, such as from 200 to 550 MPa, such as from 260 to 500 MPa. However, after wetting, the supercontractible thin film will have a significantly reduced Young's modulus. For example, the supercontractible thin film may have a Young's modulus of from 10 to 500 kPa, such as from 50 to 100 kPa, such as about 80 kPa after wetting with water.

As noted hereinbefore, the supercontractible thin film may have been subjected to longitudinal stretching to provide the oriented polyethylene oxide domains. Any suitable amount of stretching that provides the desired oriented polyethylene oxide domains may have been used. For example, the longitudinal stretching may result in a film having a length that is from 218 to 700% of the original length of a freestanding thin film material comprising:

crystalline inclusion complex domains formed from polyrotaxanes or poly(pseudo)rotaxanes; and unoriented polyethylene oxide domains physically crosslinked to the crystalline inclusion complex domains.

In embodiments of the invention that may be mentioned herein, the supercontractible thin film may contract by from 35 to 65% of its original length upon wetting with water.

The supercontractible thin films mentioned herein may conveniently be formed using simple materials and in an environmentally-friendly way, without the need to use organic solvents or additives. Thus, in a second aspect of the invention, there is provided a method of forming a supercontractible thin film as described herein, the method comprising the steps of:

(ai) providing a freestanding thin film comprising:

a crystalline inclusion complex domains formed from polyrotaxanes or poly(pseudo)rotaxanes; and unoriented polyethylene oxide domains physically crosslinked to the crystalline inclusion complex domains, wherein:

the polyrotaxanes or poly(pseudo)rotaxanes are formed from α-cyclodextrin and a polyethylene glycol having a number average molecular weight of from 500 to 10,000 Daltons; and the polyethylene oxide has a number average molecular weight of from 200,000 to 10,000,000 Daltons; and (aii) drawing a film by applying a strain to achieve an elongation of the film of from 100% to 300% of its original length to provide the supercontractible thin film.

As will be appreciated, the freestanding film may be the same chemically to the supercontractible thin film, apart from the orientation of the polyethylene oxide molecular chains, which results in the contractile properties and may make the film microporous, optionally with fibrillar bridges. While a single drawing step may be suitable to generate the supercontractible thin film, this may be enhanced by the use of a repeated drawing step that may make use of different (and progressively longer) drawing steps. Thus, in embodiments of the invention, the method may further comprise further repeatedly drawing the supercontractible thin film by applying a strain to obtain a desired length. Examples of suitable desired lengths may include, but are not limited to values of from 218 to 700% of the original length of the freestanding film.

Any suitable level of strain may be used herein (e.g. the strain used to provide the desired length). In embodiments of the invention, the strain may be from 10 to 60 MPa, such as about 25 MPa.

The drawing speed may be selected to suit the material being stretched, and the level of strain applied. This may be selected by a skilled operator. Examples of suitable drawing speeds for drawing include, but are not limited to, of from 0.1 to 5 mm/s, such as about 2 mm/s.

As noted above, the polyrotaxanes or poly(pseudo)rotaxanes may be formed from α-cyclodextrin and a polyethylene glycol having a number average molecular weight of from 1,000 to 7,500 Daltons, such as from 1,500 to 5,000 Daltons, such as from 1,750 to 2,500 Daltons, such as about 2,000 Daltons. Additionally or alternatively, the polyethylene oxide may have a number average molecular weight of from 500,000 to 7,000,000 Daltons, such as from 750,000 to 5,000,000 Daltons, such as from 1,000,000 to 3,000,000 Daltons, such as about 2,000,000 Daltons.

In the method disclosed above, the method may further comprise:

(bi) providing a composition comprising α-cyclodextrin-poly(ethylene glycol) inclusion complex and a solvent; and (bii) adding poly(ethylene oxide) (PEO) to the composition and aging for a period of time at a temperature of from 40 to 80° C., such as about 60° C. composition to provide a freestanding film precursor solution; and (biii) drying the freestanding film precursor solution to provide the freestanding film precursor.

As noted hereinbefore, the supercontractible thin film may be useful in shape-adaptive electronics. Thus, in a further aspect of the invention, there is provided a shape-adaptive supercontractile electrode comprising:

a first layer of a supercontractible thin film as described herein as a substrate;

an electrode composite material comprising:

a second layer of supercontractible thin film as described herein as an electrode support layer; and a conductive metal compound layer or, more particularly, a metal layer arranged to form electrodes and attached to the second supercontractible thin film layer;

a first insulation layer sandwiched between the first supercontractible thin film layer and the electrode composite material; and a second insulation layer on laid on top of the electrode composite material, wherein the first and second insulation layers are formed from an insulative polymeric material.

The shape-adaptive supercontractile electrode may be as depicted in FIG. 13*a*. In this embodiment, the shape-adaptive supercontractile electrode 100 includes a a first layer of a supercontractible thin film 110 as described herein as a substrate;

an electrode composite material 120 comprising:

a second layer of supercontractible thin film 125 as described herein as an electrode support layer; and a conductive metal compound layer or, more particularly, a metal layer 127 arranged to form electrodes and attached to the second supercontractible thin film layer 125;

a first insulation layer 130 sandwiched between the first supercontractible thin film layer 110 and the electrode composite material 120; and a second insulation layer 140 on laid on top of the electrode composite material 120, wherein the first 130 and second 140 insulation layers are formed from an insulative polymeric material.

The first layer of supercontractible thin film may help to provide the shape-adaptive supercontractile electrode with its contractible properties, while also making the electrode easier to handle when in a dry state.

In addition, it is noted that the supercontractible thin film also helps the electrode maintain conductivity when it is wetted. Conventional dry hydrogels lose their conductivity when wetted because these hydrogels undergo isotropic swelling that tears the conventional (e.g. Au) films into discontinuous, isolated domains. In contrast, the use of Au (or other suitable metals) on the supercontractible thin films disclosed herein to provide a suitable electrode material will maintain its conductivity, as well as becoming stretchable because the supercontractible thin film contracts along the drawing direction and expands in the transverse direction.

Thus, the electrodes disclosed herein can change their shape and size according to the target tissues and organs when wetted to achieve comfortable wrapping. This can provide applications in nerve stimulation and electrophysiological signal recording.

Any suitable insulative polymeric material may be used herein. For example, the insulative polymeric material may be selected from PDMS or a thermoplastic elastomer. In particular examples mentioned herein, the thermoplastic elastomer is a self-healing thermoplastic elastomer. In particular embodiments of the invention, the insulative polymeric material may be styrene-ethylene/butylene-styrene, which is a self-healing thermoplastic elastomer. As noted, the shape-adaptive supercontractile electrode makes use of two insulative polymer material layers.

If a metal layer is present in the shape-adaptive supercontractile electrode, the metal may be any suitable metal that provides good conductivity and ductility. Examples of suitable metals that may be mentioned herein include, but are not limited to, platinum and, more particularly, gold, silver, and copper, and combinations thereof. If a conductive metal compound layer is present in the shape-adaptive supercontractile electrode, the conductive metal compound may be selected from any suitable conductive metal compound. For example, the conductive metal compound may be selected from one or both of iridium oxide and titanium nitride The electrode composite material may be patterned in any suitable manner. For example, the electrode composite material may have multiple parallel electrode wires or it may have any suitable shape that is desired. The design of the electrode composite material is not limited to any particular configuration and may be designed based on the needs of the desired application.

In embodiments of the invention, the electrode composite material may further comprise a layer of an insulative polymeric material on top of the conductive metal compound layer or, more particularly, the metal layer. As before, this insulative polymeric material may be selected from PDMS or a thermoplastic elastomer. For example, this insulative polymeric material may be a thermoplastic elastomer that is a self-healing thermoplastic elastomer (e.g. styrene-ethylene/butylene-styrene).

The shape-adaptive supercontractile electrode may be formed using simple technology. Thus, in a further aspect of the invention, there is provided a method of forming an electrode composite material, the method comprising:

(ci) providing a supercontractible thin film as described herein as a substrate; and (cii) depositing a conductive metal compound or, more particularly, a metal by thermal deposition onto the supercontractible thin film substrate to form a conductive metal compound layer or, more particularly, a metal layer.

In embodiments of the method, the deposition rate of the conductive metal compound or, more particularly, the metal may be any suitable deposition rate. For example, the deposition rate of the conductive metal compound or, more particularly, the metal may be selected to avoid contraction of the supercontractible thin film during the deposition process. In particular examples that may be mentioned herein the deposition rate of the conductive metal compound or, more particularly, the metal may be from 0.1 to 0.5 Å/s, such as about 0.3 Å/s.

As will be appreciated, the deposition process may be conducted in a vacuum. For example, the vacuum may be less than or equal to about $2\times10^{-6}$ Torr.

The wherein the conductive metal compound layer or, more particularly, the metal layer is deposited in a desired pattern on the substrate. This may be any desirable pattern on the substrate. The patterning may be achieved through the use of a mask layer applied to the surface of the substrate and which mask layer can then be removed before the next steps As above, if there is a metal layer is present, then the metal may be selected from one or more of platinum and, more particularly, gold, silver, and copper. If a conductive metal compound layer is present then the conductive metal compound may be selected from one or both of iridium oxide and titanium nitride.

The method may further comprise attaching conductive leads to the conductive metal compound layer or, more particularly, the metal layer. Any suitable means of attaching the conductive leads may be used. For example, the conductive leads may be attached by way of a conductive adhesive.

In embodiments of the invention, the supercontractible thin film of the electrode may have a first surface on which the conductive metal compound layer or, more particularly, the metal layer is deposited and a second surface that has no deposition of a conductive metal compound or, more particularly, a metal on it. The method may further comprise the step of attaching an insulative polymeric material onto the first surface of the supercontractible thin film of the electrode to provide an insulated electrode block. This attachment may be conducted by any suitable means. For example, the insulative polymeric material may be attached by spin coating.

In embodiments that may be mentioned herein, the insulated electrode block may comprise areas patterned with the conductive metal compound layer or, more particularly, the metal layer and areas that do not contain the layers and the method further comprises substantially removing the areas that not contain the layers to form a patterned electrode. This may be achieved by any suitable manner, such as described hereinbelow in the examples. In such embodiments, the method disclosed herein may further comprise the steps of:

(di) providing a substrate layer formed from a layer of supercontractible thin film as described herein and a first layer of an insulative polymeric material; and (dii) laying the patterned electrode on the first insulative polymeric material layer and encapsulating the patterned electrode by the deposition of a second layer of the insulative polymeric material onto the patterned electrode on the first insulative polymeric material layer, optionally wherein the second insulative polymeric material layer is formed by spin coating.

The insulative polymeric material may be as described hereinbefore.

As will be appreciated, the supercontractible thin film layer may be used to form a supercontractile electronic device. Thus, in a further aspect of the invention there is provided a supercontractile electronic device comprising a supercontractible thin film layer as described herein. In yet a further aspect of the invention, there is provided a supercontractile electronic device comprising a shape-adaptive supercontractile as described herein.

Supercontractile electronics can be used as implantable electrodes to treat diseases such as epilepsy, Parkinson's, depression, arrhythmia and as machine-human interfaces. With further optimizing, more sophisticated shape-adaptive electronics with added functionalities such as pressure sensing and drug delivery can be realized. Such novel water shrink films as those disclosed herein might replace conventional heat shrink film in applications that cannot tolerate a high temperature. They can also be applied in other biomedical areas where shape-adaptive wrap or specific compression is needed. Other smart biomedical devices for applications like wound closure, scar and stretch mark reduction and vascular and nerve repair can be developed based on the disclosed water shrink material too.

Aspects and embodiments of the invention will now be discussed by reference to the following non-limiting examples.

EXAMPLES

Materials

PEG (Mw=~2,000), PEO (Mw=~2,000,000), PBS, NaCl, KCl, $KNO_3$, $K_2SO_4$, and α-CD were purchased from Sigma-Aldrich. LIVE/DEAD® Viability/Cytotoxicity Kit for mammalian cells was purchased from Invitrogen™. DMEM (Gibco™) was purchased from Thermal Fisher. SEBS (Tuftec™ H) was purchased from Asahi Kasei. H&E and Anti-CD68 staining kits were purchased from Guangzhou Kaixiu and Servicebio, respectively.

General Procedure for Capturing Optical Images

Optical images of Au film and SEBS were captured using Zeiss Axio Scope A1.

General Procedure for MD Simulation

All-atom MD simulations based on the GROMACS package (Hess, B. et al., *J. Chem. Theory Comput.* 2008, 4, 435-447) were performed to investigate the molecular interactions between PEO and PEO, α-CD and PEO, IC and PEO respectively in solution. Due to the limitation of computation capability, relatively short polyethylene glycol (H—[O—CH2-CH2]n-OH) molecular models were adopted in simulations compared to those used in experiments. Short length (n=9, 14) and long length (n=49) polymers were chosen to represent PEG and PEO, respectively, in the experiments. Automated Topology Builder (ATB) was employed to generate the topologies and parameters of α-CD, PEG (n=9, 14) that were compatible with the GROMOS54a7 force field (Malde, A. K. et al., *J. Chem. Theory Comput.* 2011, 7, 4026-4037; and Stroet, M. et al., *J. Chem. Theory Comput.* 2018, 14, 5834-5845) which has been widely used in the study of PEG polymer and small organic molecules. PEO was constructed based on the parameters of PEG by repeating the center units. VMD57 was used to visualize the snapshots in MD simulations. α-CD is depicted as an isosurface extracted from a volumetric Gaussian density map computed from atoms. PEG and PEO polymers are represented as spheres with chains. Water molecules are not shown for clarity. For enhanced computational efficiency, water molecules were represented by a polarization corrected simple point-charge SPC/E model (Berendsen, H. J. C., Grigera, J. R. & Straatsma, T. P., *J. Phys. Chem.* 1987, 91, 6269-6271). The fast smooth particle-mesh Ewald (Essmann, U. et al., *J. Chem. Phys.* 1995, 103, 8577-8593) was used to calculate the long-rang electrostatic interactions. The system was modelled as an NPT ensemble, with periodic boundary conditions in all directions under constant pressure P (1 atm) and constant temperature T (300 K). The time step was fixed at 2 fs. In the simulation of formation of IC in solution, PEG with n=7 and 3 α-CD were randomly placed in the water box of size 4×4×4 nm and then relaxed to run 500 ns. In the simulation of stability of crystalline IC, 16 ICs (each with one PEG (n=14) and 7 α-CD) constructed based on the experimental structure (Sakai, Y. et al., *J. Phys.* Condens. Matter 2011, 23, 284108) were placed in the water box of size 8×8×8 nm, and then the system was relaxed to run 100 ns simulation. In the simulation of interactions between PEO and PEO, α-CD and PEO, IC and PEO were placed in the water box of 8.0×8.0×8.0 nm, and the systems were relaxed to 100 ns.

Example 1. Preparation of SCTFs

Figure 2:
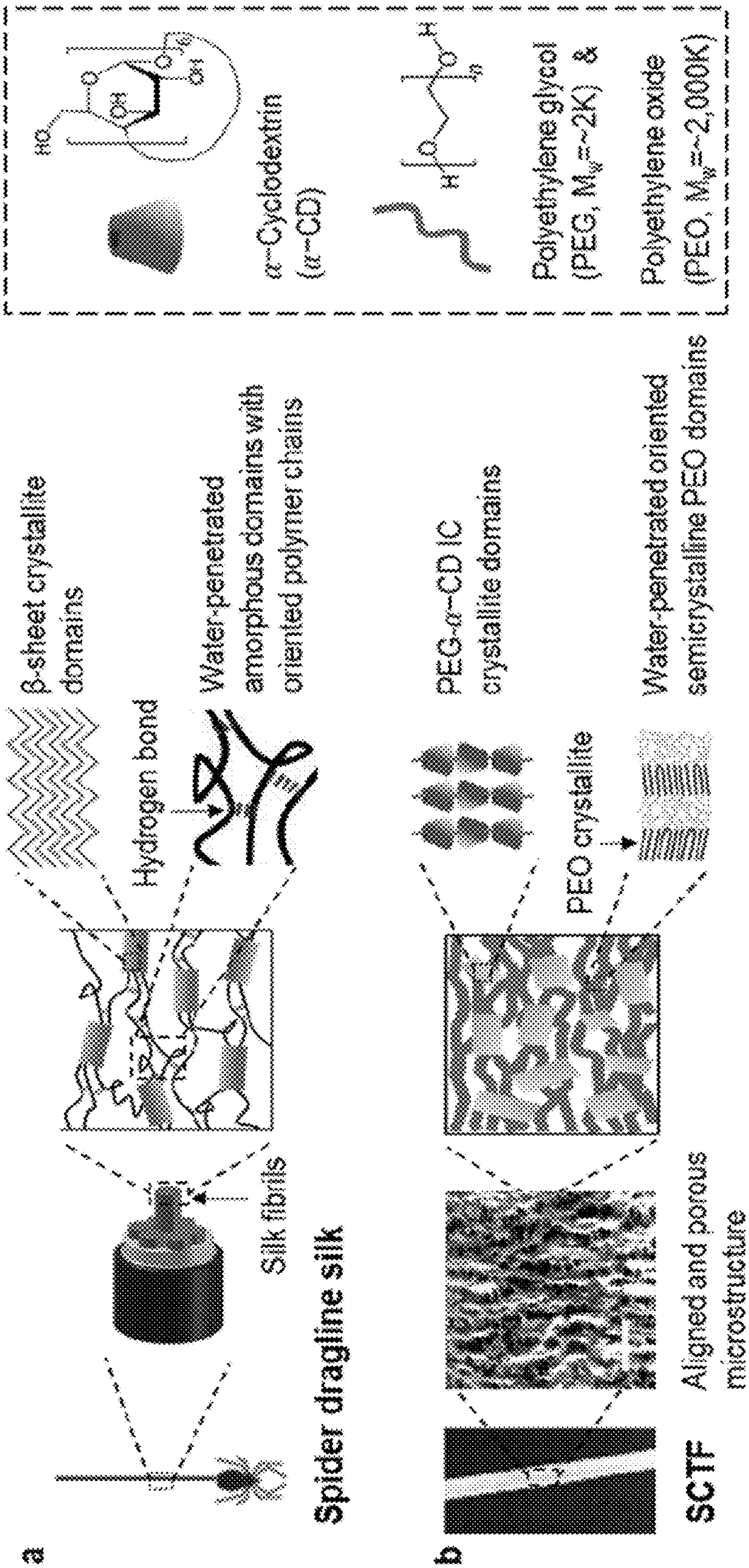

Here, we report a dry, flexible and freestanding supercontractile thin film (SCTF) that rapidly contracts and softens when wetted (FIG. 1*c*). Inspired by spider-silk, we constructed SCTF by orienting water-soluble PEO domains crosslinked by α-CD-PEG IC crystalline domains (FIG. 2*b*).

We prepared SCTFs in two steps: (1) fabrication of free-standing IC/PEO thin films; and (2) mechanical training of the IC/PEO thin films by repeated cold drawing (FIG. 1*d*).

Fabrication of Free-Standing IC/PEO Thin Films

Figure 3A:
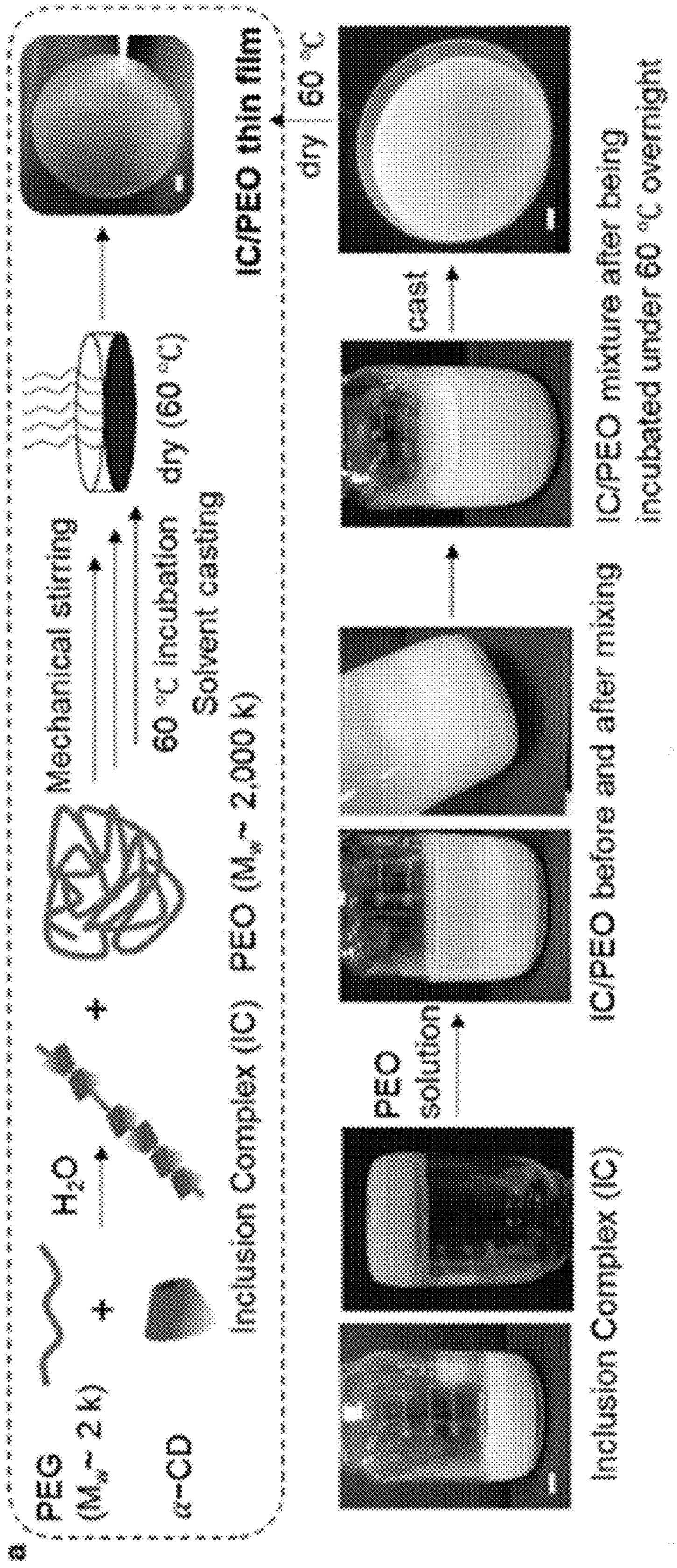

PEG (1 g, Mw~2,000) was dissolved in deionized $H_2O$ (50 mL). α-CD (10 g) was then slowly added into the PEG solution under 60° C. ultrasonic water bath. After being incubated in the 60° C. ultrasonic water bath for 1 min, the white mixture was cooled down to room temperature to yield the PEG-α-CD IC as a white gel (FIG. 3*a*). Then, PEO aqueous solution (150 ml, 4 wt %) was mixed with the white IC gel through mechanically stirring for 10 min to get a thick mixture. Next, the mixture in a sealed glass bottle was incubated at 60° C. overnight. This process can remove the inner air bubbles. Then, the bubbles on the surface of the mixture was gently removed. Finally, the mixture was casted on petri dishes and dried at 60° C. overnight to evaporate the $H_2O$. After peeling off from the petri dishes, free standing IC/PEO thin films were obtained, the thickness of which can be tuned by the total amount of casted mixture. Typically, 9 g mixture casted on a petri dish with diameter of 90 mm can get a thin film with thickness about 90 μm.

The optimal mass ratio of PEG:α-CD:PEO is 1:10:6. The other mass ratios include 1:1 to 1:20 for PEG:α-CD, and 1:1 to 10:1 for α-CD:PEO.

The optimal molecular weight of PEG and PEO are PEG=2,000 and PEO=2,000,000. Oher molecular weight of PEG and PEO are PEG=500 to 10000 and PEO=20,0000 to 10,000,000.

Then, we mechanical-trained (Matsuda, T. et al., *Science* 2019, 363, 504; and Lin, S. et al., *Proc. Natl. Acad. Sci. U.S.A.* 2019, 116, 10244) the IC/PEO thin films through repeated cold drawing (FIG. 1*d*). The mechanical training includes two steps.

Mechanical Training Process

The two-step mechanical training process was conducted using mechanical tester (C42, MTS Systems Corporation) at room temperature. IC/PEO thin films prepared above were cut into pieces with rectangle geometry. First, a IC/PEO thin film was yielded with a deformation rate of 2 $mms^{-1}$ to 300% strain (to avoid film breakage). Second, the yielded film was sequentially subjected to repeated drawing after resetting the sample's parameters (post-yield length, width and thickness). For each cycle, the samples were drawn to a maximum stress (25 MPa) and returned to the initial position through unloading at a crosshead speed of 2 $mms^{-1}$. The elongation ratios were calculated as:

$$\text{Elongation} = \frac{L' - L_0}{L_0} \times 100\%,$$

where L' is the post drawn length and $L_0$ is the original length.

The optimal cold drawing preset stress for IC/PEO (mass ratio of PEG:α-CD:PEO=1:10:6) is 25 MPa. The optimal cold drawing speed is 2 mm/s. Other cold drawing preset stresses are from 10 MPa to 60 MPa. Other cold drawing speed include 0.1 mm/s to 5 mm/s.

Mechanical Properties Characterization

All the mechanical tests were performed using mechanical tester (C42, MTS Systems Corporation) with a 50 N load cell. For stain-stress curves of IC/PEO, PEO thin films, samples with sizes of 15 mm (gauge length)×5 mm (width) were tested. The thickness (around 90 μm) of each sample was measured by a thickness gauge. For post-contraction wet hydrogel films, samples with gauge length of 10 mm were tested. The precise post-contraction thickness and width of each sample were measured separately before mechanical tests. All the tests were conducted with a crosshead speed of 2 $mms^{-1}$. The Young's modulus was calculated from the initial slope of stress versus strain curve. For the constrained supercontraction force relaxation test, SCTF-400% with length of 30 mm was tested. The tested length (distance between two grips) was fixed at 18 mm. The whole sample and test grips were placed in a fluid bath chamber. When testing, 37° C. water was pumped into the chamber in which the water level was raised at a speed of ~4.8 mm/s and stopped when the sample was just completely submerged. Then, the measured constrained forces were converted into confining pressure (see FIG. 4).

Figure 4:
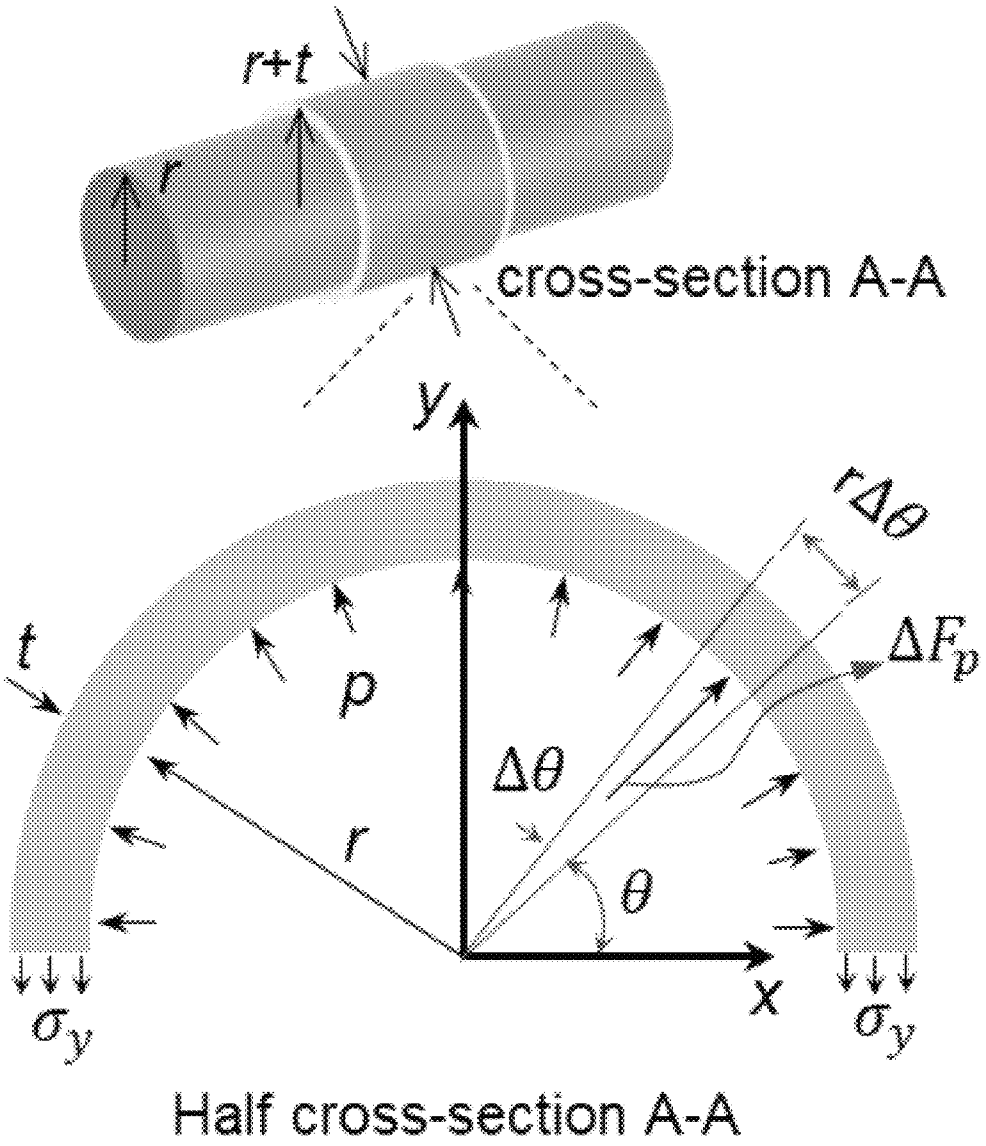

To analyze the compression stress distribution, we took the half of cross section A-A (as shown in FIG. 4) as the target. Due to the symmetry of loading mode and structure, the normal stress $\sigma_y$ is non-zero. With utilization of the force equilibrium in the y direction, the normal stress $\sigma_y$ can be derived. The radial force acting on the inner surface of arc length $r\Delta\theta$ is $$\Delta F_p = p(r\Delta\theta) \tag{1}$$

In the y direction, the component of the radial force is $$\Delta F_y = \Delta F_p \sin\theta = p(r\Delta\theta)\sin\theta \tag{2}$$

With $\Delta\theta \rightarrow 0$, the total force $\Delta F_y$ becomes the integral in the following force-balance equation $$\Delta F_y = \int_0^{\pi} pr\sin\theta d\theta = 2\sigma_y t \tag{3}$$

Integrating equation (3), we have $$2pr = 2\sigma_y t \tag{4}$$

We can rewrite equation (4) to $$p = \frac{\sigma_y t}{r} \tag{5}$$

Because $$\sigma_y = \frac{F}{\mathrm{wt}}$$

and $2\pi r = L$, therefore $$p = \frac{2\pi F}{wL} \tag{6}$$

where F is the constrained contraction force, w and L is the width and length of tested pc-SCTF respectively.

All-Atom MD Simulations

All-atom MD simulations of spontaneous formation of IC in solution was conducted to show this interaction. In this simulation, PEG (H—[O—$CH_2$—$CH_2$]n-OH) with n=9 and 3 α-CD were randomly placed in the a water box of size 4*4*4 nm and then relaxed to run for 500 ns.

Characterisation

We have prepared SCTF by first fabricating a free-standing IC/PEO thin film through simply mixing IC gel formed by host-guest supramolecular interactions (FIG. 3*a-c*) with PEO.

Figure 3B:
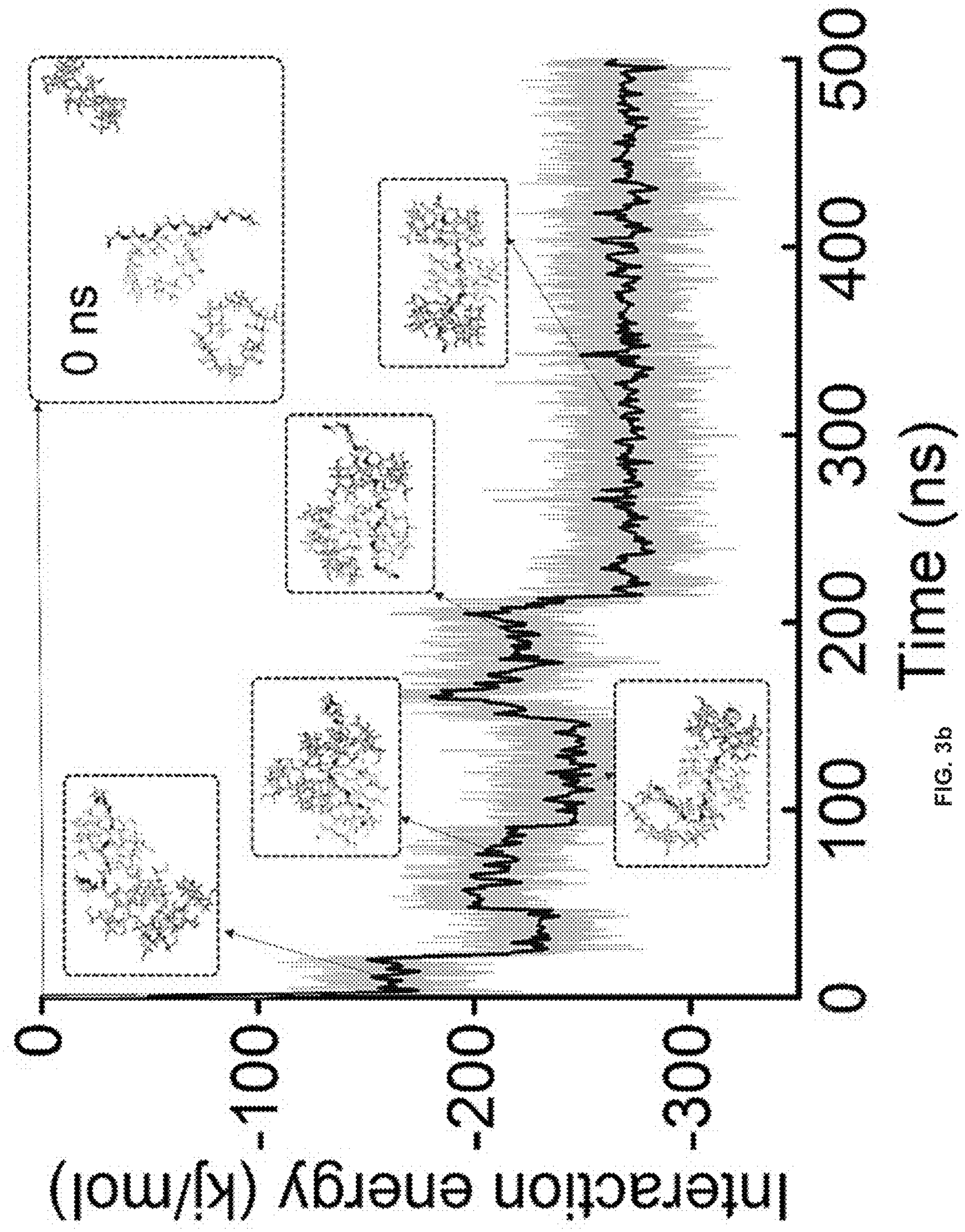

As shown in FIG. 3*b*, α-CD instantly (5 ns) interact with PEG, leading to the thread of one α-CD and the decrease of interaction energy from ~−50 kJ/mol to ~−160 kJ/mol. At 93 ns, two α-CD were threaded by the PEG and the corresponding interaction future decreased to ~−250 kJ/mol. Finally at 215 ns, all three α-CD were threaded to form IC with interaction energy of ~−290 kJ/mol and this IC structure remained stable in long time simulation (FIG. 3*b*). MD simulations of crystalline IC show that IC is stable and maintains the structure after 100 ns simulation in solution (FIG. 3*c*).

Figure 5:
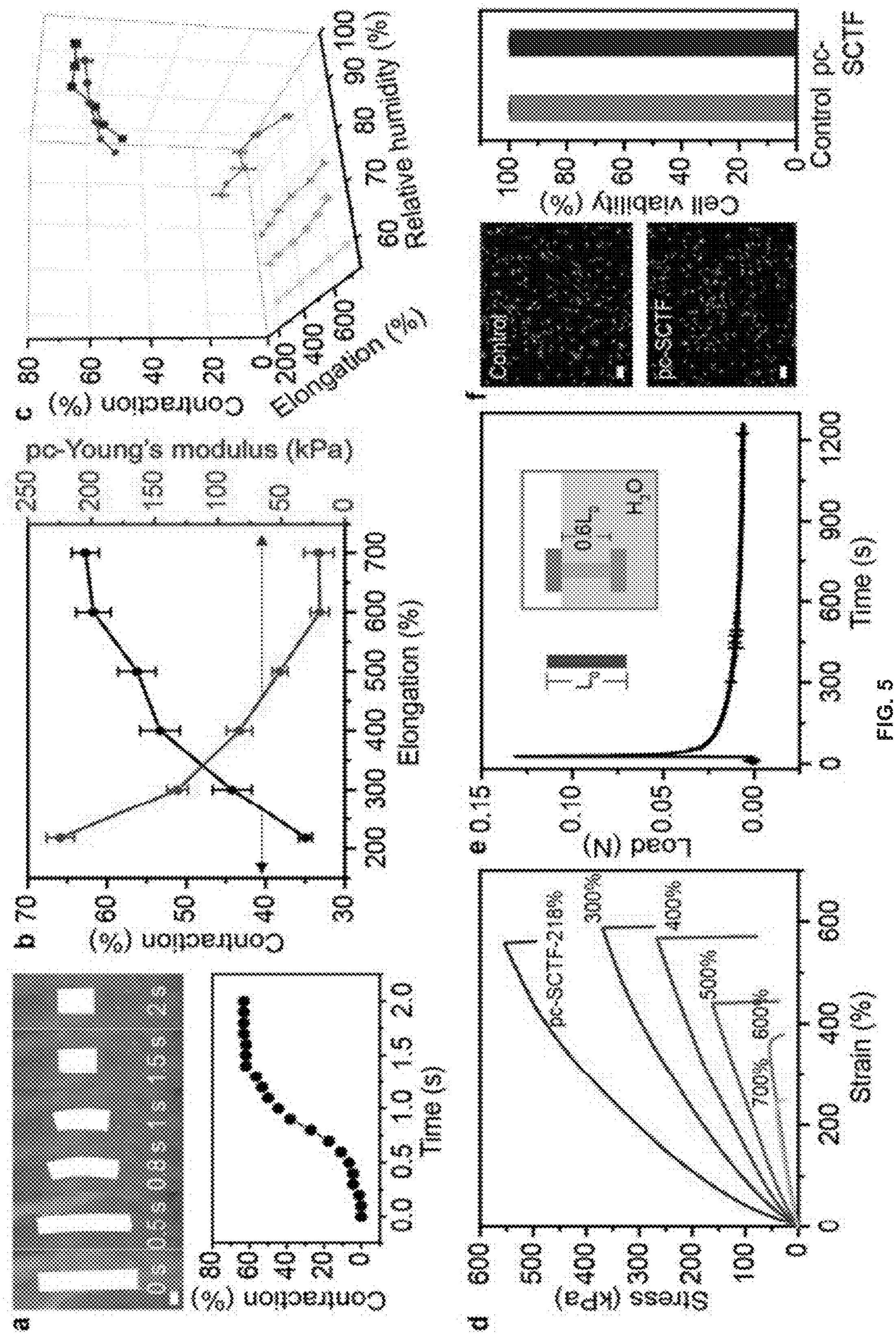

The as-prepared IC/PEO thin film started to yield at 5% and broke at about 400% strain when cold-drawn (FIG. 3*d*). During yielding, necking first appeared where the transparent film became white before spreading along the whole film. Therefore, to get a homogeneous yielded film, we first drew the IC/PEO film to 300% strain (to avoid film breakage), followed by unloading (FIG. 5*d*). Such yielded film had an elongation ratio (the ratio of the expanded length after drawing to the initial length) of ~218%. To obtain films with larger elongation, we then repeatedly drew the yielded film to a preset stress and then returned it to the initial position in each cycle (FIG. 1*f*). During this step, the elongation ratio increased linearly with cycle number. Both preset stress and drawing speed affected the elongation ratio for each cycle, with higher preset stress and lower drawing speed resulting in larger elongation ratios. The optimal preset stress and drawing speed are 25 MPa and 2 $mms^{-1}$, respectively (FIGS. 3*e* and 5*g*). Using this method, we produced SCTFs with elongation ratios ranging from 218% to 700% (FIG. 3*f*).

For the IC/PEO film with mass ratio of PEG:α-CD:PEO=1:10:6, the Young's modulus was around 550 MPa. For dry SCTF prepared by cold-drawn IC/PEO film (1; 10:6), their young's modulus ranged from 500 MPa to 50 MPa. For IC/PEO film with other mass ratios, their Young's modulus ranged from 300 MPa to 1 GPa.

Example 2. Supercontraction and Post-Contraction Properties

We examined the contraction of SCTF by soaking it in water.

Supercontraction and Water Content

The contraction ratio of SCTFs with elongation ratio from 218% to 700% under different relative humidity were measured. SCTFs were cut into rectangles with the size of 10 mm×2 mm, and placed into the sealed bottles with different humidity and an open empty bottle (ambient environment) for 24 h. The relative humidity in each bottle was tuned using saturated salt solutions (Greenspan, L., J. *Res. Natl. Bur. Stand. A. Phys. Chem.* 1977, 81 A, 89-96, KI, NaCl, KCl, $KNO_3$, and $K_2SO_4$) overnight. The RH of each bottle was about 69%, 75%, 84%, 94%, and 97% at 25° C., respectively. The ambient humidity was measured using humidity meter HI 9565 (HANNA Instruments H19565), which was about 60%. Subsequently, the post-contraction length was measured. The contraction ratios were calculated as follows:

$$\text{Contraction ratio} = 1 - \frac{L''}{L}$$

where L" is the post-contraction length and L is the original length.

For contraction ratio after soaking in water and post-contraction water content, SCTFs with elongation ratio from 218% to 700% were cut into samples with a length of 40 mm. The weight of each sample $m_{dry}$ was recorded. Then, each sample was soaked in deionised (DI) water for 1 min to get pc-SCTFs hydrogel film. The post-contraction length L" and weight $m_{wet}$ were measured. The contraction ratios and water content of each sample were calculated as follows:

$$\text{Contraction ratio} = 1 - \frac{L''}{L}$$

$$\text{Water content} = 1 - \frac{m_{dry}}{m_{wet}}$$

where L" is the post-contraction length and L is the original length.

Results and Discussion

Upon wetting, our initially dry SCTF contracted significantly and instantly (~30%/s) (FIG. 5*a*), displaying spider-silk-like supercontraction. The wet pc-SCTF became a soft and stretchable hydrogel thin film with its Young's modulus dropping by more than three orders of magnitude (from ~260 MPa to ~80 kPa). This dramatic change in modulus is beneficial because the dry and stiff state is amenable to electronic fabrication while the soft and stretchable state interfaces well with tissues after implantation. Additionally, both the contraction ratio (the ratio of contracted length to initial length) and pc-Young's modulus were tunable by elongation ratio (FIG. 5*b*). Increasing the elongation ratio from 218% to 700% increased the contraction ratio from ~35% to ~65% and decreased the pc-Young's modulus from ~225 kPa to 20 kPa. Besides, SCTFs did not contract when RH was lower than 80% (FIG. 5*c*). This indicates that they are stable in ambient environment (temperature<60° C., RH in Singapore is ~60%) and are therefore, easy to handle during electronic fabrication and final implantation processes.

Therefore, we have fabricated a SCTF (thickness, tens of microns) using a simple combination of α-CD, PEG and PEO to achieve spider-silk-like supercontraction.

Example 3. Optimal Elongation Ratios of SCTFs for SCe Fabrication

To determine the optimal elongation ratios of SCTFs for SCe fabrication, we further characterized the water content and interfacial impedance in PBS and stretchability of pc-SCTF (prepared in Example 1). The water content was characterized in PBS by following the protocol for supercontraction and water content in Example 2. The supercontraction force generated by the materials was determined by following the protocol for mechanical properties characterization in Example 1.

Electrical and Electrochemical Characterizations

Figure 24:
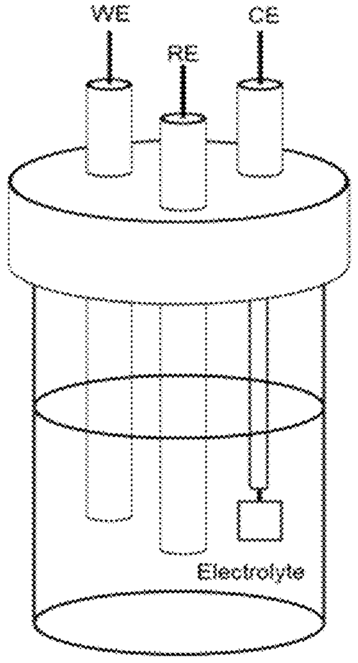
FIG. 24 depicts a three-electrode setup. WE is the working electrode, RE is the reference electrode, and CE is the counter electrode.

All the resistances of samples were measured using Keithley 4200A-SCS parameter analyser. The tested sample size was 3.4 mm×20 mm (before contraction) with the thickness of Au film of 100 nm. For testing resistance change under strain after contraction, MTS mechanical tester was used to give a deformation speed of 0.1 $mms^{-1}$. The ESI experiments were performed using electrochemical working station (ZAHNER ZENNIUM). The setup for testing is a conventional three-electrode setup in PBS buffer at room temperature (FIG. 24), where the test sample was used as the working electrode, Pt was used as the counter electrode and Ag/AgCl was used as the reference electrode. The tests were performed in Bode model in a frequency range from 1 Hz to 100 kHz with a voltage amplitude (Cogan, S. F., *Annu. Rev. Biomed. Eng.* 2008, 10, 275-309) of 10 mV. For post-contraction wet SCTFs, the areas of test samples exposed in PBS were kept at 1.40 $cm^2$. For SCe impedances change under different strain, the exposed electrode areas were kept at 2.6 $mm^2$.

In Vitro Biocompatibility

The in vitro biocompatibility (cytotoxicity) tests were conducted through culturing cell using SCTF-conditional medium. The SCTF-conditional medium was prepared by incubating SCTF-400% (5 mg) which was sterilized via UV light before using, in 5 ml of culture medium (DMEM) at 37° C. for 24 h. Normal human dermal fibroblasts cells were seeded in a petri dish at a density of $1.5\times10^4$ cells per $cm^2$ and incubated for 2 days. After replacement of the cell medium with SCTF-conditional medium and pristine culture medium, the cells were further incubated for 24 h. Cells in pristine culture medium were used as control. Thereafter, cells were stained using reagents in LIVE/DEAD® Viability/Cytotoxicity Kit for mammalian cells. Cell viability was assessed by fluorescence microscope (Nikon ECLIPSE Ti2) under which live cells fluoresce bright green (Ex/Em: ~495 nm/~515 nm), whereas dead cells fluoresce red (Ex/Em: ~495 nm/~635 nm).

Results and Discussion

Figure 6:
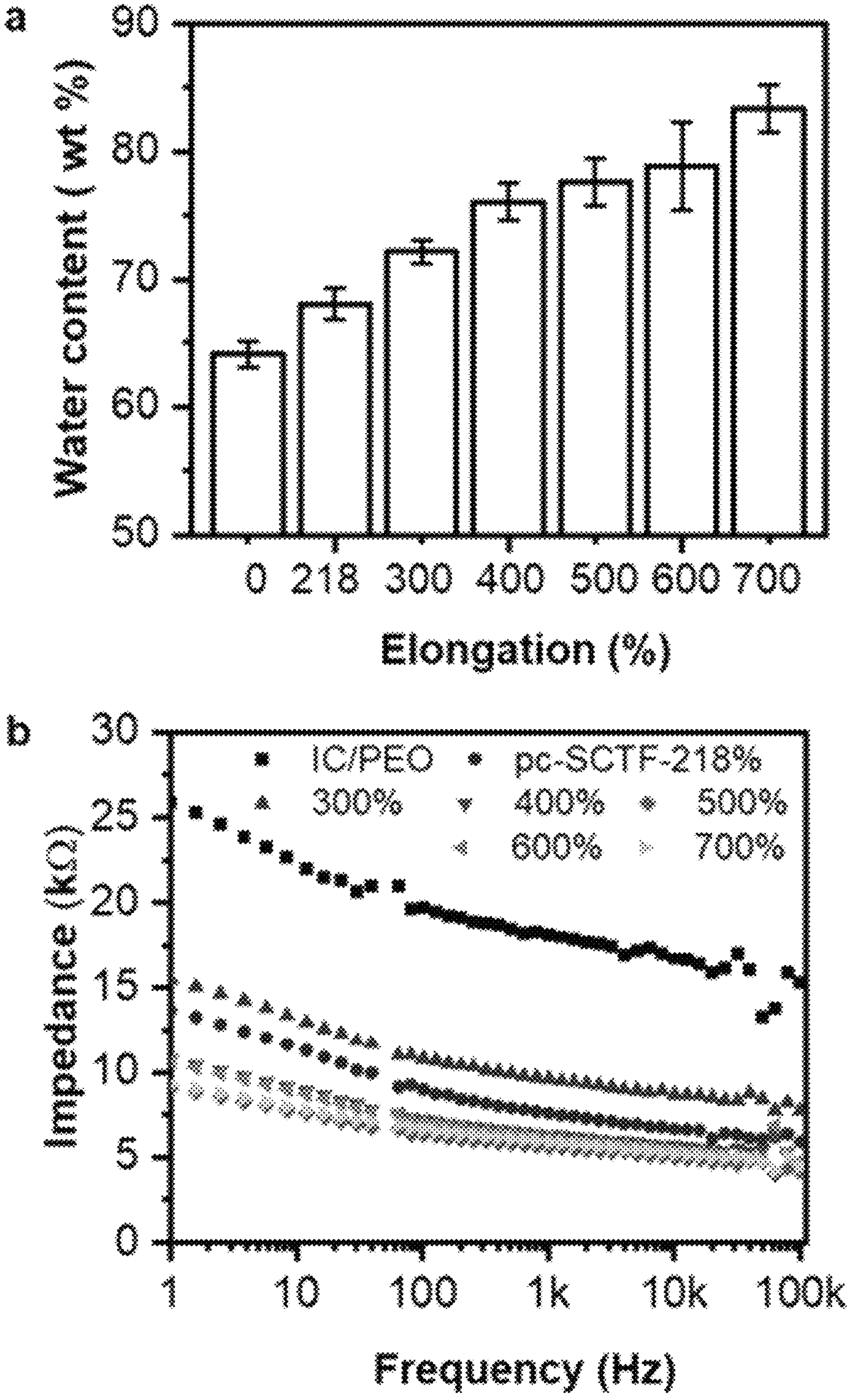

The water content increased, while impedances decreased as elongation ratio increased (FIG. 6). However, for elongation ratios>400%, the decrease in impedance is smaller and the pc-SCTF became less stretchable (FIG. 5*d*). Hence, to fabricate SCe, we used SCTF with an elongation ratio of 400% (SCTF-400%), which has a contraction ratio of >50% and a pc-Young's modulus of <100 kPa, offering good mechanical match with tissues such as peripheral nerves (E, ~100 kPa).

For peripheral nerve applications, the compression generated by wrapping should be below 20 mmHg, above which intraneural blood flow is inhibited. Therefore, we measured the supercontraction force generated by constrained SCTF-400% under water (tested gauge length is ~150% of its pc-length and 60% of its original length) and converted them to confining pressures (FIG. 4). The force generated is transient with 60% decaying within 10 s and only 5% remaining after 20 min (FIG. 5*e*). The corresponding confining pressures were ~18 mmHg and ~2 mmHg, respectively, which are well below the threshold level and indicate that SCTF-400% is safe for peripheral nerve applications. LIVE/DEAD cytotoxicity assay further shows that the pc-SCTF is non-toxic and biocompatible (FIG. 5*f*).

Example 4. Hierarchical Structure of SCTFs

Field Emission Scanning Electron Microscopy (FESEM)

The FESEM images were obtained through JEOL 7600 and JEOL 7800. All samples were observed directly without Au or Pt coating. For JEOL 7600, the acceleration voltage was 5 kV under secondary electron image (SEI) mode, while for JEOL 7800, the acceleration voltage was 1 kV.

Two-Dimensional (2D) Wide-Angle X-Ray Scattering (WAXS) Measurements

The 2D WAXS measurements were performed on NanoinXider system of Xenocs France in transmission mode using radiation source of Kα radiation (λ=0.154 nm) operated at 50 kV and 0.6 mA with a semiconductor detector (Pilatus, Dectris, 100 K). The testing chamber is in a vacuum and the exposure time for each test was 5 min.

TEM

TEM images of IC platelets were recorded on a JEOL 2010F transmission electron microscope (JEOL Ltd, Tokyo, Japan) operating at an acceleration voltage of 200 kV.

Polarized Light Microscopy

Polarized light microscopy images of PEO, α-CD/PEO, and IC/PEO thin films were measured with a Polarizing Microscope (OLYMPUS BX53-P).

Results and Discussion

Figure 7:
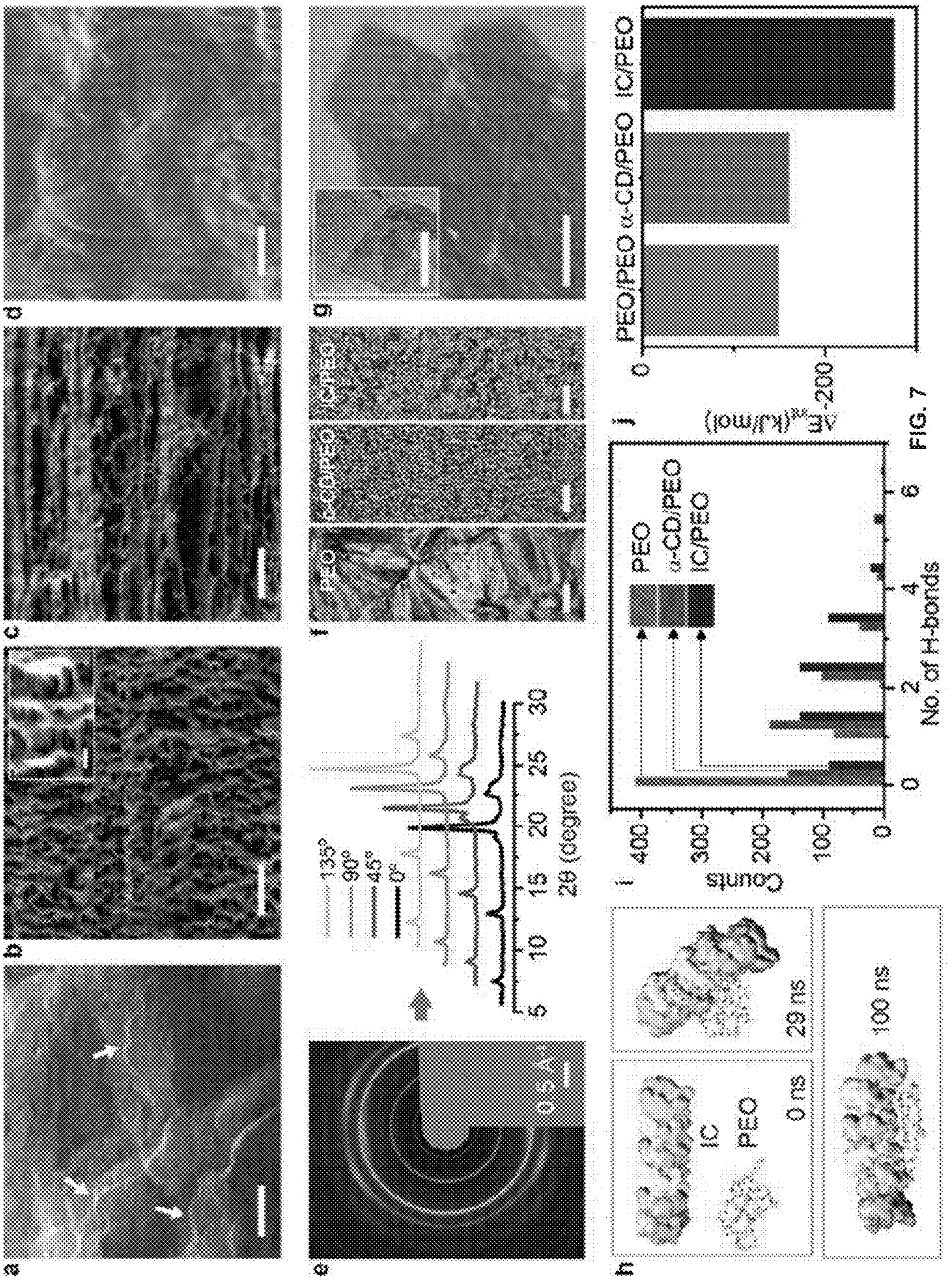
Figure 8:
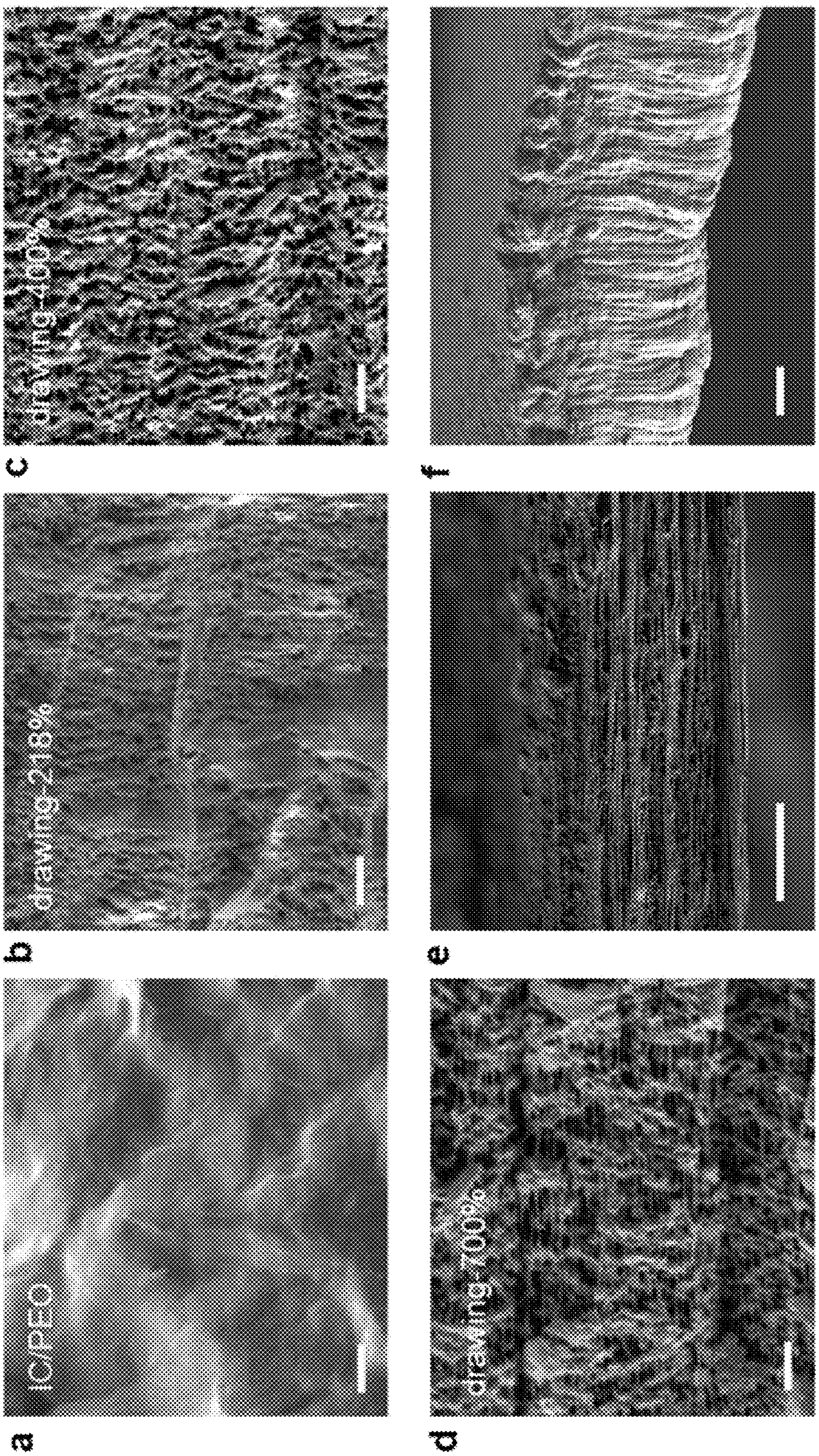
Figure 9:
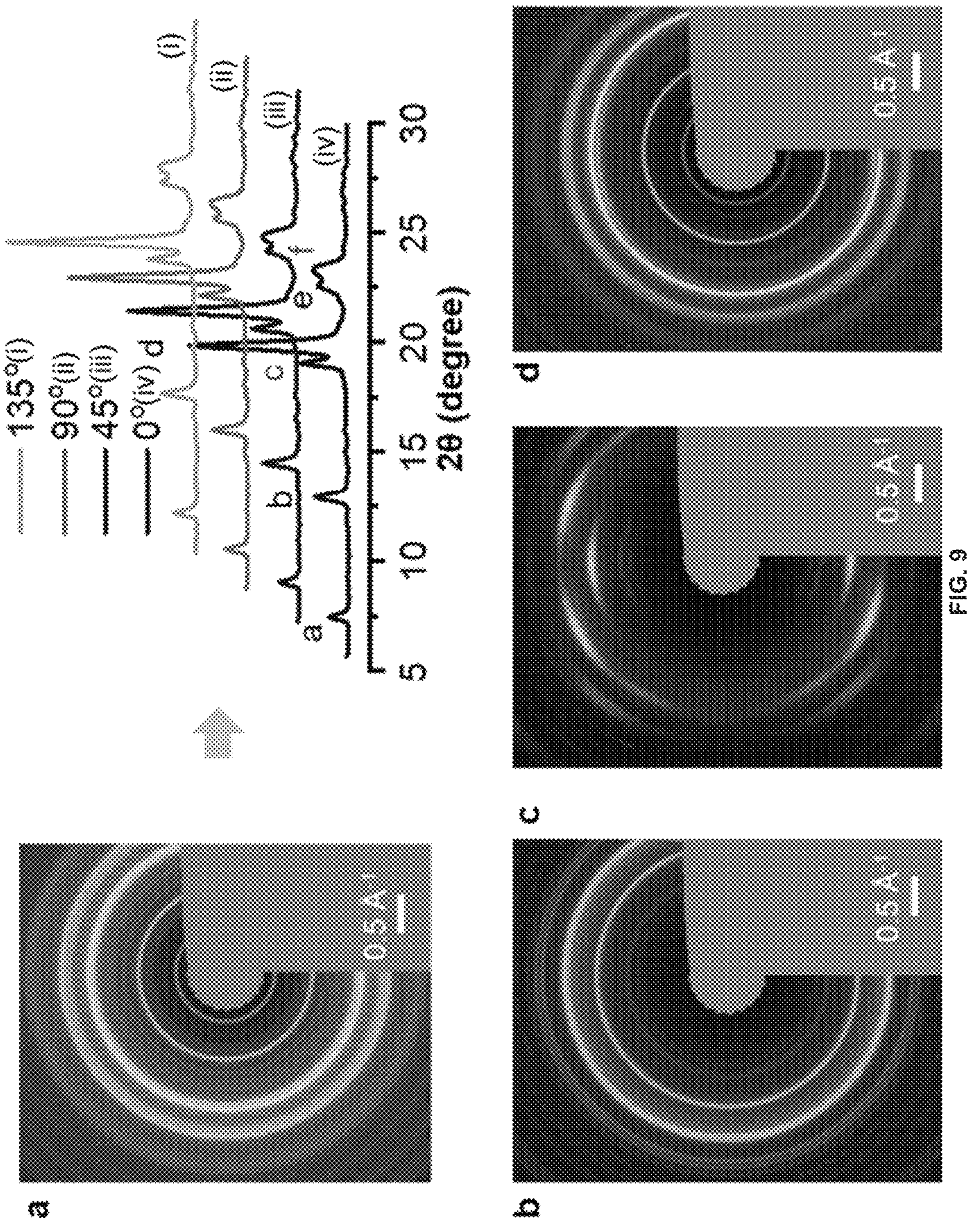

SEM shows that IC/PEO has a smooth and dense surface (FIG. 7*a*). In contrast, SCTF-400% has rough, microporous surface and interior with aligned fibrillar bridges, which were absent after contraction (FIGS. 7*b-d* and 8). The oriented polymer chains are the prerequisite for supercontraction. 2D WAXS profiles and the corresponding 1D analysis show that after cold drawing, patterns belonging to PEO domains (Takahashi, Y. & Tadokoro, H., Macromolecules 1973, 6, 672-675; and Kakade, M. V. et al., *J. Am. Chem. Soc.* 2007, 129, 2777-2782) changed from isotropic to anisotropic which returned to isotropic after contraction and drying while those of IC domains (Huang, L., Allen, E. & Tonelli, A. E., *Polymer* 1998, 39, 4857-4865; and Topchieva, I. N. et al., *Langmuir* 2004, 20, 9036-9043) always remained isotropic (FIGS. 7*e* and 9). Together, these results indicate that drawing produces the aligned and porous microstructures as well as orients the PEO crystallite domains in SCTFs, destroy of which cause supercontraction.

Figure 10:
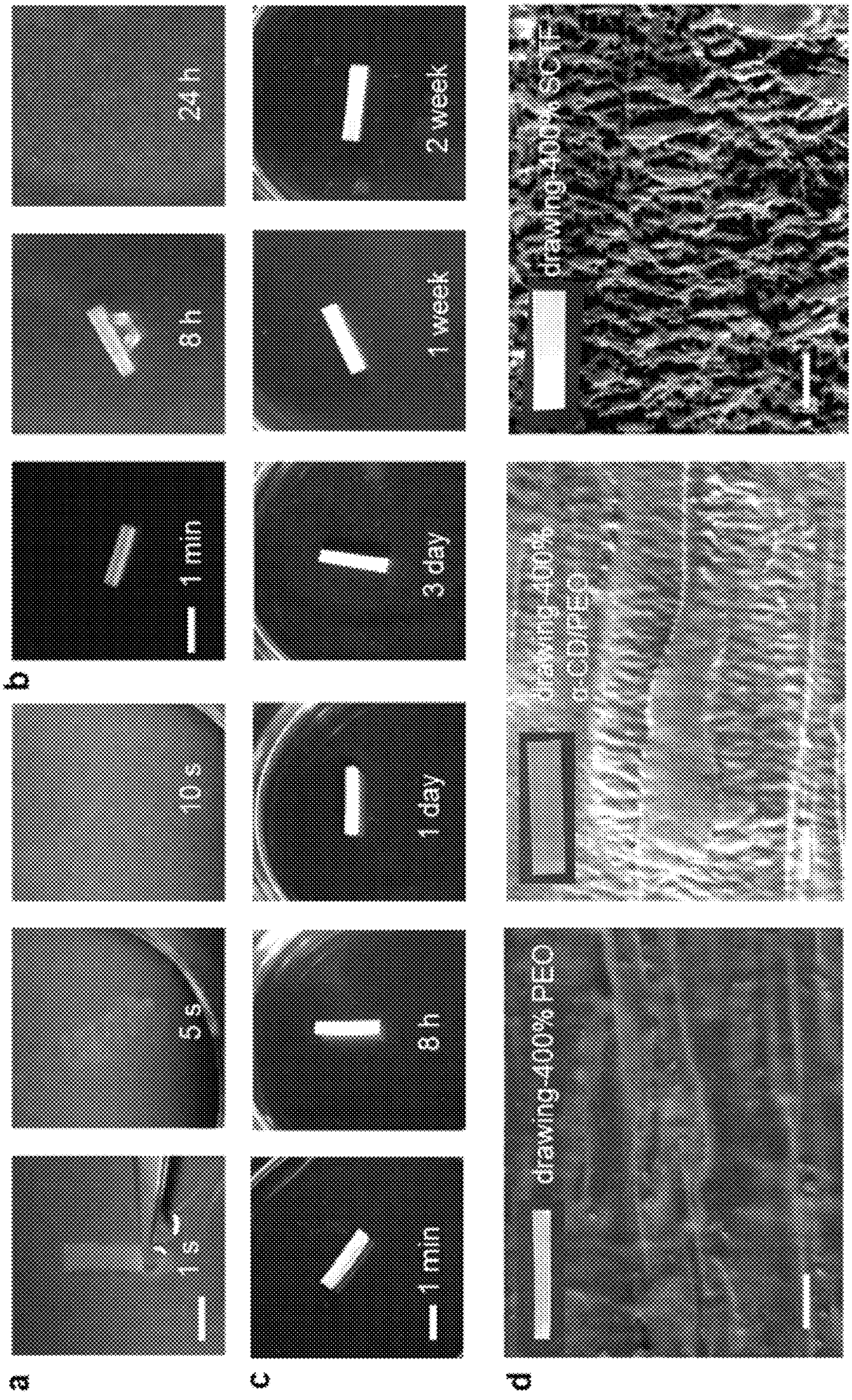

In the control experiments, both drawn pure PEO and α-CD/PEO films (made by mixing α-CD directly with PEO without first forming IC) contracted when wetted. This confirms that it is the drawn PEO part, not the IC, that induced contraction. However, both control films were less stable in water. Pure PEO dissolved immediately while α-CD/PEO dissolved gradually within one day in water. The pc-SCTF-400% was stable (no collapse of pc-matrix) for over 2 weeks (FIGS. 10*a-c*). Moreover, the microporous structure shown in SCTF were absent in drawn PEO and α-CD/PEO films (FIG. 10*d*). Therefore, we conclude that IC is responsible for the porous microstructure and the enhanced post-contraction water stability, both of which are significant for electronics fabrication and application.

Figure 11:
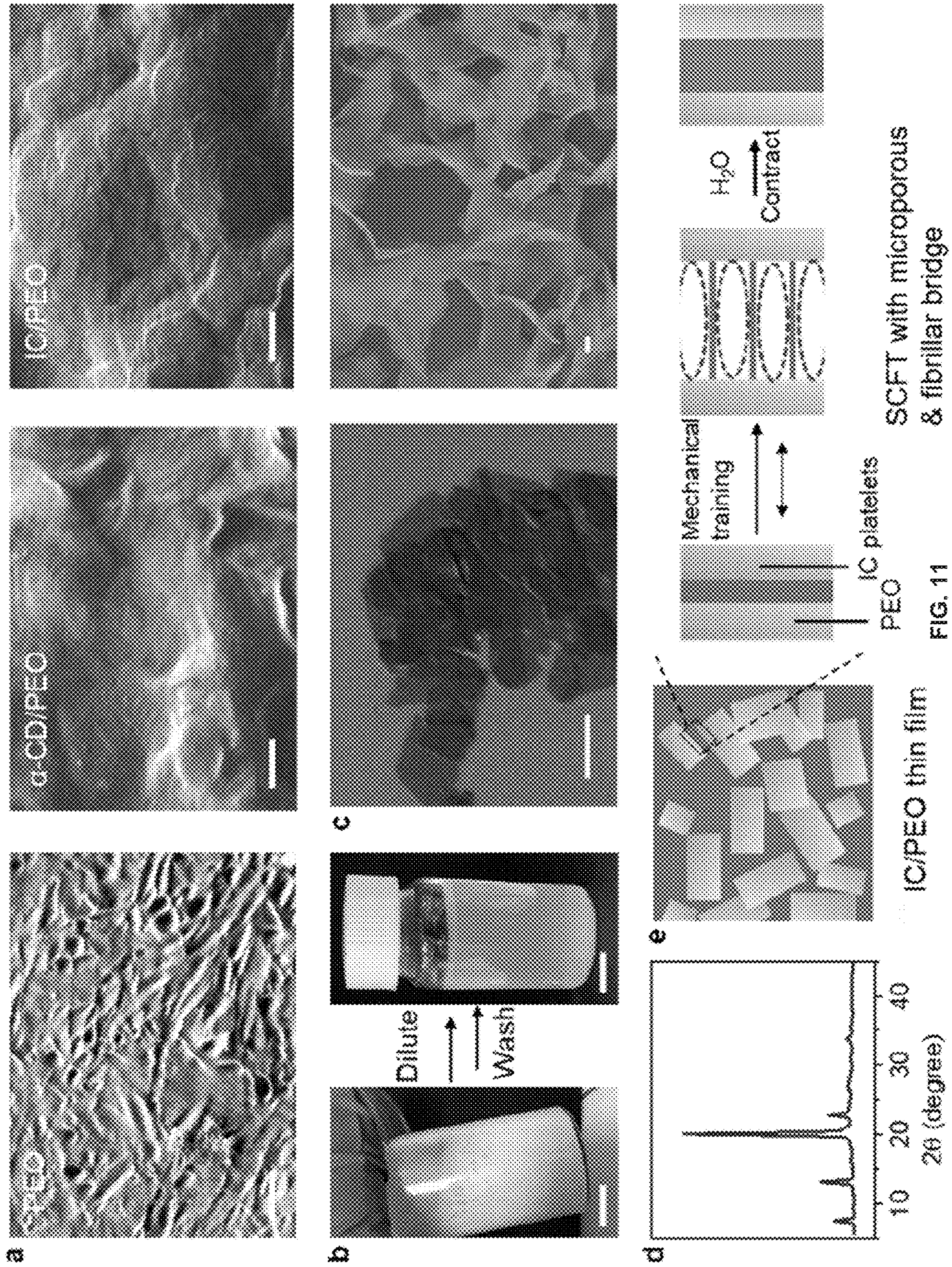

To understand how IC facilitates the formation of the microstructure, we first examined the morphology of the undrawn films. The PEO film showed a typical spherulite structure, which was absent in α-CD/PEO and IC/PEO films (FIG. 7*f*), indicating that both α-CD and IC affected the crystal growth of PEO. Additionally, the surface of IC/PEO had micron-sized stacked platelets (arrows in FIG. 7*a*), which were absent in α-CD/PEO and PEO (FIG. 11*a*). Diluting and washing the IC/PEO mixture before casting produced a suspension with insoluble precipitates, which was confirmed by SEM, TEM and WAXS, to be platelets IC crystal (FIGS. 7*g* and 11*b-d*). Together, these results demonstrate that IC/PEO film has separated IC platelet crystallite domains and PEO domains, drawing of which produce porous and fibrillar bridges microstructure (FIG. 11*e*).

To further understand the stability of pc-SCTF at the molecular level, we performed all-atom MD simulation studying the interaction between IC crystallite and PEO in aqueous solution. In this simulation, PEO and IC molecules were separated some distance at the beginning. After relaxation, they started to attach with each other at ~29 ns and remained aggregated (FIG. 7*h*). Simultaneously, the PEO can form hydrogen bonds with multiple α-CDs in IC with an increase in the radius of gyration (FIG. 12*c*), explaining the potential source of strong binding. In contrast, although simulation between PEO and PEO and between α-CD and PEO show that α-CD and PEO also aggregated, they form less hydrogen bonds than IC/PEO (FIGS. 7*i*, 12*a-b* and 12*d-f*). Further computation of the interaction energy changes shows that the aggregation of IC and PEO had the lowest interaction change (FIGS. 7*j* and 12*g-h*), indicating that dissolution of IC and PEO is more difficult compared to pure PEO and α-CD/PEO. Above all, the strong interactions due to the collective hydrogen bonds formation between IC and PEO should play crucial roles in the stability of pc-SCFT.

Example 5. Fabrication of Multi-Array SCe

As a proof of concept, we used our SCTF prepared in Example 1 to build shape-adaptive SCe for peripheral nerve stimulation and for CMAP recording.

Fabrication of Multi-Array SCe

Figure 14:
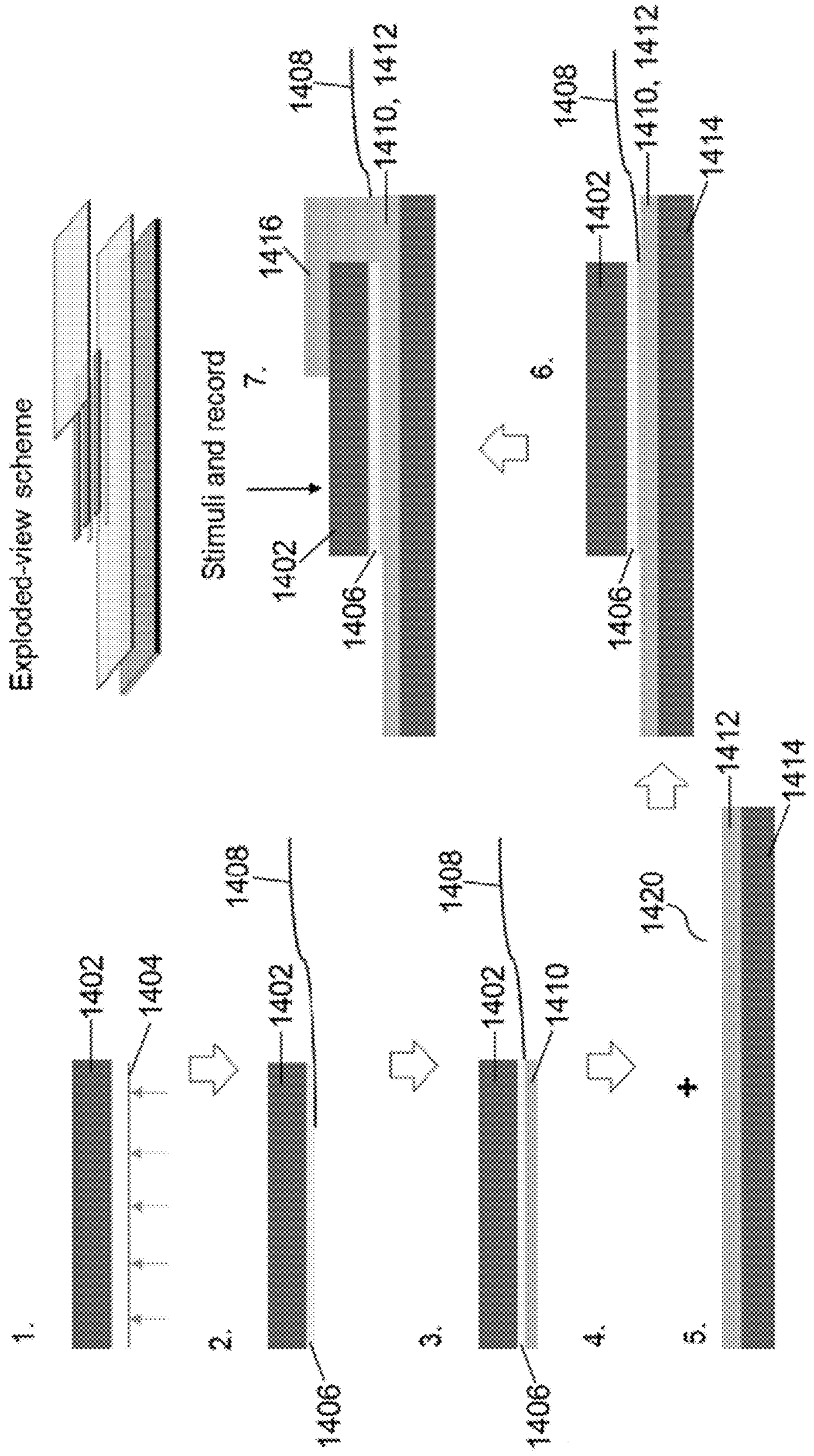

To form a flexible free-standing SCe, we used SCTF as the contractile substrate, gold (Au)-coated SCTF as the multi-array electrode for tissue contact and as interconnects, and SEBS (a commercial thermoplastic elastomer) as insulation layers (FIGS. 13*a* and 14). As depicted in FIG. 14, there is a fabrication process of SCe involving the steps:

1. depositing an Au nanofilm 1406 on a SCTF substrate 1402 with a mask with multi array patterns 1404. Au patterns (size 0.42 mm×13.0 mm) were deposited through thermal deposition;
2. connecting to lead 1408. The lead was connected to the Au pattern by a silver conductive paste;
3. spin-coating SEBS 1410. SEBS (15 wt % toluene solution) was spin-coated at a speed of 500 rpm for 30 s to cover the Au pattern;
4. cutting to get SCTF-Au-SEBS patterns. Cutting was carried out to remove the SCTF-SEBS parts between each pattern. The discrete multi array SCTF-Au contacts (size 1.2 mm×13.0 mm) were obtained thereafter;
5. spin-coating SEBS 1412 on a SCTF substrate 1414. Spin-coating of SEBS (7.5 wt % and 15 wt %) on the piece of SCTF as substrate was carried out through a two-step process. Step 1 was spin-coating SEBS (7.5 wt %) at a speed of 1000 rpm for 30 s and step 2 was spin-coating SEBS (15 wt %) at a speed of 300 rpm for 10 s;
6. adhere the multi array SCTF-Au contacts and SEBS-SCTF 1420 together; and
7. encapsulating certain length of SCTF-Au which serves as interconnect between electrode contact and lead, with SEBS 1416. SEBS 1416 covering on it also served as adhesive to turn 2D planar electrode into 3D hollow cylinder during the surgery. Finally, SCe with SCFT-Au contact size of 1.2 mm×4.0 mm for each array was obtained.

In detail, first, Au patterns (size 0.42 mm×13.0 mm, thickness 100 nm) were deposited on SCTF using mask through thermal deposition (Nano 36, Kurt J. Lesker) at a deposition rate of 0.3 Å/s under evaporation vacuum around $2\times10^{-6}$ Torr. Then, the leads were connected to the Au pattern via silver conductive adhesive (RS 186-3593). Subsequently, SEBS (15 wt % toluene solution) was spin-coated on Au-SCTF at a speed of 500 rpm for 30 s to cover the Au patterns. Then, the SCTF-SEBS part between each pattern was removed to get the discrete multi array SCTF-Au contacts (size 1.2 mm×13.0 mm). Next, a two-step spin-coating process of SEBS (15 wt %) was applied on another piece of SCTF, serving as the substrate. In step 1, the spin-coating condition was at 1000 rpm for 30 s and in step 2 was at 300 rpm for 10 s. Thereafter, multi-array SCTF-Au contacts were adhered to the SCTF-SEBS substrate before the toluene solvent of SEBS solution was totally evaporated. Finally, SCTF-Au except the electrode contact areas (1.2 mm×4.0 mm) were encapsulated by SEBS which serves as the interconnect between the electrode contacts and lead. SEBS covering on them also serves as an adhesive to turn 2D planar electrode into 3D hollow cylinder (closure) during application. Finally, SCe with SCTF-Au contact length of 40 mm was obtained. For Au-elastomer electrode, Au patterns (three arrays, each has size of 1.2 mm×13.0 mm, thickness 100 nm) were deposited through the same thermal deposition method on SEBS. Then, Au patterns except the electrode contact areas (1.2 mm×4.0 mm) and lead connection were covered by another layer of SEBS as encapsulation.

Because our SCTF is dry and microporous, we used vacuum deposition (thermal evaporation) and spin-coating to deposit the Au layer (electronic conducting layer) and SEBS, respectively.

Results and Discussion

Upon wetting, the Au-coated SCTF contracted and transformed into an Au-hydrogel bilayer as anticipated (FIG. 15*a*). The resistance of the pc-Au film only slightly increased from 7.5Ω to 10.8Ω. In contrast, Au films on conventional dry hydrogels that swell isotropically in water typically lose their conductivity because swelling tears the Au film into discontinuous, isolated domains. SCTF, however, contracted along the drawing direction and expanded in the transverse direction. The Au film on pc-SCTF was a continuous mesh consisting of wrinkled micron-sized ribbons (FIGS. 13*b* and 15*b-d*). This structure helps maintain the conductivity of the Au film and makes it stretchable. At 40% strain, the resistance increased less than 20% (FIG. 15*e*). Besides, SEBS adhered seamlessly to SCTF. SEM image shows that SEBS diffused into the microporous structure of the SCTF and formed a mechanical interlock (FIG. 13*c*). SCTF's contraction resulted in a wrinkled SEBS layer (FIG. 15*f*). The electrochemical impedance of our SCe (one contact) was about 625Ω at the electrical field frequency of 1 kHz (FIG. 13*d*). Additionally, the impedance and phase angle values showed little change at 20% and 40% strain, indicating that our SCe is stretchable.

Figure 16:
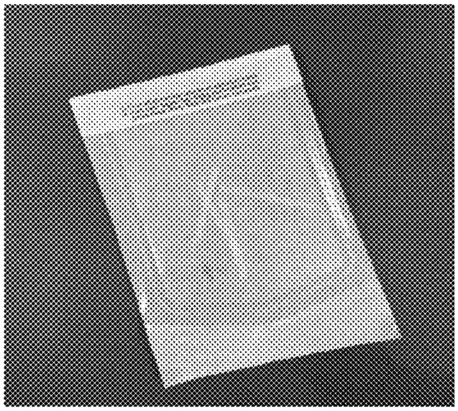

Additionally, our supercontractile thin film and SCe can withstand ultraviolet and ethylene oxide sterilization (FIG. 16) which are widely used sterilization processes in lab and in industry.

Example 6. Electrical Stimulation of SCe and Au-Elastomer Electrode

Stimulation of the electrodes must be efficacious in activating the target neural pathway and do so well within safe stimulation limits. The electrode array should be designed to ensure the electrical stimulus can be localized to discrete groups of neurons. Chronic electrical stimulation must not cause tissue damage or neural loss at the electrode-tissue interface, or dissolution or delamination of the electrode surface.

Voltage Transient Experiments

Voltage transient was measured using GAMRY Potentiostat (Reference 600+) through the chrononpotentiomery mode. The setup for testing is the conventional three-electrode setup in PBS buffer at room temperature (FIG. 24), where the test sample was used as the working electrode, Pt was used as the counter electrode and Ag/AgCl was used as the reference electrode. When testing, a charge-balanced biphasic symmetric square current pulse (cathodal-first, pulse width 200 μs, interpulse delay 10 μs) was applied and the response voltage was recorded. Through the response voltage waveform, both the maximum negative potential excursion (Emc) and maximum positive potential excursion (Ema) can be recorded. The CIC is the maximum charge delivered to make sure Emc and Ema are within the water electrolysis window (e.g. −0.6 V-0.8V for gold electrode). In this work, the Emc and Ema are the electrode potentials recorded 3 μs after the cathodal and anodal pulses end, respectively. CIC was calculated through: CIC=Qinj/A=(Ic×tc)/A, where Qinj is the delivered charge calculated as the time integral of the current, Ic is the cathodal phase current magnitude applying of which makes the Emc reach the water reduction potential (~0.6 V), tc is the width of cathodal current pulse (duration), and A is the geometric surface area of electrode (Cogan, S. F., *Annu. Rev. Biomed. Eng.* 2008, 10, 275-309; Ganji, M. et al., *Adv. Funct. Mater.* 2017, 27, 1703019; and Boehler, C. et al., *Nat. Protoc.* 2020, 15, 3557-3578). The electrode area of WRAP electrode and Au-elastomer electrode was about 2.6 $mm^2$.

Results and Discussion

Figure 17:
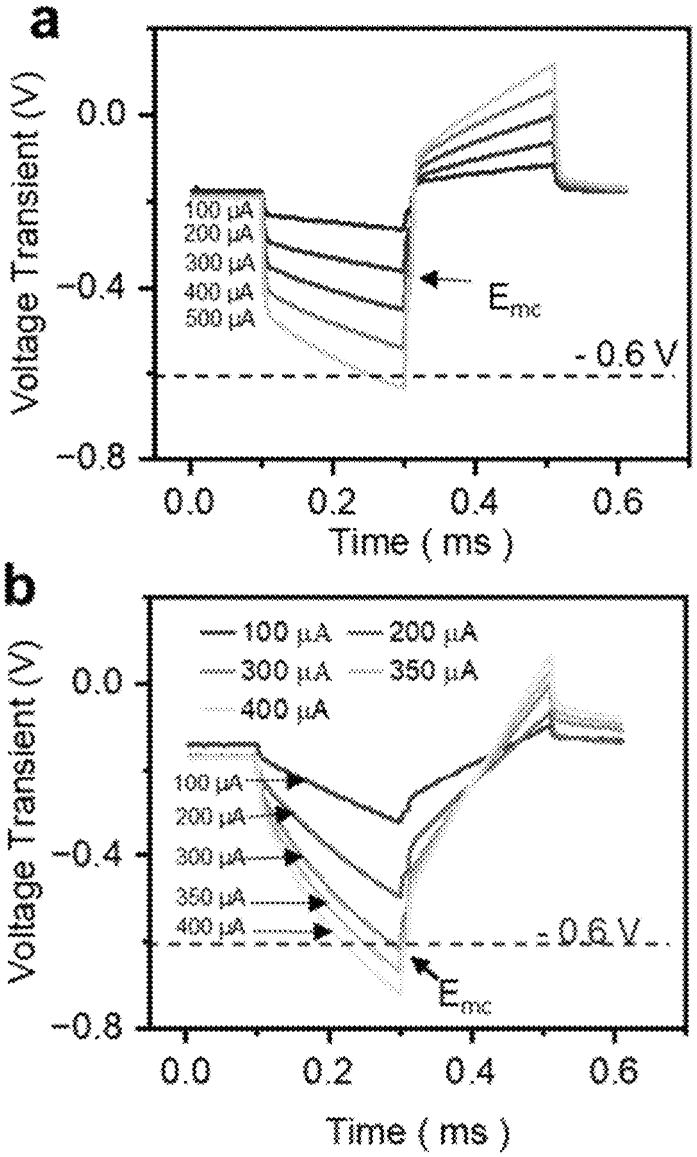

Compared with the inert metal Au, our SCe showed higher CIC (FIG. 17). That means that the safer maximum stimulation current for our SCe is larger than that of Au electrode with the same size.

Example 7. In Vitro Stability of SCe

The electrode array and cable must be designed to minimise movement relative to their target neurons. They must not damage neurons, other tissue, or organs in the vicinity of the implant or result in adverse systemic effects. The implant must be designed to withstand repeated movement, and if it is designed for use in children, the device must accommodate growth-related changes. In addition, the electrode array must be electrically stable over long-term implantation and the insulation must not delaminate or allow fluid ingress resulting in inter-channel crosstalk. Electrical and electrochemical characterizations were performed by following the protocol in Example 3.

Mechanical Stability of SCe Array

The SCe was repeatedly stretched to a strain of 40%. After a certain number of cycle stretch, we measured the impedance of SCe. The setup for testing is the conventional three-electrode setup in PBS buffer at room temperature (FIG. 24), where the test sample used as working electrode, Pt as counter electrode and Ag/AgCl as reference electrode. The tests were performed in Bode model in a frequency range from 1 Hz to 100 kHz with a voltage amplitude of 10 mV.

Electrical Stability of SCe Array

After soaking in 37° C. PBS solution for different periods of time, the impedance of SCe was measured. The setup for testing is the conventional three-electrode setup in PBS buffer at room temperature (FIG. 24), where the test sample used as working electrode, Pt as counter electrode and Ag/AgCl as reference electrode. The tests were performed in Bode model in a frequency range from 1 Hz to 100 kHz with a voltage amplitude of 10 mV.

Results and Discussion

Figure 18:
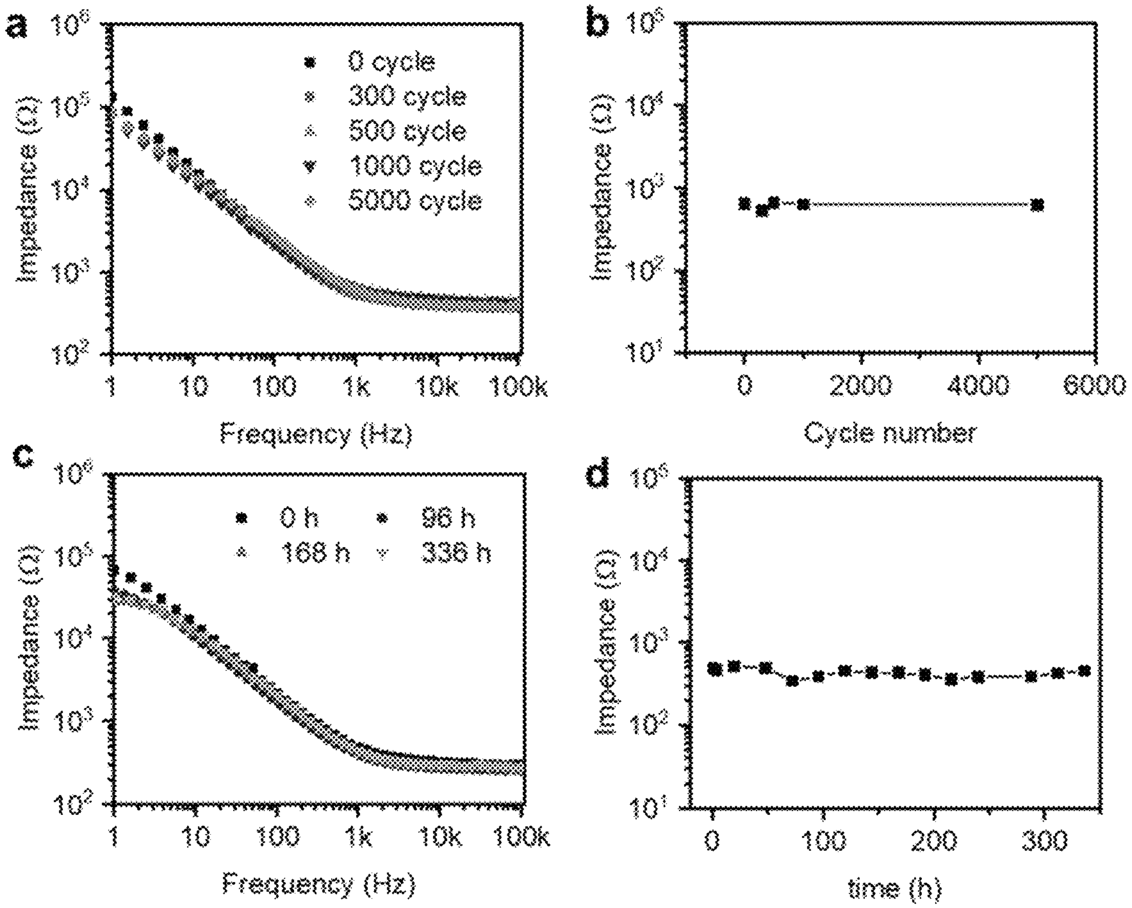

Our SCe is stretchable. The electrode can withstand multiple cycles (FIG. 18). Besides, the cable we used is a commercial implantable cable.

Example 8. SCe for In Vivo Stimulation and Recording

The shape-adaptive SCe prepared in Example 5 were taken for peripheral nerve stimulation and for CMAP recording. Electrical and electrochemical characterizations were performed by following the protocol in Example 3. In addition, the implant must be biocompatible, i.e. the assembled device implanted in the target site must demonstrate long-term biocompatibility.

In Vivo Biocompatibility

In vivo biocompatibility studies were performed by comparing the immune response of sciatic nerves wrapped by the SCe, Au-elastomer electrode and sham control after two-weeks implantation. Each group used 3 rats. The cross-section slices of sciatic nerve were prepared and subjected to H&E staining and CD68 immunostaining at Guangdong NEWAY Testing Laboratory. All procedures were reviewed and approved by the Committee on Animal Care and Use, Guangdong NEWAY Quality Technical Service Co., Ltd.

Statistical analysis of group-group differences was performed using one way ANOVA followed by the Turkey's post hoc test (n=3 independent rats, ***$P<0.001$, NS (not significant) $P>0.05$).

In Vivo Animal Experiments

In the experiment, one healthy Specific pathogen-free (SPF) Sprague Dawley adult male rat (~280 g) was adopted. In preparation for the surgery, the rat was anaesthetized via intraperitoneal injection of sodium pentobarbitone (density 2%, dose 0.3 ml/100 g body weight) and later placed on the operational platform, under which a heating pat at 37° C. was placed. The hair covering the Extensor digitorum longus (EDL muscle) was shaved off. Then, an incision was made to properly visualize and isolate the EDL muscle, common peroneal nerve and sciatic nerve. Then, the SCe were gently placed on the sciatic nerve (~1.3 mm) and common peroneal nerve (~0.5 mm) using the process illustrated in FIG. 15*h* for nerve stimulation. First, SCe packaged with water-proof backing and cover was placed underneath the target nerve. Then, after removal of the protecting cover, the thin film SCe was folded and pressed to adhere to form a hollow cylinder shape, wrapping the target nerve. Finally, after dropping of water, the SCe contracted and became soft hydrogel-based electrode, conformably wrapping around the target nerve.

For simultaneously stimulating and recording experiments, sciatic nerve, common peroneal nerve, tibial nerve, tibialis anterior muscle and soleus muscle were isolated and exposed. Five SCe were implanted around them respectively. Stimulation pulse currents (1 Hz, 100 μs, 50-180 μA) were applied through SCe on sciatic nerves while continuous noninvasive arterial pressure (CNAP) and compound muscle action potential (CMAP) were recorded through SCe on common peroneal nerve, tibial nerve, tibialis anterior muscle and soleus muscle. The stimulator was Plexon StimuPlex V2 STIM/16 and the recording equipment was Plexon OPX-D2 (sampling rate: 40 kHz).

The SCe was wrapped around the EDL muscle for CMAP recording. For recording signal comparison experiment, a polyimide electrode with two channels (anode and cathode) was applied to electrically stimulate (parameters: 1 Hz, 40 μA, and 100 μs) the common peroneal nerve. SCe and Au-elastomer electrode were wrapped around EDL muscle to detect induced CMAP when EDL muscle contracted as a result of electrical stimuli. Post-recording, euthanasia would be performed for this animal by cervical dislocation. The experimental protocol related to animal of this study was assessed and approved by the Committee on the Use and Care of Animals, Shenzhen Institutes of Advanced Technology, Chinese Academy of Sciences.

Results and Discussion

Figure 19:
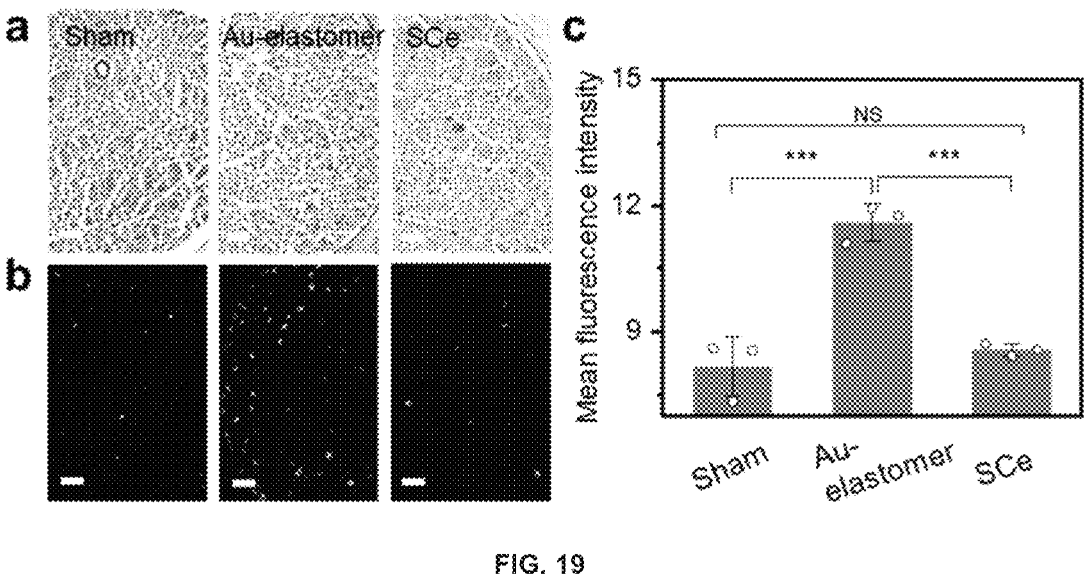

The implant must be designed to minimize the risks of infection. Our SCe (WRAP electrode) caused less inflammatory response of peripheral nerve tissues than Au-elastomer, after two-weeks implantation (FIG. 19).

To demonstrate that SCe can be used for peripheral nerve stimulation, we installed one SCe on the rat sciatic nerve and another on the smaller common peroneal nerve (FIG. 13*e*) through a relatively simple, suture-free procedure (FIGS. 15*g-h*). Despite the nerve size difference (FIG. 15*i*), conformable wrapping was achieved in both nerves using the same-sized SCe because our SCe is shape-adaptive (FIGS. 13*f* and 15*j*). The stimulating pulse currents applied through the SCe on the sciatic nerve moved the rat's leg while pulses on the common peroneal nerve moved the toes (FIG. 13*g*).

Figure 20:
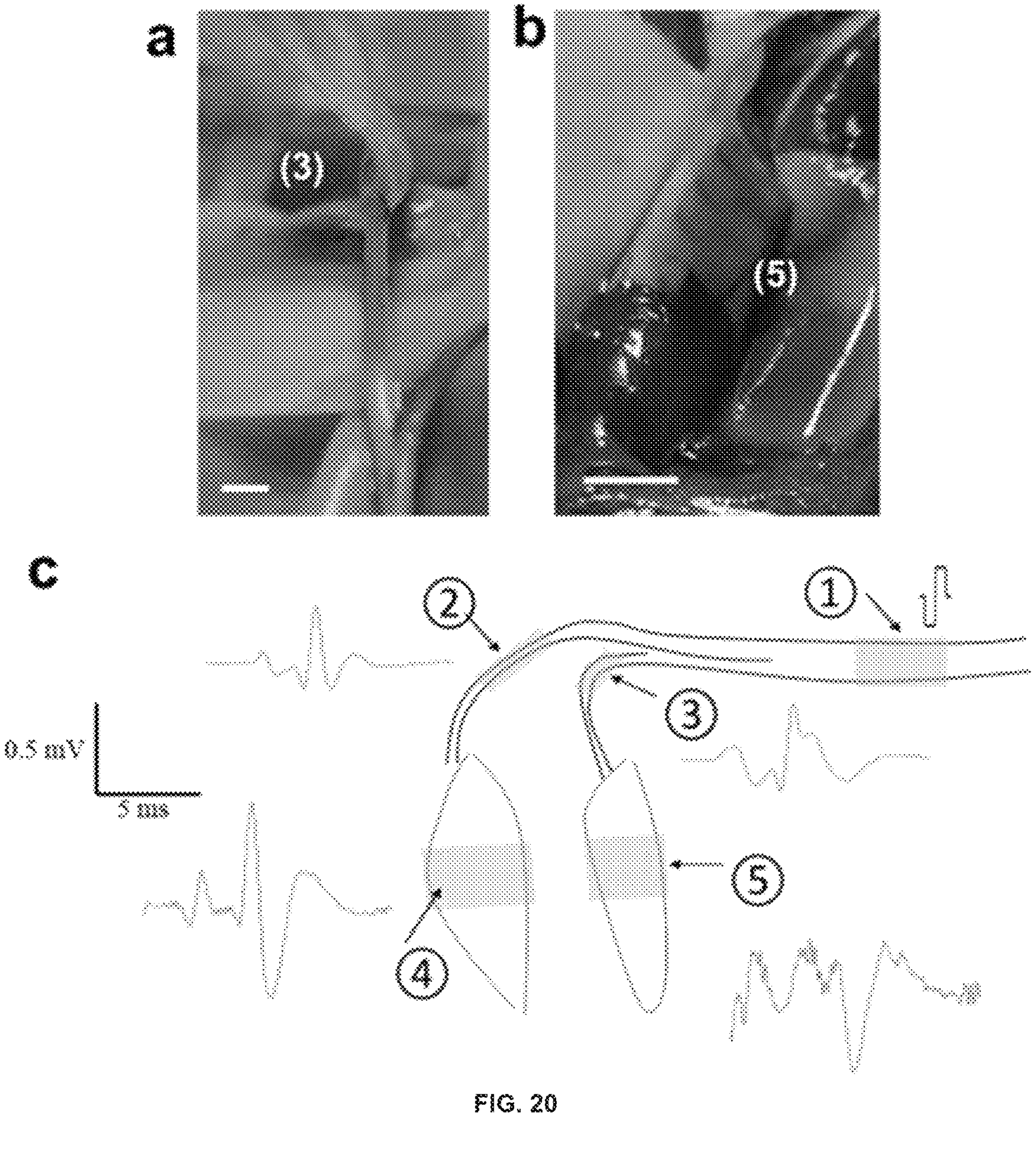
FIG. 20 depicts (a) SCe-wrapped tibial nerve (~0.7 mm), (b) SCe-wrapped soleus muscle (~6 mm); and (c) simultaneously recording compound nerve and muscle action potentials using SCe on sciatic nerve as stimulation electrodes and SCe on other sites as recording electrode.

To demonstrate that SCe can be also used to record electrophysiological signals, we wrapped a third SCe around the EDL muscle, which is innervated by the common peroneal nerve. For comparison, we used an Au-elastomer (Au-SEBS) electrode. Despite the irregular shape of the EDL muscle, our SCe wrapped conformably around the muscle after wetting (FIG. 13*h*) unlike the Au-elastomer electrode, which formed gaps at the electrode-tissue interface (arrows in FIG. 13*i*). CMAP signals were collected through the SCe around the muscle while the common peroneal nerve was stimulated. Our SCe recorded clear evoked signals (FIG. 13*j*) and had a lower base noise than those recorded by Au-elastomer electrode (FIG. 13*k*). As depicted in FIG. 20, we also used SCe to wrap the (1) sciatic nerve (~1.3 mm), (2) common peroneal nerve (~0.5 mm), (3) tibial nerve (~0.7 mm), (4) tibialis anterior muscle (~13 mm), and (5) soleus muscle (~6 mm). In addition, we used SCe on sciatic nerve to deliver stimulation current and used SCe on other sites to record compound nerve and muscle action potentials (FIG. 20). These in vivo experiments demonstrate that our SCe is shape-adaptive in that it wraps around nerve and muscle tissues without the need for suturing or customization, and they can be used for both nerve stimulation and electrophysiological signal recording.

Figure 21:
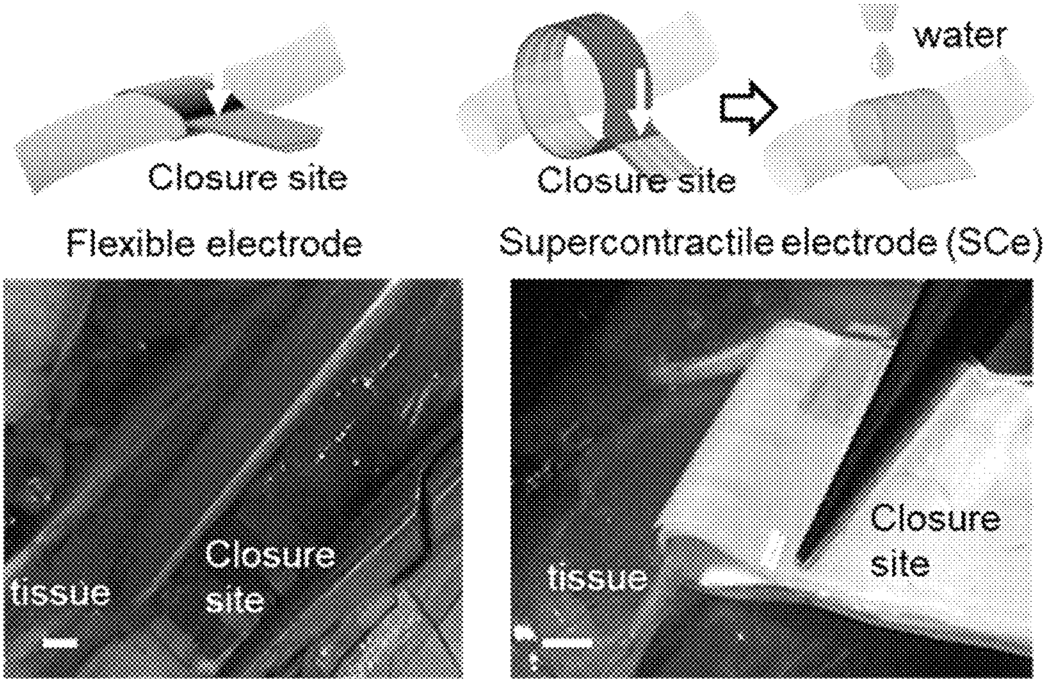
FIG. 21 depicts the safe implantation process of SCe (WRAP) electrode.

Further, our SCe electrode enables a safe electrode implantation process. Surgical insertion of the neural stimulator must be achieved with minimal damage to the electrode array or the target neural population and surrounding tissue. Commercial cuff electrodes composed of rigid electrode contacts and fixed shape are commercialized products for extra-neural peripheral nerve electrode. They usually wrap around nerves with different closure strategy (e.g. suture, buckle, piano hinge and adhesives) to avoid escaping of the tissues or relative movement. However, their shape and size need to be customized in advance and usually cannot perfectly match the target tissues which result in either loose contact or tight contact. Tight wrap can generate uncontrollable compression force while loose wrap diminishes the electrode function and causes relative movement between electrode and tissues. The closure process is difficult to operate and has risk to damage tissues especially for the small size targets and for nerves which are sensitive to chemicals and mechanical forces. For our WRAP shape-adaptive SCe, the closure sites can be at a certain distance to the underlying tissues to get a loose wrap at first, then a seamless wrap is achieved by the subsequently water-triggered automatically contraction (FIG. 21). The pc-SCe becomes soft, which mechanically matches with soft tissues.

Example 9. Use of Long-Term Electrodes for Recording Very Weak Sensory Nerve Signals We implanted our SCe (prepared in Example 5) on sciatic nerve by following the protocol in Example 8, and recorded the sensory nerve signals.

Recording Sensory Nerve Signals Under Mechanical and Temperature Stimulus

In electroneurogram (ENG) recording experiments, three healthy Specific pathogen-free (SPF) Sprague Dawley adult male rats (~300 g) were adopted. SCe or Au-elastomer were implanted through shape-adaptive contraction or self-locking on the sciatic nerve. A stainless-steel electrode used as reference was implanted subcutaneously in the back above the pelvis. The leads of the electrodes were subcutaneously tunnelled and connected to a headstage fixed to the skull. Anti-inflammatory and analgesic treatments were performed with penicillin sodium (10 IU/time, intraperitoneal injection) and meloxicam (4 mg/kg (body weight), subcutaneous injection) for the first 3 days. The headstage was connected to the data acquisition equipment (Plexon OPX-D2, sampling rate: 40 kHz) during recording. During the data acquisition, the rats were anesthetized. The temperature stimulation was applied by alternatively dropping cold (8° C.) and hot (55° C.) water on the hindpaw of rat every 20 seconds. The mechanical stimulation was applied by repeated bushing the hindpaw every 5 seconds. The raw data were bandpass filtered (800-10000 Hz) through a 3rd order Butterworth filter.

Results and Discussion

Figure 22:
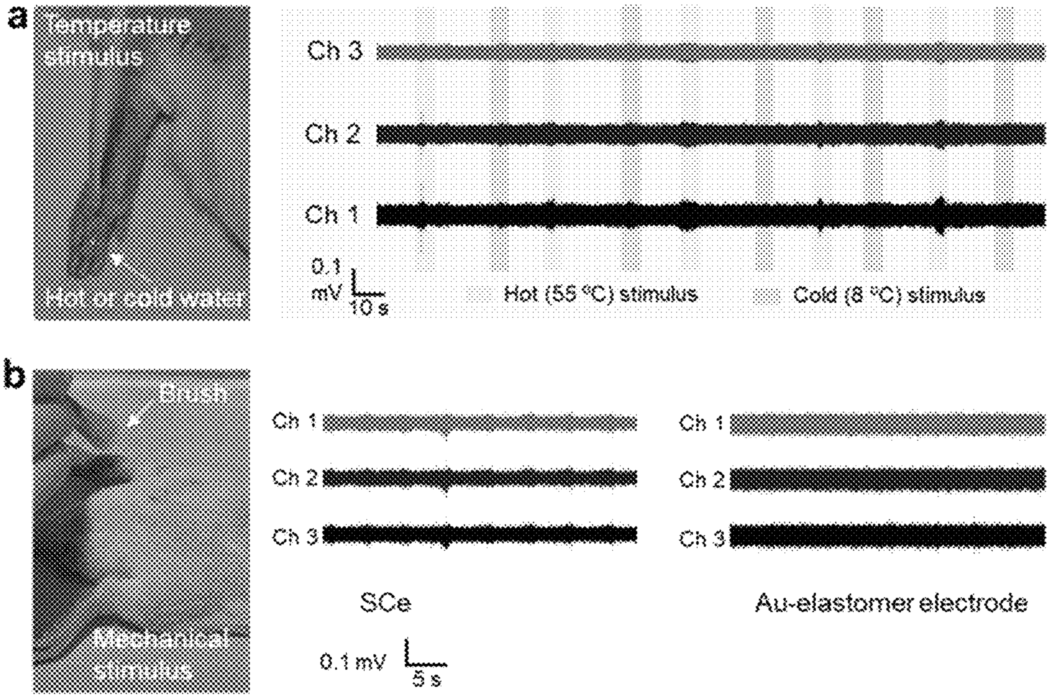
FIG. 22 depicts (a) neural signal recording during temperature stimulation, and (b) neural signal recording during mechanical stimulation.

We implanted our SCe on sciatic nerve and recorded very weak sensory nerve signals under mechanical and temperature stimulus (FIG. 22).

Example 10. Implantable Electrodes for Regenerative Peripheral Nerve Interface (RPNI)

The amplitude and stability of peripheral nerve signals are weak, limiting the applications such as controlling neuroprosthetic devices. RPNI is a novel technique which implant a transected end of peripheral nerve into a free muscle graft. Such muscle graft can serve as a bioamplifier of efferent motor action potentials, which can be used to control the neuroprosthetic devices or treating phantom pain and neuroma pain after amputation. Here, we used SCe (prepared in Example 5) to wrap the muscle graft with different sizes and shapes by following the protocol in Example 8.

Application of SCe on RPNI Technique

In the RPNI experiment, three healthy Specific pathogen-free (SPF) Sprague Dawley adult male rat (~270 g) were adopted and applied RPNI surgery. During the surgery, a free soleus muscle was harvested and grafted to the proximal end of the transected common peroneal nerve. Then, the WRAP electrode was gently wrapped around the muscle graft. After applying water, the SCe contracted to conformally wrap the muscle graft. A stainless-steel electrode was used as the reference, which was implanted subcutaneously in the back above the pelvis. The leads of the electrodes were subcutaneously tunnelled and connect to a headstage fixed to the skull. Anti-inflammatory and analgesic treatments were performed with penicillin sodium (10 IU/time, intraperitoneal injection) and meloxicam (4 mg/kg (body weight), subcutaneous injection) for the first 3 days. The headstage was connected to the data acquisition equipment (Plexon OPX-D2, sampling rate: 40 kHz) during recording. The EMG signals of RPNI were recorded when the rats walked on a rat wheel. The wheel was manually rotated a quarter turn every 5 seconds. For data processing, the raw EMG signals were first downsampled to 2000 Hz and then bandpass filtered (20-350 Hz) through a 3rd order Butterworth filter. For signal with electrocardiographic (ECG) interference, the template subtraction (TS) method was used to remove ECG from EMG signals.

The experimental protocols related to nerve stimulation, CNAP, CMAP, ENG and RPNI recording of this study were assessed and approved by the Committee on the Use and Care of Animals, Shenzhen Institutes of Advanced Technology, Chinese Academy of Sciences.

Results and Discussion

Figure 23:
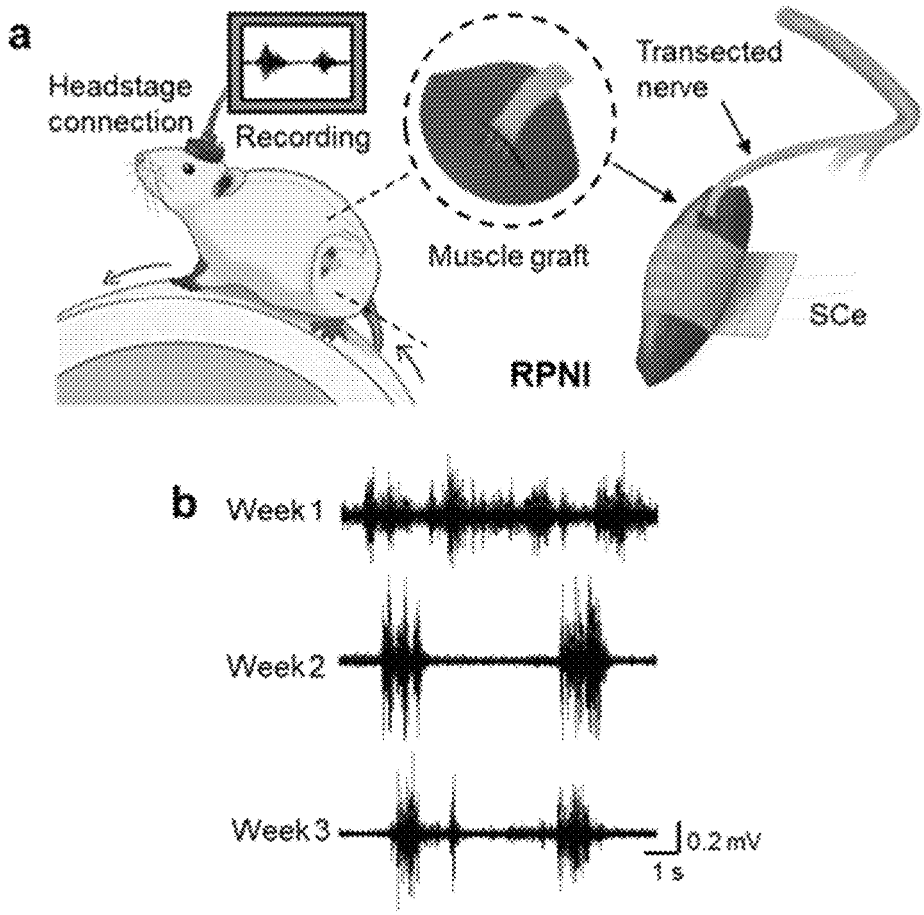
FIG. 23 depicts (a) regenerative peripheral nerve interface (RPNI) on rat's peripheral nerve, and (b) electromyogram (EMG) signals recorded through SCe wrap on muscle graft.

We used SCe to wrap the muscle graft with different sizes and shapes and successfully recorded the EMG signals during the movement of the rat (FIG. 23). These experiment show the potential application of SCe on RPNI technique.

In summary, we fabricated SCTF using a simple combination of α-CD, PEG and PEO to achieve spider-silk-like supercontraction. Our SCTF, which is initially dry and flexible, contracts significantly and instantly when wetted and transforms itself into a soft and stretchable hydrogel thin film, which makes it very easy to replace by slightly stretching it and cutting the closure site. SCTF possesses aligned, microporous hierarchical structure constructed by IC crystalline domains and oriented PEO domains. We developed SCe using SCTF and showed that they can wrap shape-adaptively and conformably around tissues of different sizes and shapes such as nerves and muscles, achieving nerve stimulation and electrophysiological signal recording. We envision that more sophisticated shape-adaptive electronics with added functionalities and other smart devices for applications like nerve repair, wound closure and scar reduction can be realized in the future.

The invention claimed is:

1. A supercontractible thin film comprising:

crystalline inclusion complex domains formed from poly (pseudo) rotaxanes or polyrotaxanes; and oriented polyethylene oxide domains physically cross-linked to the crystalline inclusion complex domains, wherein:

the poly(pseudo) rotaxanes or polyrotaxanes are formed from α-cyclodextrin and a polyethylene glycol having a number average molecular weight of from 500 to 10,000 Daltons;

the polyethylene oxide has a number average molecular weight of from 200,000 to 10,000,000 Daltons; and the supercontractible thin film contracts by more than 50% of its original length upon wetting with water.

2. The supercontractible thin film according to claim 1, wherein the thin film has one or both of a microporous structure and aligned fibrillar bridges.

3. The supercontractible thin film according to claim 1, wherein the supercontractible thin film exhibits a contraction rate relative to its original length of from 10 to 50%/s upon wetting with water.

4. The supercontractible thin film according to claim 3, wherein the supercontractible thin film exhibits a contraction rate relative to its original length of about 30%/s upon wetting with water.

5. The supercontractible thin film according to claim 1, wherein the weight: weight ratio of polyethylene glycol: α-cyclodextrin is from 1:1 to 1:20.

6. The supercontractible thin film according to claim 1, wherein the weight: weight ratio of α-cyclodextrin:polyethylene oxide is from 1:1 to 10:1.

7. The supercontractible thin film according to claim 1, wherein the weight: weight ratio of polyethylene glycol: α-cyclodextrin: polyethylene oxide is about 1:10:6.

8. The supercontractible thin film according to claim 1, wherein one or more of the following apply:
(a) the supercontractible thin film is stable at a temperature of less than 60° C. and a relative humidity of less than 80%;
(b) the film is stable in an aqueous solvent for a period of at least two weeks;
(c) the poly(pseudo) rotaxanes or polyrotaxanes are formed from the α-cyclodextrin and the polyethylene glycol having a number average molecular weight of from 1,000 to 7,500 Daltons; and
(d) the polyethylene oxide has a number average molecular weight of from 500,000 to 7,000,000 Daltons.

9. The supercontractible thin film according to claim 1, wherein the supercontractible thin film has a Young's modulus of from 50 MPa to 1 GPa.

10. The supercontractible thin film according to claim 1, wherein the supercontractible thin film has been subjected to longitudinal stretching to provide the oriented polyethylene oxide domains, where the longitudinal stretching results in a film having a length that is from 218 to 700% of the original length of a freestanding thin film material comprising:
crystalline inclusion complex domains formed from polyrotaxanes or poly(pseudo) rotaxanes; and
unoriented polyethylene oxide domains physically crosslinked to the crystalline inclusion complex domains.

11. The supercontractible thin film according to claim 1, wherein the supercontractible thin film contracts by from 35 to 65% of its original length upon wetting with water.

12. A shape-adaptive supercontractile electrode comprising:
a first layer of a supercontractible thin film according to claim 1 as a substrate;
an electrode composite material comprising:
a second layer of supercontractible thin film according to claim 1 as an electrode support layer; and
a conductive metal compound layer or a metal layer arranged to form electrodes and attached to the second supercontractible thin film layer;
a first insulation layer sandwiched between the first supercontractible thin film layer and the electrode composite material; and
a second insulation layer on laid on top of the electrode composite material, wherein the first and second insulation layers are formed from an insulative polymeric material.

13. The shape-adaptive supercontractile electronic device according to claim 12, wherein the insulative polymeric material is selected from PDMS or a thermoplastic elastomer.

14. The shape-adaptive supercontractile electronic device according to claim 13, wherein the insulative polymeric material is styrene-ethylene/butylene-styrene.

15. The shape-adaptive supercontractile electronic device according to claim 12, wherein:
(AA) when a metal layer is present, the metal layer includes is selected from one or more of platinum and, more particularly, gold, silver, or copper, or when a conductive metal compound layer is present, the conductive metal compound is selected from one or both of iridium oxide and titanium nitride;
(AB) the electrode composite material is patterned; and
(AC) the electrode composite material further comprises a layer of an insulative polymeric material on top of the conductive metal compound layer or, more particularly, the metal layer.

16. A supercontractile electronic device comprising a supercontractible thin film layer according to claim 1.

17. A supercontractile electronic device comprising a shape-adaptive supercontractile electrode according to claim 12.

18. A method of forming a supercontractible thin film as described in claim 1, the method comprising the steps of:
(ai) providing a freestanding thin film comprising:
the crystalline inclusion complex domains formed from the polyrotaxanes or the poly(pseudo) rotaxanes; and
the unoriented polyethylene oxide domains physically crosslinked to the crystalline inclusion complex domains, wherein:
the polyrotaxanes or poly(pseudo) rotaxanes are formed from the α-cyclodextrin and the polyethylene glycol having a number average molecular weight of from 500 to 10,000 Daltons; and
the polyethylene oxide has a number average molecular weight of from 200,000 to 10,000,000 Daltons; and
(aii) drawing a film by applying a strain to achieve an elongation of the film of from 100% to 300% of its original length to provide the supercontractible thin film.

19. A method of forming a freestanding film as described in claim 18, the method comprising:
(bi) providing a composition comprising α-cyclodextrin-poly(ethylene glycol) inclusion complex and a solvent;
(bii) adding poly(ethylene oxide) (PEO) to the composition and aging for a period of time at a temperature of from 40 to 80° C. to provide a freestanding film precursor solution; and
(biii) drying the freestanding film precursor solution to provide the freestanding film precursor.

20. A method of forming an electrode composite material, the method comprising:
(ci) providing a supercontractible thin film according to claim 1 as a substrate; and
(cii) depositing a conductive metal compound or a metal by thermal deposition onto the supercontractible thin film substrate to form a conductive metal compound layer or a metal layer, respectively.

* * * * *